(12) United States Patent
Otto

(10) Patent No.: US 11,642,027 B2
(45) Date of Patent: May 9, 2023

(54) METHODS AND APPARATUS FOR THE PLANNING AND DELIVERY OF RADIATION TREATMENTS

(71) Applicant: Siemens Healthineers International AG, Steinhausen (CH)

(72) Inventor: Karl Otto, Salt Spring Island (CA)

(73) Assignee: SIEMENS HEALTHINEERS INTERNATIONAL AG, Steinhausen (CH)

(*) Notice: Subject to any disclaimer, the term of this patent is extended or adjusted under 35 U.S.C. 154(b) by 544 days.

(21) Appl. No.: 16/793,962

(22) Filed: Feb. 18, 2020

(65) Prior Publication Data
US 2020/0178890 A1 Jun. 11, 2020

Related U.S. Application Data

(63) Continuation of application No. 15/707,931, filed on Sep. 18, 2017, now Pat. No. 10,595,774, which is a (Continued)

(51) Int. Cl.
*A61B 5/00* (2006.01)
*A61N 5/10* (2006.01)
(Continued)

(52) U.S. Cl.
CPC .............. *A61B 5/0036* (2018.08); *A61B 5/08* (2013.01); *A61B 5/113* (2013.01); *A61B 34/10* (2016.02);
(Continued)

(58) Field of Classification Search
CPC .. A61N 5/1082; A61N 5/1049; A61N 5/1047; A61N 5/1037; A61N 5/1031;
(Continued)

(56) References Cited

U.S. PATENT DOCUMENTS

| 3,133,227 A | 5/1964 | Brown et al. |
| 3,144,552 A | 8/1964 | Schonberg et al. |

(Continued)

FOREIGN PATENT DOCUMENTS

| AU | 746987 B2 | 2/2000 |
| AU | 2002215340 B2 | 4/2002 |

(Continued)

OTHER PUBLICATIONS

Jaffray et al., "Flat-panel Cone-beam Computed Tomography for Image-Guided Radiation Therapy", Int. J. Radiation Oncology Biol. Phys., vol. 53, No. 5, 2002, pp. 1337-1349.
(Continued)

*Primary Examiner* — Christine H Matthews
*Assistant Examiner* — Joshua Daryl D Lannu
(74) *Attorney, Agent, or Firm* — Potomac Law Group, PLLC

(57) ABSTRACT

Methods and apparatus are provided for planning and delivering radiation treatments by modalities which involve moving a radiation source along a trajectory relative to a subject while delivering radiation to the subject. In some embodiments the radiation source is moved continuously along the trajectory while in some embodiments the radiation source is moved intermittently. Some embodiments involve the optimization of the radiation delivery plan to meet various optimization goals while meeting a number of constraints. For each of a number of control points along a trajectory, a radiation delivery plan may comprise: a set of motion axes parameters, a set of beam shape parameters and a beam intensity.

20 Claims, 19 Drawing Sheets

Related U.S. Application Data continuation of application No. 15/382,469, filed on Dec. 16, 2016, now Pat. No. 9,788,783, which is a continuation of application No. 14/710,485, filed on May 12, 2015, now Pat. No. 9,630,025, which is a continuation of application No. 14/202,305, filed on Mar. 10, 2014, now Pat. No. 9,050,459, which is a continuation of application No. 12/986,420, filed on Jan. 7, 2011, now Pat. No. 8,696,538, which is a continuation of application No. 12/132,597, filed on Jun. 3, 2008, now Pat. No. 7,880,154, which is a continuation-in-part of application No. 11/996,932, filed as application No. PCT/CA2006/001225 on Jul. 25, 2006, now Pat. No. 7,906,770.

(60) Provisional application No. 60/701,974, filed on Jul. 25, 2005.

(51) Int. Cl.
   *A61B 5/113* (2006.01)
   *A61B 5/08* (2006.01)
   *A61B 34/10* (2016.01)

(52) U.S. Cl.
   CPC ............ *A61N 5/103* (2013.01); *A61N 5/107* (2013.01); *A61N 5/1031* (2013.01); *A61N 5/1036* (2013.01); *A61N 5/1037* (2013.01); *A61N 5/1039* (2013.01); *A61N 5/1042* (2013.01); *A61N 5/1045* (2013.01); *A61N 5/1047* (2013.01); *A61N 5/1049* (2013.01); *A61N 5/1077* (2013.01); *A61N 5/1082* (2013.01); *A61B 2034/101* (2016.02); *A61N 2005/1032* (2013.01); *A61N 2005/1034* (2013.01); *A61N 2005/1035* (2013.01)

(58) Field of Classification Search
   CPC .... A61N 5/1045; A61N 5/1042; A61N 5/107; A61N 5/1039; A61N 5/1077; A61N 2005/1032; A61N 2005/1034; A61N 5/1036; A61N 5/103; A61N 2005/1035; A61B 5/113; A61B 5/0036; A61B 34/10; A61B 2034/101; A61B 5/08
   See application file for complete search history.

(56) References Cited

U.S. PATENT DOCUMENTS

| | | |
|---|---|---|
| 3,193,717 A | 7/1965 | Nunan |
| 3,906,233 A | 9/1975 | Vogel |
| 3,987,281 A | 10/1976 | Hodes |
| 4,149,247 A | 4/1979 | Pavkovich et al. |
| 4,149,248 A | 4/1979 | Pavkovich |
| 4,208,675 A | 6/1980 | Bajon et al. |
| 4,209,706 A | 6/1980 | Nunan |
| 4,521,808 A | 6/1985 | Ong et al. |
| 4,547,892 A | 10/1985 | Richey et al. |
| 4,593,967 A | 6/1986 | Haugen |
| 4,628,523 A | 12/1986 | Heflin |
| 4,675,731 A | 6/1987 | Takasu et al. |
| 4,679,076 A | 7/1987 | Vikterlof et al. |
| 4,726,046 A | 2/1988 | Nunan |
| 4,741,621 A | 5/1988 | Taft et al. |
| 4,825,393 A | 4/1989 | Nishiya |
| 4,853,777 A | 8/1989 | Hupp |
| 4,868,843 A | 9/1989 | Nunan |
| 4,868,844 A | 9/1989 | Nunan |
| 5,001,344 A | 3/1991 | Kato et al. |
| 5,014,292 A | 5/1991 | Siczek et al. |
| 5,027,818 A | 7/1991 | Bova et al. |
| 5,039,867 A | 8/1991 | Nishihara et al. |
| 5,080,100 A | 1/1992 | Trotel |
| 5,099,505 A | 3/1992 | Seppi et al. |
| 5,117,445 A | 5/1992 | Seppi et al. |
| 5,157,707 A | 10/1992 | Ohlson |
| 5,168,532 A | 12/1992 | Seppi et al. |
| 5,207,223 A | 5/1993 | Adler |
| 5,247,555 A | 9/1993 | Moore et al. |
| 5,262,649 A | 11/1993 | Antonuk et al. |
| 5,332,908 A | 7/1994 | Weidlich |
| 5,335,255 A | 8/1994 | Seppi et al. |
| 5,394,452 A | 2/1995 | Swerdloff et al. |
| 5,400,255 A | 3/1995 | Hu |
| 5,411,026 A | 5/1995 | Carol |
| 5,427,097 A | 6/1995 | Depp |
| 5,438,991 A | 8/1995 | Yu et al. |
| 5,442,675 A | 8/1995 | Swerdloff et al. |
| 5,471,516 A | 11/1995 | Nunan |
| 5,471,546 A | 11/1995 | Meier |
| 5,509,042 A | 4/1996 | Mazess |
| 5,521,957 A | 5/1996 | Hansen |
| 5,537,452 A | 7/1996 | Shepherd et al. |
| 5,591,983 A | 1/1997 | Yao |
| 5,647,663 A | 7/1997 | Holmes |
| 5,661,773 A | 8/1997 | Swerdloff et al. |
| 5,663,995 A | 9/1997 | Hu |
| 5,663,999 A | 9/1997 | Siochi |
| 5,673,300 A | 9/1997 | Reckwerdt et al. |
| 5,675,625 A | 10/1997 | Rockseisen |
| 5,692,507 A | 12/1997 | Seppi et al. |
| 5,719,914 A | 2/1998 | Rand et al. |
| 5,724,400 A | 3/1998 | Swerdloff et al. |
| 5,727,554 A | 3/1998 | Kalend et al. |
| 5,748,700 A | 5/1998 | Shepherd et al. |
| 5,748,703 A | 5/1998 | Cosman |
| 5,751,781 A | 5/1998 | Brown et al. |
| 5,757,881 A | 5/1998 | Hughes |
| 5,802,136 A | 9/1998 | Carol |
| 5,818,902 A | 10/1998 | Yu |
| 5,835,558 A | 11/1998 | Maschke |
| 5,848,126 A | 12/1998 | Fujita et al. |
| 5,858,891 A | 1/1999 | Auzel et al. |
| 5,877,501 A | 3/1999 | Ivan et al. |
| 5,912,943 A | 6/1999 | Deucher et al. |
| 5,926,521 A | 7/1999 | Tam |
| 5,929,449 A | 7/1999 | Huang |
| 5,949,811 A | 9/1999 | Baba et al. |
| 5,956,382 A | 9/1999 | Wiener-Avnear et al. |
| 5,960,055 A | 9/1999 | Samarasekera et al. |
| 5,999,587 A | 12/1999 | Ning et al. |
| 6,031,888 A | 2/2000 | Ivan et al. |
| 6,038,283 A | 3/2000 | Carol et al. |
| 6,041,097 A | 3/2000 | Roos et al. |
| 6,052,430 A | 4/2000 | Siochi et al. |
| 6,075,836 A | 6/2000 | Ning |
| 6,078,638 A | 6/2000 | Sauer et al. |
| 6,104,778 A | 8/2000 | Murad |
| 6,104,780 A | 8/2000 | Hanover et al. |
| 6,108,400 A | 8/2000 | Siochi |
| 6,113,264 A | 9/2000 | Watanabe |
| 6,134,296 A | 10/2000 | Siochi |
| 6,142,925 A | 11/2000 | Siochi et al. |
| 6,144,875 A | 11/2000 | Schweikard et al. |
| 6,148,058 A | 11/2000 | Dobbs |
| 6,152,598 A | 11/2000 | Tomisaki et al. |
| 6,200,024 B1 | 3/2001 | Negrelli |
| 6,219,403 B1 | 4/2001 | Nishihara |
| 6,219,441 B1 | 4/2001 | Hu |
| 6,222,901 B1 | 4/2001 | Meulenbrugge et al. |
| 6,240,161 B1 | 5/2001 | Siochi |
| 6,256,366 B1 | 7/2001 | Lai |
| 6,260,005 B1 | 7/2001 | Yang et al. |
| 6,269,141 B1 | 7/2001 | Proksa et al. |
| 6,269,143 B1 | 7/2001 | Tachibana |
| 6,278,766 B1 | 8/2001 | Kooy et al. |
| 6,285,739 B1 | 9/2001 | Rudin et al. |
| 6,292,526 B1 | 9/2001 | Patch |
| 6,307,914 B1 | 10/2001 | Kunieda et al. |
| 6,314,159 B1 | 11/2001 | Siochi |
| 6,318,892 B1 | 11/2001 | Suzuki et al. |
| 6,325,537 B1 | 12/2001 | Watanabe |

(56) References Cited

U.S. PATENT DOCUMENTS

| | | | |
|---|---|---|---|
| 6,325,758 B1 | 12/2001 | Carol et al. |
| 6,330,300 B1 | 12/2001 | Siochi |
| 6,335,961 B1 | 1/2002 | Wofford et al. |
| 6,345,114 B1 | 2/2002 | Mackie et al. |
| 6,349,129 B1 | 2/2002 | Siochi |
| 6,353,222 B1 | 3/2002 | Dotan |
| 6,370,421 B1 | 4/2002 | Williams et al. |
| 6,381,302 B1 | 4/2002 | Berestov |
| 6,385,286 B1 | 5/2002 | Fitchard et al. |
| 6,385,288 B1 | 5/2002 | Kanematsu |
| 6,385,477 B1 | 5/2002 | Werner et al. |
| 6,393,096 B1 | 5/2002 | Carol et al. |
| 6,411,675 B1 | 6/2002 | Llacer |
| 6,429,578 B1 | 8/2002 | Danielsson et al. |
| 6,435,715 B1 | 8/2002 | Betz et al. |
| 6,438,202 B1 | 8/2002 | Olivera et al. |
| 6,445,766 B1 | 9/2002 | Whitham |
| 6,463,122 B1 | 10/2002 | Moore |
| 6,473,490 B1 | 10/2002 | Siochi |
| 6,480,565 B1 | 11/2002 | Ning |
| 6,504,892 B1 | 1/2003 | Ning |
| 6,504,899 B2 | 1/2003 | Pugachev et al. |
| 6,508,586 B2 | 1/2003 | Oota |
| 6,546,073 B1 | 4/2003 | Lee |
| 6,560,311 B1 | 5/2003 | Shepard et al. |
| 6,582,121 B2 | 6/2003 | Crain et al. |
| 6,590,953 B2 | 7/2003 | Suzuki et al. |
| 6,661,870 B2 | 12/2003 | Kapatoes et al. |
| 6,661,872 B2 | 12/2003 | Bova |
| 6,714,620 B2 | 3/2004 | Caflisch et al. |
| 6,735,277 B2 | 5/2004 | McNutt et al. |
| 6,741,674 B2 | 5/2004 | Lee |
| 6,744,848 B2 | 6/2004 | Stanton et al. |
| 6,757,355 B1 | 6/2004 | Siochi |
| 6,760,402 B2 | 7/2004 | Ghelmansarai |
| 6,792,074 B2 | 9/2004 | Erbel et al. |
| 6,813,336 B1 | 11/2004 | Siochi |
| 6,842,502 B2 | 1/2005 | Jaffray et al. |
| 6,850,252 B1 | 2/2005 | Hoffberg |
| 6,852,974 B2 | 2/2005 | Kochi et al. |
| 6,853,705 B2 | 2/2005 | Chang |
| 6,865,254 B2 | 3/2005 | Nafstadius |
| 6,888,919 B2 | 3/2005 | Graf |
| 6,879,659 B2 | 4/2005 | Alber |
| 6,882,702 B2 | 4/2005 | Luo |
| 6,907,105 B2 | 6/2005 | Otto |
| 6,914,959 B2 | 7/2005 | Bailey et al. |
| 6,934,653 B2 | 8/2005 | Ritt |
| 6,937,693 B2 | 8/2005 | Svatos |
| 6,968,035 B2 | 11/2005 | Siochi |
| 6,990,175 B2 | 1/2006 | Nakashima et al. |
| 7,030,386 B2 | 4/2006 | Pang et al. |
| 7,046,762 B2 | 5/2006 | Lee |
| 7,085,348 B2 | 8/2006 | Kamath et al. |
| 7,096,055 B1 | 8/2006 | Schweikard |
| 7,151,258 B2 | 12/2006 | Kochi et al. |
| 7,162,008 B2 | 1/2007 | Earl et al. |
| 7,180,980 B2 | 2/2007 | Nguyen |
| 7,221,733 B1 | 5/2007 | Takai et al. |
| 7,227,925 B1 | 6/2007 | Mansfield et al. |
| 7,329,867 B2 | 2/2008 | Kochi et al. |
| 7,333,591 B2 | 2/2008 | Earl et al. |
| 7,346,144 B2 | 3/2008 | Hughes et al. |
| 7,349,522 B2 | 3/2008 | Yan et al. |
| 7,352,370 B2 | 4/2008 | Wang et al. |
| 7,369,645 B2 | 5/2008 | Lane |
| 7,438,685 B2 | 10/2008 | Burdette et al. |
| 7,471,765 B2 | 12/2008 | Jaffray et al. |
| 7,525,090 B1 | 4/2009 | Krzeczowski |
| 7,556,596 B2 | 7/2009 | Mourtada et al. |
| 7,657,304 B2 | 2/2010 | Mansfield et al. |
| 7,693,683 B2 | 4/2010 | Ihara |
| 7,755,043 B1 | 7/2010 | Gubbens |
| 7,813,822 B1 | 10/2010 | Hoffberg |
| 7,826,592 B2 | 11/2010 | Jaffray et al. |
| 7,831,289 B2 | 11/2010 | Riker et al. |
| 7,872,236 B2 | 1/2011 | Zhang et al. |
| 7,880,154 B2 | 2/2011 | Otto |
| 7,881,772 B2 | 2/2011 | Ghelmansarai |
| 7,906,770 B2 | 3/2011 | Otto |
| 7,907,987 B2 | 3/2011 | Dempsey |
| 7,945,021 B2 | 5/2011 | Shapiro et al. |
| 8,116,430 B1 | 2/2012 | Shapiro et al. |
| 8,696,538 B2 | 4/2014 | Otto |
| 8,788,020 B2 | 7/2014 | Mostafavi et al. |
| 2001/0001807 A1 | 5/2001 | Green |
| 2001/0008271 A1 | 7/2001 | Ikeda et al. |
| 2002/0006182 A1 | 1/2002 | Kim et al. |
| 2002/0066860 A1 | 6/2002 | Possin |
| 2002/0179812 A1 | 12/2002 | Kochi et al. |
| 2003/0007601 A1 | 1/2003 | Jaffray et al. |
| 2003/0086530 A1* | 5/2003 | Otto ............ A61N 5/1042 378/65 |
| 2003/0212325 A1 | 11/2003 | Cortrutz et al. |
| 2003/0219098 A1 | 11/2003 | McNutt et al. |
| 2004/0001569 A1 | 1/2004 | Luo |
| 2004/0022438 A1 | 2/2004 | Hibbard |
| 2004/0071261 A1 | 4/2004 | Earl et al. |
| 2004/0116804 A1 | 6/2004 | Mostafavi |
| 2004/0120452 A1 | 6/2004 | Shapiro et al. |
| 2004/0190680 A1 | 9/2004 | Chang |
| 2004/0254448 A1 | 12/2004 | Amies et al. |
| 2005/0040332 A1 | 2/2005 | Kochi et al. |
| 2005/0061972 A1 | 3/2005 | Kochi et al. |
| 2005/0096515 A1 | 5/2005 | Geng |
| 2005/0111621 A1 | 5/2005 | Riker et al. |
| 2005/0197564 A1 | 9/2005 | Dempsey |
| 2006/0060780 A1 | 3/2006 | Masnaghetti et al. |
| 2006/0176295 A1 | 8/2006 | Toho et al. |
| 2006/0235260 A1 | 10/2006 | Mourtada et al. |
| 2006/0256915 A1 | 11/2006 | Otto et al. |
| 2006/0274061 A1 | 12/2006 | Wang et al. |
| 2006/0274885 A1 | 12/2006 | Wang et al. |
| 2006/0274925 A1 | 12/2006 | West et al. |
| 2006/0289757 A1 | 12/2006 | Kochi et al. |
| 2007/0015991 A1 | 1/2007 | Fu et al. |
| 2007/0034712 A1 | 2/2007 | Kah |
| 2007/0034812 A1 | 2/2007 | Ma |
| 2007/0220108 A1 | 9/2007 | Whitaker |
| 2007/0221842 A1 | 9/2007 | Morokuma et al. |
| 2007/0230770 A1 | 10/2007 | Kulkarni et al. |
| 2007/0242797 A1 | 10/2007 | Stewart et al. |
| 2008/0114564 A1 | 5/2008 | Ihara |
| 2008/0226030 A1 | 9/2008 | Otto |
| 2008/0298550 A1 | 12/2008 | Otto |
| 2008/0317330 A1 | 12/2008 | Takeda et al. |
| 2009/0161827 A1 | 6/2009 | Gertner et al. |
| 2009/0230304 A1 | 9/2009 | Hatano et al. |
| 2009/0297019 A1 | 12/2009 | Zafar et al. |
| 2009/0322973 A1 | 12/2009 | Ito et al. |
| 2010/0020931 A1 | 1/2010 | Otto et al. |
| 2010/0183121 A1 | 7/2010 | Riker et al. |
| 2011/0012911 A1 | 1/2011 | Nakamura et al. |
| 2012/0136677 A1 | 5/2012 | Ziegenhein et al. |

FOREIGN PATENT DOCUMENTS

| | | |
|---|---|---|
| CN | 101014383 | 8/2007 |
| CN | 101247852 | 8/2008 |
| CN | 101422640 | 5/2009 |
| DE | 3828639 A1 | 3/1989 |
| DE | 4223488 A1 | 1/1994 |
| DE | 19800946 A1 | 7/1997 |
| DE | 19614643 A1 | 10/1997 |
| DE | 69319010 T2 | 10/1998 |
| DE | 19931243 A1 | 2/2000 |
| DE | 10139934 A1 | 3/2003 |
| DE | 10305421 A1 | 8/2004 |
| EP | 0062941 A1 | 10/1982 |
| EP | 0062941 B1 | 9/1984 |
| EP | 0205720 A1 | 12/1986 |
| EP | 0471455 A2 | 2/1992 |
| EP | 0480035 A1 | 4/1992 |
| EP | 0480035 B1 | 11/1994 |

(56) References Cited

FOREIGN PATENT DOCUMENTS

| | | |
|---|---|---|
| EP | 0713677 A1 | 5/1996 |
| EP | 0656797 B1 | 9/1998 |
| EP | 0922943 A2 | 6/1999 |
| EP | 0948930 A1 | 10/1999 |
| EP | 0810006 B1 | 8/2000 |
| EP | 1095628 A2 | 5/2001 |
| EP | 0965104 B1 | 9/2001 |
| EP | 0989886 B1 | 9/2004 |
| EP | 0814869 B1 | 12/2004 |
| EP | 1165182 B1 | 3/2005 |
| EP | 0948930 B1 | 9/2007 |
| EP | 1318857 B1 | 7/2008 |
| EP | 1308185 B1 | 12/2010 |
| EP | 1383427 B1 | 3/2011 |
| EP | 1525902 B1 | 4/2015 |
| EP | 1397700 B1 | 7/2015 |
| FR | 2269745 A1 | 11/1975 |
| FR | 2551664 A1 | 3/1985 |
| GB | 1328033 A | 8/1973 |
| JP | 59-76 A | 1/1984 |
| JP | 01-162682 A | 6/1989 |
| JP | 05-057028 A | 3/1993 |
| JP | 06-079006 | 3/1994 |
| JP | 06-339541 | 12/1994 |
| JP | 07-255717 | 10/1995 |
| JP | 09-239044 A | 9/1997 |
| JP | 10-040069 A | 2/1998 |
| JP | 10-113400 | 5/1998 |
| JP | 10-328318 | 12/1998 |
| JP | 63-294839 A | 12/1998 |
| JP | 11-099148 | 4/1999 |
| JP | 11-160440 A | 6/1999 |
| JP | 2000-116638 A | 4/2000 |
| JP | 2000-140137 A | 5/2000 |
| JP | 2000-152927 | 6/2000 |
| JP | 2000-317000 | 11/2000 |
| JP | 2001-029489 A | 2/2001 |
| JP | 2001-029491 | 2/2001 |
| JP | 2001-095793 | 4/2001 |
| JP | 2001-120528 | 5/2001 |
| JP | 2004-097646 | 4/2004 |
| JP | 2004-166975 A | 6/2004 |
| JP | 2004-194697 A | 7/2004 |
| JP | 2008-163575 A | 7/2008 |
| JP | 58-94835 B2 | 3/2016 |
| WO | 1985003212 A1 | 8/1985 |
| WO | 1990014129 A1 | 11/1990 |
| WO | 1992000567 A1 | 1/1992 |
| WO | 92/02277 A1 | 2/1992 |
| WO | 1992020202 A1 | 11/1992 |
| WO | 95/00204 A1 | 1/1995 |
| WO | 97/13552 A1 | 4/1997 |
| WO | 97/42522 A1 | 11/1997 |
| WO | 98/52635 A1 | 11/1998 |
| WO | 99/03397 | 1/1999 |
| WO | 1999048558 A1 | 9/1999 |
| WO | 2000015299 A1 | 3/2000 |
| WO | 2001060236 A2 | 8/2001 |
| WO | 2002013907 A1 | 2/2002 |
| WO | 2002024277 A1 | 3/2002 |
| WO | 02/061680 A2 | 8/2002 |
| WO | 03/008986 A2 | 1/2003 |
| WO | 2003003796 A1 | 1/2003 |
| WO | 2003099380 A1 | 12/2003 |
| WO | 2005057738 A2 | 6/2005 |
| WO | 2007012185 A1 | 2/2007 |

OTHER PUBLICATIONS

Boyer, Arthur L. et al., "A review of electronic portal imaging devices (EPIDs)", Med. Phys., vol. 19, No. 1, Jan./Feb. 1992, pp. 1-16.

Podgorsak, Ervin B. et al., "Dynamic Stereotactic Radiosurgery", Int. J. Radiation Oncology Biol. Phys., vol. 14, No. 1, Jan. 1988, pp. 115-126.

Digital Imaging and Communications in Medicine (DICOM), Supplement 11, Radiotherapy Objects, final text dated Jun. 4, 1997, as a supplement to the DICOM Standard, and an extension to Parts 3, 4, and 6 of the published DICOM Standard.

Tobler, M. et al., "The Application of Dynamic Field Shaping and Dynamic Dose Rate Control in Conformal Rotational Treatment of the Prostate," Medical Dosimetry, vol. 27, No. 4, 2002, pp. 251-254.

Jaffray, D. et al., "Performance of a Volumetric CT Scanner Based Upon a Flat-Panel Imager," SPIE Conference on Physics of Medical Imaging, Feb. 1999, pp. 204-214, San Diego, California.

Jaffray, D.A. et al., "Flat-Panel Cone-Beam CT on a Mobile Isocentric C-Arm for Image-Guided Brachytherapy," Medical Imaging 2002: Physics of Medical Imaging, Proceedings of SPIE, vol. 4682, 2002, pp. 209-217.

Jaffray, D. et al., "Cone-beam computed tomography with a flat-panel imager: Initial performance characterization," Med. Phys., vol. 27, No. 6, Jun. 2000, pp. 1311-1323.

Jaffray, D. et al., "A Radiographic and Tomographic Imaging System Integrated into a Medical Linear Accelerator for Localization of Bone and Soft-Tissue Targets," Int. J. Radiation Oncology Biol. Phys., vol. 45, No. 3, 1999, pp. 773-789.

Siewerdsen, J. et al., "Cone-Beam CT with a Flat-Panel Imager: Noise Considerations for Fully 3-D Computed Tomography," Medical Imaging 2000: Physics of Medical Imaging, Proceedings of SPIE, vol. 3977, 2000, pp. 408-416.

Siewerdsen, J. et al., "Optimization of x-ray imaging geometry (with specific application to flat-panel cone-beam computed tomography)," Med. Phys., vol. 27, No. 8, Aug. 2000, pp. 1903-1914.

Yan, D. et al., "Adaptive Modification of Treatment Planning to Minimize the Deleterious Effects of Treatment Setup Errors," Int. J. Radiation Oncology Biol. Phys., vol. 38, No. 1, Nov. 1, 1997, pp. 197-206.

Yu, C., "Intensity Modulated Arc Therapy: Technology and Clinical Implementation," Sep. 1995, pp. 1-14.

Chin, L. et al., "Dose Optimization with Computer-Controlled Gantry Rotation, Collimator Motion and Dose-Rate Variation," Int. J. Radiation Oncology Biol. Phys., vol. 9, No. 5, May 1983, pp. 723-729.

Cotrutz, C. et al., "Intensity modulated arc therapy (IMAT) with centrally blocked rotational fields," Phys. Med. Biol., vol. 45, 2000, pp. 2185-2206.

Duthoy, W. et al., "Clinical Implementation of Intensity-Modulated Arc Therapy (IMAT) for Rectal Cancer," Int. J. Radiation Oncology Biol. Phys., vol. 60, No. 3, 2004, pp. 794-806.

Duthoy, W. et al., "Whole Abdominopelvic Radiotherapy (WAPRT) Using Intensity-Modulated Arc Therapy (IMAT): First Clinical Experience," Int. J. Radiation Oncology Biol. Phys., vol. 57, No. 4, 2003, pp. 1019-1032.

Bortfeld, T. et al., "Clinically relevant intensity modulation optimization using physical criteria," In Proceedings of the XII International Conference on the Use of Computers in Radiation Therapy, Salt Lake City, Utah, 1-4 (1997).

Yan, D. et al., "Computed tomography guided management of interfractional patient variation", Semin. Radiat, Oncol. 15, 168-179 (2005).

Court, L. et al., "An automatic CT-guided adaptive radiation therapy technique by on-line modification of Multileaf Collimator leaf positions for prostate cancer", Int. J. Radiat. Oncol., Biol., Phys. 62(1), 154-163 (2005).

Mohan, R. et al., "Use of deformed intensity distributions for on-line modification of image-guided IMRT to account for interfractional anatomic changes", Int. J. Radiat. Oncol., Biol., Phys. 61(4), 1258-1266 (2005).

Mackie, T.R. et al., "Image guidance for precise conformal radiotherapy", Int. J. Radiat. Oncol., Biol., Phys. 56(1), 89-105 (2003).

Brock, K.K. et al., "Feasibility of a novel deformable image registration technique to facilitate classification, targeting, and monitoring of tumor and normal tissue", Int. J. Radiat. Oncol., Biol., Phys. 64(4), 1245-1254 (2006).

(56) References Cited

OTHER PUBLICATIONS

Davis, B.C. et al., "Automatic segmentation of intra-treatment CT images for adaptive radiation therapy of the prostate", Med. Image Comput. Comput. Assist. Interv. Int. Conf. Med. Image. Comput. Comput. Assist Interv. 8(Pt 1), (2005).
Foskey, M., "Large deformation three-dimensional image registration in image-guided radiation therapy", Phys. Med. Biol. 50(24), 5869-5892 (Dec. 7, 2005).
Munbodh, R. et al., "Automated 2D-3D registration of a radiograph and a cone beam CT using line-segment enhancement", Med. Phys. 33(5), 1398-1411 (Apr. 27, 2006).
Court, L.E. et al., "Automatic online adaptive radiation therapy techniques for targets with significant shape change: A feasibility study", Phys. Med. Biol. 51(10), 2493-2501 (Apr. 27, 2006).
Godfrey, D.J. et al., "Digital tomosynthesis with an on-board kilovoltage imaging device", Int. J. Radiat. Oncol., Biol., Phys. 65(1), 8-15 (2006).
Mestrovic, A. et al., "Direct aperture optimization for online adaptive radiation therapy", Med. Phys. 34(5), Apr. 19, 2007, pp. 1631-1646.
Cortrutz, C. et al., "Segment-based dose optimization using a genetic algorithm", Phys. Med. Biol. 48(18), 2987-2998 (2003).
Bedford, J.L. et al., "Constrained segment shapes in direct-aperture optimization for step-and shoot IMRT", Med. Phys. 33(4). 944-958 (Mar. 17, 2006).
Kirkpatrick, S. et al., "Optimization by simulated annealing", Science 220, 671-680 (1983).
I.M.R.T.C.W. Group, "Intensity-modulated radiotherapy: Current status and issues of interest", Int. J. Radiat. Oncol., Biol., Phys. 51(4), 880-914 (2001).
Niemierko, A. et al., "Random sampling for evaluation treatment plans", Med. Phys. 17(5), 753-762 (1990).
Chui, C.S. et al., "Dose calculation for photon beams with intensity modulation generated by dynamic jaw or multileaf collimations", Med. Phys, 21(8), 1237-1244 (1994).
Ghilezan, M.J. et al., "Prostate gland motion assessed with cine-magnetic resonance imaging (cine-MRI)", Int. J. Radiat. Oncol., Biol., Phys. 62(2), 406-417 (2005).
Nichol, A.M. et al., "Intra-prostatic fiducial markers and concurrent androgen deprivation", Clin. Oncol. (R Coll. Radiol) 17(6), 465-468 (2005).
Zellars, R.C. et al., "Prostate position late in the course of external beam therapy: Patterns and predictors", Int. J. Radiat. Oncol., Biol., Phys. 47(3), 655-660 (2000).
Sanguineti, G. et al., "Neoadjuvant androgen deprivation and prostate gland shrinkage during conformal radiotherapy", Radiother. Oncol. 66(2), 151-157 (2003).
Nichol, A.M. et al., "A magnetic resonance imaging study of prostate deformation relative to implanted gold fiducial markers", Int. J. Radiat. Oncol., Biol., Phys. 67(1), 48-56 (2007).
Yan, D. et al., "The influence of interpatient and intrapatient rectum variation on external beam treatment of prostate cancer", Int. J. Radiat. Oncol., Biol., Phys. 51(4), 1111-1119 (2001).
Hoogeman, M.S. et al., "A model to simulate day-to-day variations in rectum shape", Int. J. Radiat. Oncol., Biol., Phys. 54(2), 615-625 (2002).
Jiang, Z. et al., "An examination of the number of required apertures for step-and-shoot-IMRT", Phys. Med. Biol. 50 (23), 5653-5663 (Nov. 24, 2005).
Earl, M.A. et al., "Inverse Planning for Intensity-Modulated Arc Therapy Using Direct Aperture Optimization", Physics in Medicine and Biology 48 (2003), Institute of Physics Publishing, pp. 1075-1089.
Spirou, S. et al., "A Gradient Inverse Planning Algorithm with Dose-Volume Contraints", Med. Phys. 25, pp. 321-333 (1998).
Wu, Q. et al., "Algorithm and Functionality of an Intensity Modulated Radiotherapy Optimization System", Med. Phys. 27, pp. 701-711 (2000).

Spirou, S. et al., "Generation of Arbitrary Intensity Profiles by Dynamic Jaws or Multileaf Collimators", Med. Phys. 21, pp. 1031-1041 (1994).
Xia, P. et al., "Multileaf Collimator Leaf Sequencing Algorithm for Intensity Modulated Beams with Multiple Static Segments", Med. Phys. 25, pp. 1424-1434 (1998).
Otto, K. et al., "Enhancement of IMRT Delivery through MLC Rotation", Phys. Med. Biol. 47, 3997-4017 (2002).
Shepard, D.M. et al., "Direct Aperture Optimization: A Turnkey Solution for Step-and-Shoot IMRT", Med. Phys. 29 (6) (2002), pp. 1007-1018.
Tervo, J. et al., "A Model for the Control of a Multileaf Collimator in Radiation Therapy Treatment Planning", Inverse Problems 16 (2000), pp. 1875-1895.
Shepard, D.M. et al., "An Arc-Sequencing Algorithm for Intensity Modulated Arc Therapy", Med. Phys. 34 (2) (2007), pp. 464-470.
Cao, D. et al., "Continuous Intensity Map Optimization (CIMO): A Novel Approach to Leaf Sequencing in Step and Shoot IMRT", Med. Phys. 33 (4) (2006), pp. 859-867.
Ulrich, S. et al., "Development of an Optimization Concept for Arc-Modulated Cone Beam Therapy", Phys. Med. Biol. 52 (2007), pp. 4099-4119.
Hardemark, B. et al., "Direct Machine Parameter Optimization with RayMachine in Pinnacle", RaySearch White Paper, RaySearch Laboratories (2003).
Yu, C.X., "Intensity-modulated arc therapy with dynamic multileaf collimation: An alternative to tomotherapy," Phys. Med. Biol. 40, pp. 1435-1449, 1995.
Gladwish, A. et al., "Segmentation and leaf sequencing for intensity modulated arc therapy," Med. Phys. 34, pp. 1779-1788, 2007.
Wong, E. et al., "Intensity-modulated arc therapy simplified," Int. J. Radiat. Oncol. Biol. Phys. 53, pp. 222-235, 2002.
Bratengeier, K., "2-Step IMAT and 2-Step IMRT in three dimensions," Med. Phys. 32, pp. 3849-3861, 2005.
Cameron, C., "Sweeping-window arc therapy: An implementation of rotational IMRT with automatic beam-weight calculation," Phys. Med. Biol. 50, pp. 4317-4336, 2005.
Crooks, S.M. et al., "Aperture modulated arc therapy," Phys. Med. Biol. 48, pp. 1333-1344, 2003.
De Gersem, W. et al., "Leaf position optimization for step-and-shoot IMRT," Int. J. Radiat. Oncol. Biol. Phys. 51, pp. 1371-1388, 2001.
Milette, M.P. et al., "Maximizing the potential of direct aperture optimization through collimator rotation," Med. Phys. 34, pp. 1431-1438, 2007.
Wu, Q. et al., "Dynamic Splitting of Large Intensity-Modulated Fields," Phys. Med. Biol. 45 (2000), Richmond, VA, USA, p. 1731-1740.
Verfaillie, G. et al., "Russian Doll Search for Solving Constraint Optimization Problems," AAAI-96 Proceedings, 1996, p. 181-187.
"New Gating System from BrainLAB Enables Breakthrough in the Radiotherapy Treatment of Lung and Liver Patients," Sep. 28, 2004, 4 pages.
Yu, C. et al., "A multiray model for calculating electron pencil beam distribution," Med. Phys., vol. 15, 1988, pp. 662-671.
Yu, C., "Photon dose perturbations due to small inhomogeneities," Med. Phys., vol. 14, No. 1, Jan./Feb. 1987, pp. 78-83.
Yu, C., "Photon does calculation incorporating explicit electron transport," Med. Phys., vol. 22, No. 7, Jul. 1995, pp. 1157-1166.
Mosleh-Shirazi, M. et al., "Optimization of the scintillation detector in a combined 3D megavoltage CT scanner and portal imager," Med. Phys., vol. 25, No. 10, Oct. 1998, pp. 1880-1890.
Advanced Workstation for Irregular Field Simulation and Image Matching, MDS Nordion, 1999, 7 pages.
Andrew, J.W. et al., "A video-Based Patient Contour Acquisition System for the Design of Radiotherapy Compensators," Med. Phys., vol. 16, 1989, pp. 425-430.
Balter, James M. et al., "Daily Targeting of Intrahepatic Tumors for Radiotherapy," Int. J. Radiation Oncology Biol. Phys., vol. 52, No. 1, 2002, pp. 266-271.
Brewster et al., "Automatic generation of beam apertures," Med. Phys., vol. 20, No. 5, Sep./Oct. 1993, pp. 1337-1342.
Cho, Paul S. et al., Cone-Beam CT for Radiotherapy Applications, Phys. Med. Biol., vol. 40, 1995, pp. 1863-1883.

(56) References Cited

OTHER PUBLICATIONS

Drake, D.G. et al., "Characterization of a Fluoroscopic Imaging System for kV and MV Radiography," Med. Phys., vol. 27, No. 5, May 2000, pp. 898-905.

Elliott, P.J., et al., "Interactive image segmentation for radiation treatment planning," IBM Systems Journal, vol. 31, No. 4, 1992, pp. 620-634.

Fahrig et al., "Three-Dimensional Computed Tomographic Reconstruction Using a C-Arm Mounted XRII: Image-Based Correction of Gantry Motion Nonidealities," Med. Phys., vol. 27, No. 1, Jan. 2000, pp. 30-38.

Feldkamp, L.A. et al., "Practical Cone-Beam Algorithm," J. Opt. Soc. Am. A., vol. 1, No. 6, Jun. 1984, pp. 612-619.

Gademann, G. et al., "Dreidimensionale Bestrahlungsplanung. Untersuchen zur Klinischen Integration," Strahlenther. Onkol., vol. 169, No. 3, 1993, pp. 159-167.

Groh, B.A., et al., "A Performance Comparison of Flat-Panel Imager-Based MV and kV Cone-beam CT," Med. Phys., vol. 29, No. 6, Jun. 2002, pp. 967-975.

Siewerdsen, J.H. et al., "A ghost story: spatio-temporal response characteristics of an indirect-detection flat-panel imager," Med. Phys., vol. 26, No. 8, Aug. 1999, pp. 1624-1641.

Jaffray, D.A. et al., "A Radiographic and Tomographic Imaging System Integrated into a Medical Linear Accelerator for Localization of Bone and Soft-Tissue Targets," Int. J. Radiation Oncology Biol. Phys., vol. 45, No. 3, 1999, pp. 773-789.

Jaffray, D.A. et al., "Cone-beam CT: applications in image-guided external beam radiotherapy and brachytherapy," Proceedings of the 22nd Annual EMBS International Conference, Jul. 23-28, 2000, p. 2044, Chicago, IL.

Keys, D. et al., "A CCTV-Microcomputer Biostereometric System for Use in Radiation Therapy", Aug. 1984, p. 133 pages, Washington University Department of Physics, St. Louis, MS.

Kudo, H. et al., "Feasible Cone Beam Scanning Methods for Exact Reconstruction in Three-Dimensional Tomography," J. Opt. Soc. Am. A., vol. 7, No. 12, Dec. 1990, p. 2169-2183.

Kuhn, M.H., "AIM Project A2003: Computer Vision in RAdiology (COVIRA)," Computer Methods and Programs in Biomedicine, vol. 45, Oct. 1994, pp. 17-31.

Kushima, T. et al., "New development of integrated CT simulation system for radiation therapy planning," Kobe J. Med. Sci., vol. 39, Dec. 1993, pp. 197-213.

Masshiro, E. et al., "Patient Beam Positioning System Using CT Images," Phys. Med. Biol., vol. 27, No. 2, 1982, pp. 301-305.

Midgley, S. et al., "A Feasibility Study for Megavoltage Cone Beam CT Using a Commercial EPID," Phys. Med. Biol., vol. 43, 1998, pp. 155-169.

Mohan, R. et al., "Intersection of shaped radiation beams with arbitrary image sections," Computer Mehods and Programs in Biomedicine, vol. 24, Jun. 1987, pp. 161-168.

Nakagawa, M.D., Keiichi et al., "Megavoltage CT-Assisted Stereotactic Radiosurgery for Thoracic Tumors: Original Research in the Treatment of Thoracic Neoplasms," Int. J. Radiation Oncology Biol. Phys., vol. 48, No. 2, 2000, pp. 449-457.

Ning, R. et al., "Flat Panel Detector-Based Cone-Beam Volume CT Angiography Imaging: System Evaluation," IEEE Transactions on Medical Imaging, vol. 19, No. 9, Sep. 2000, pp. 949-963.

Ning, R. et al., "Image Intensifier-Based Volume Tomographic Angiography Imaging System: Work in Progress," SPIE, vol. 2708, 1996, p. 328-339.

United States Patent and Trademark Office, "Office Action" dated Sep. 18, 2012 in co-pending U.S. Appl. No. 13/043,892, filed Mar. 9, 2011, entitled "Methods and Apparatus for the Planning and Delivery of Radiation Treatments", Sep. 18, 2012.

Pisani, Laura, M.S. et al., "Setup Error in Radiotherapy: On-line Correction Using Electronic Kilovoltage and Megavoltage Radiographs," Int. J. Radiation Oncology Biol. Phys., vol. 47, No. 3, 2000, pp. 825-839.

Ragan, D. et al., "Correction for Distortion in a Beam Outline Transfer Device in Radiotherapy CT-Based Simulation," Med. Phys., vol. 20, 1993, pp. 179-185.

Reynolds, R.A. et al., "An algorithm for three-dimensional visualization of radiation therapy beams," Med. Phys., vol. 15, No. 24, 1988, pp. 24-28.

Rizo et al., "Comparison of two three-dimensional x-ray cone-beam-reconstruction algorithms with circular source trajectories," J. Opt. Soc. Am. A., vol. 8, No. 10, Oct. 1991, p. 1639-1648.

Ruchala, K.J. et al., "Megavoltage CT on a Tomotherapy System," Phys. Med. Biol., vol. 44, 1999, pp. 2597-2621.

Siewerdsen, J.H. et al., "Optimization of X-Ray Imaging Geometry (With Specific Application to Flat-Paneled Cone-Beam Computed Tomography)," Med. Phys., vol. 27, No. 8, Aug. 2000, pp. 1903-1914.

Siewerdsen, Jeffery H. et al., "Cone-Beam Computed Tomography With a Flat:Panel Imager: Magnitude and Effects of X-Ray Scatter," Med. Phys., vol. 28, No. 2, Feb. 2001, pp. 220-231.

Swindell, William et al., "Computed Tomography With a Linear Accelerator With Radiotherapy Applications," Med. Phys., vol. 10, No. 4, Jul./Aug. 1983, pp. 416-420.

Uematsu, M. et al., "A Dual Computed Tomography Linear Accelerator Unit for Stereotactic Radiation Therapy: A New Approach Without Cranially Fixated Stereotactic Frames," Int. J. Radiation Oncology, vol. 35, No. 3, 1996, pp. 587-592.

Uematsu, M. et al., "Daily Positioning Accuracy of Frameless Stereotactic Radiation Therapy with a Fusion of Computed Tomography and Linear Accelerator (FOCAL) Unit: Evaluation of Z-axis with a Z-marker," Radiotherapy and Oncology, vol. 50, Mar. 1999, pp. 337-339.

Uematsu, M. et al., "Infractional Tumor Position Stability During Computed Tomography (CT)-Guided Frameless Seterotactic Radiation Therapy for Lung or Liver cancers with a Fusion of CT and Linear Accelerator (FOCAL) Unit," Int. J. Radiation Oncology Biol. Phys., vol. 48, No. 2, 2000, pp. 443-448.

European Patent Office, "Communication pursuant to Article 94(3) EPC," EP Application No. 03786979.9-1657, dated Jan. 30, 2014, 8 pages.

Yan, X. et al., "Derivation and analysis of a filtered backprojection algorithm for cone beam projection data," IEEE Transactions on Medical Imaging, vol. 10, No. 3, Sep. 1991, pp. 462-472.

Wong, E. et al., "Intensity-Modulated Arc Therapy for Treatment of High-Risk Endometrial Malignancies," Int. J. Oncology Biol. Phys, vol. 61, No. 1, 2005, pp. 830-841.

Ma, L. et al., "Optimized Intensity-modulated Arc Therapy for Prostate Cancer Treatment," Int. J. Cancer (Radiat. Oncol. Invest), vol. 96, 2001, pp. 379-384.

Neicu, T. et al., "Synchronized moving aperture radiation therapy (SMART): average tumour trajectory for lung patients," Phys. Med. Biol., vol. 48, 2003, pp. 587-598.

Woudstra, E. et al., "Automated selection of beam orientations and segmented intensity-modulated radiotherapy (IMRT) for treatment of oesophagus tumors," Radiotherapy and Oncology, vol. 77, 2005, pp. 254-261.

Yu, C. et al. "Clinical Implementation of Intensity-Modulated Arc Therapy," Int. J. Radiation Oncology Biol. Phys, vol. 53, No. 2, 2002, pp. 453-463.

Hilbig, Matthias, "Inverse Bestrahlungsplanung fuer intensitaetsmodulierte Strahlenfelder mit Linearer Programmierung als Optimierungsmethode," Feb. 20, 2003, 156 pages.

Hilbig, Matthias, et al., "Entwicklung eines inversen Bestrahlungsplanungssystems mit linearer Optimierung," 2002, v. 12, pp. 89-96.

Baer, Werner, et al., "Fluenzmodulierte Strahlentherapie mit in die Optimierung integrierter Segmentierung," Z. Med. Phys., vol. 13, 2003, v. 13, pp. 12-15.

Klepper, L. et al., "Methods of mathematical simulation and planning of fractionated irradiation of malignant tumors," 2000, v. 2, pp. 73-79.

Nakagawa, T. et al., "Accuracy improvement of irradiation position and new trend," 2001, pp. 102-105.

Nishiki, M., "X-ray detector in IT era—FPD : Flat Panel Detector," Nishiki M., 2001, pp. 1-2.

(56) References Cited

OTHER PUBLICATIONS

Watanabe, Y. "Development of corn beam X-ray CT system," Oct. 2002, pp. 778-783.
Weissbluth, M. et al., "The Stanford medical linear accelerator. II. Installation and physical measurements," Feb. 1959, pp. 242-253.
Biggs, P.J. et al., "A diagnostic X ray field verification device for a 10 MV linear accelerator," Int. J. Radiation Oncology Biol. Phys, vol. 11, No. 3, Mar. 1985, pp. 635-643.
Akanuma, A. et al., "New Patient Set Up in Linac-CT Radiotherapy System—First Mention of a Hybrid CT-Linac System," 1984, pp. 465-467.
Uematsu, M. et al., "A dual computed tomography linear accelerator unit for stereotactic radiation therapy: a new approach without cranially fixated stereotactic frames," Int. J. Radiation Oncology Biol. Phys, vol. 35, No. 3, Jun. 1, 1996, pp. 587-592.
Mackie, T.R. et al., "Tomotherapy: a new concept for the delivery of dynamic conformal radiotherapy," Med. Phys., vol. 20, No. 6, Nov./Dec. 1993, pp. 1709-1719.
Schewe, J.E. et al., "A room-based diagnostic imaging system for measurement of patient setup," Med. Phys., vol. 25, No. 12, Dec. 1998, pp. 2385-2387.
Antonuk, L. et al., "Initial Performance Evaluation of an Indirect-Detection, Active Matrix Flat-Panel Imager (AMFPI) Prototype for Megavoltage Imaging," Int. J. Radiation Oncology Biol. Phys, vol. 42, No. 2, 1998, pp. 437-452.
Antonuk, L. et al., "Megavoltage Imaging with a Large-Area, Flat-Panel, Amorphous Silicon Imager," Int. J. Radiation Oncology Biol. Phys, vol. 36, No. 3, 1996, pp. 661-672.
Antonuk, L. et al., "A Real-Time, Flat-Panel, Amorphous Silicon, Digital X-ray Imager," Int. J. Radiation Oncology Biol. Phys, vol. 15, No. 4, Jul. 1995, pp. 993-1000.
Antonuk, L. et al., "Strategies to improve the signal and noise performance of active matrix, flat-panel imagers for diagnostic x-ray applications," Med. Phys., vol. 27, No. 2, Feb. 2000, pp. 289-306.
Bassett, P., "An Interactive Computer System for Studying Human Mucociliary Clearance," Comput. Biol. Med., vol. 9, 1979, pp. 97-105.
Bissonnette, J. et al., "Optimal radiographic magnification for portal imaging," Med. Phys., vol. 21, No. 9, Sep. 1994, pp. 1435-1445.
Boyer, A. et al., "Intensity-Modulated Radiotherapy: Current Status and Issues of Interest," Int. J. Radiation Oncology Biol. Phys, vol. 51, No. 4, 2001, pp. 880-914.
Boyer, A. et al., "A review of electronic portal imaging devices," Med. Phys., vol. 19, No. 1, Jan./Feb. 1992, pp. 1-16.
Brown, A. et al., "Three-Dimensional Photon Treatment Planning for Hodgkin's Disease," Int. J. Radiation Oncology Biol. Phys, vol. 21, No. 1, May 15, 1991, pp. 205-215.
Cheng, A. et al., "Systematic verification of a three-dimensional electron beam dose calculation algorithm," Med. Phys., vol. 23, No. 5, May 1996, pp. 685-693.
Cullity, B., "Elements of X-Ray Diffraction," second edition, 1978, pp. 6-12, Addison-Wesley Publishing Company, Inc.
Dieu, L. et al., "Ion Beam Sputter-Deposited SiN/TiN Attenuating Phase-Shift Photoblanks," Proc. SPIE, vol. 4186, 2001, pp. 810-817.
Du, M. et al., "A Multileaf Collimator Field Prescription Preparation System for Conventional Radiotherapy," Int. J. Radiation Oncology Biol. Phys, vol. 30, No. 3, 1994, pp. 707-714.
Du, M. et al., "A Multileaf Collimator Field Prescription Preparation System for Conventional Radiotherapy," Int. J. Radiation Oncology Biol. Phys, vol. 32, No. 2, 1995, pp. 513-520.
El-Mohri, Y. et al., "Relative dosimetry using active matrix flat-panel imager (AMFPI) technology," Med. Phys., vol. 26, No. 8, Aug. 1999, pp. 1530-1541.
Ezz, A. et al., "Daily Monitoring and Correction of Radiation Field Placement Using a Video-Based Portal Imaging System: A Pilot Study," Int. J. Radiation Oncology Biol. Phys, vol. 22, No. 1, 1992, pp. 159-165.

Frazier, A. et al., "Dosimetric Evaluation of the Conformation of the Multileaf Collimator to Irregularly Shaped Fields," Int. J. Radiation Oncology Biol. Phys, vol. 33, No. 5, 1995, pp. 1229-1238.
Frazier, A. et al., "Effects of Treatment Setup Variation on Beam's Eye View Dosimetry for Radiation Therapy Using the Multileaf Collimator vs. the Cerrobend Block," Int. J. Radiation Oncology Biol. Phys, vol. 33, No. 5, 1995, pp. 1247-1256.
Graham, M. et al., "A Method to Analyze 2-Dimensional Daily Radiotherapy Portal Images from an On-Line Fiber-Optic Imaging System," Int. J. Radiation Oncology Biol. Phys, vol. 22, No. 3, Mar. 1991, pp. 613-619.
Halverson, K. et al., "Study of Treatment Variation in the Radiotherapy of Head and Neck Tumors Using a Fiber-Optic On-Line Radiotherapy Imaging System," Int. J. Radiation Oncology Biol. Phys, vol. 21, No. 5, 1991, pp. 1327-1336.
Harms, W. et al., A software tool for the quantitative evaluation of 3D dose calculation algorithms, Med. Phys., vol. 25, No. 10, Oct. 1998, pp. 1830-1836.
Herman, M. et al., "Clinical use of electronic portal imaging: Report of AAPM Radiation Therapy Committee Task Group 58," Med. Phys., vol. 28, No. 5, May 2001, pp. 712-737.
Jaffray, D. et al., "Activity distribution of a cobalt-60 teletherapy source," Med. Phys., vol. 18, No. 2, Mar./Apr. 1991, pp. 288-291.
Jaffray, D. et al., "Conebeam Tomographic Guidance of Radiation Field Placement for Radiotherapy of the Prostate," Int. J. Radiation Oncology Biol. Phys, 1998, pp. 1-32.
Jaffray, D. et al., "Dual-Beam Imaging for Online Verification of Radiotherapy Field Placement," Int. J. Radiation Oncology Biol. Phys, vol. 33, No. 5, 1995, pp. 1273-1280.
Jaffray, D. et al., "Exploring "Target of the Day" Strategies for a Medical Linear Accelerator With Conebeam-CT Scanning Capability," XII Inernational Conference on the Use of Computers in Radiation Therapy, May 27-30, 1997, pp. 172-174.
Jaffray, D. et al., "Managing Geometric Uncertainty in Conformal Intensity-Modulated Radiation Therapy," Seminars in Radiation Oncology, vol. 9, No. 1, Jan. 1999, pp. 4-19.
Jaffray, D., "X-ray scatter in megavoltage transmission radiography: Physical characteristics and influence on image quality," Med. Phys., vol. 21, No. 1, Jan. 1994, pp. 45-60.
Jaffray, D. et al., "X-ray sources of medical linear accelerators: Focal and extra-focal radiation," Med. Phys., vol. 20, No. 5, Sep./Oct. 1993, pp. 1417-1427.
Canadian Intellectual Property Office; International Search Report and Written Opinion for PCT/CA2011/050385 dated Nov. 24, 2011; 11 pages.
Pardo-Montero et al.; An Approach to Multiobjective Optimization of Rotational Therapy; Med. Phys. 36(7); Jul. 2009; pp. 3292-3303.
Chanyavanich et al.; Knowledge-based IMRT Treatment Planning for Prostate Cancer; Med. Phys. 38(5); May 2011; pp. 2515-2522.
Craft et al.; Multicriteria VMAT Optimization; Med. Phys. 39(2); Feb. 2012; pp. 686-696.
Cotrutz et al.; Using Voxel-dependent Importance Factors for Interactive DVH-based Dose Optimization; Phys. Med. Biol. 47; (2002); pp. 1659-1669.
Cotrutz et al.; IMRT Dose Shaping With Regionally Variable Penalty Scheme; Med. Phys. 30(4); Apr. 2003; pp. 544-551.
File History of Otto U.S. Pat. No. 7,880,154, issued Feb. 1, 2011, entitled Methods and Apparatus for the Planning and Delivery of Radiation Treatments.
File History of Otto U.S. Pat. No. 7,906,770, issued Mar. 15, 2011, entitled Methods and Apparatus for the Planning and Delivery of Radiation Treatments.
File History of Otto U.S. Pat. No. 8,658,992, issued Feb. 25, 2014, entitled Methods and Apparatus for the Planning and Delivery of Radiation Treatments.
File History of Otto U.S. Pat. No. 8,696,538, issued Apr. 15, 2014, entitled Methods and Apparatus for the Planning and Delivery of Radiation Treatments.
File History of Otto U.S. Pat. No. 9,050,459, issued Jun. 9, 2015, entitled Methods and Apparatus for the Planning and Delivery of Radiation Treatments.

(56) References Cited

OTHER PUBLICATIONS

Petition for Inter Partes Review of U.S. Pat. No. 7,906,770, *Elekta Inc.*, Petitioner v. *Varian Medical Systems, Inc. and Varian Medical System International AG*, Patent Owner, filed Apr. 4, 2016.
Petition for Inter Partes Review of U.S. Pat. No. 7,906,770, *Elekta Inc.*, Petitioner v. *Varian Medical Systems, Inc. and Varian Medical System International AG*, Patent Owner, filed Apr. 5, 2016.
Petition for Inter Partes Review of U.S. Pat. No. 7,880,154, *Elekta Inc.*, Petitioner v. *Varian Medical Systems, Inc. and Varian Medical System International AG*, Patent Owner, filed Apr. 5, 2016.
Petition for Inter Partes Review of U.S. Pat. No. 8,696,538, *Elekta Inc.*, Petitioner v. *Varian Medical Systems, Inc. and Varian Medical System International AG*, Patent Owner, filed Apr. 5, 2016.
J. Gordon et al.; Coverage Optimized Planning: Probabilistic Treatment Planning Based on Dose Coverage Histogram Criteria; Medical Physics, AIP; Melville, NY, US; vol. 37, No. 2, Jan. 12, 2010; pp. 550-563; XP012135578; ISSN: 0094-2405; DOI: 10.1118/1.3273063.
Rostkowska, J. et al., "Physical and Dosimetric Aspects of Quality Assurance in Stereotactic Radiotherapy", Rep. Pract. Oncol. Radiother., vol. 6, No. 1, 2001, p. 53-54.
Malik, R. et al., "Simulator Based CT: 4 Years of Experience at the Royal North Shore Hospital", 3D Radiation Treatment Planning and Conformal Therapy, Proceedings of an International Symposium, Apr. 21-23, 1993, p. 177-185, Sydney, Australia.
Sidhu, K. et al., "Optimization of Conformal Thoracic Radiotherapy Plans While Using Cone-Beam CT Imaging for Treatment Verification", Proceedings of the 43rd Annual ASTRO meeting, 2001, p. 175-176.
Johnsen, S. et al., "Improved Clinac Electron Beam Quality", Medical Physics, Sep./Oct. 1983, vol. 10, No. 5, p. 737.
Wong, J. et al., "Initial clinical experience with a gantry mounted dual beam imaging system for setup error localization", L.J. Radiation Oncology Biology Physics, vol. 42, No. 1 Supplement, 1998, p. 138.
Simo Muinonen, "Sädehoidon valmistelun optimointi fysiikan keinoin", 1995, p. 1-166.
Pekka Kolmonen, "The direct control of the Multi-Leaf Collimator in the inverse problem of radiotherapy treatment planning", Mar. 19, 2004, p. 1-81.
Jyrki Alakuijala, "Algorithms for modeling anatomic and target volumes in image-guided neurosurgery and radiotherapy", 2001, p. 1-121.
Heikki Joensuu, "Intensiteettimuokattu sädehoito—uusi tekniikka parantanee hoitotuloksia", 2001, p. 389-394.
Tiina Seppala, "FIR 1 epithermal neutron beam model and dose calculation for treatment planning in neutron capture therapy", 2002, p. 1-46.
Maria Korteila, "Varianin avulla Säde tappaa kasvaimen tarkasti", 2000, p. 1-8.
Arnfield et al., "The use of film dosimetry of the penumbra region to improve the accuracy of intensity modulated radiotherapy", Medial Physics, vol. 32, No. 12, Jan. 2005, p. 12-18.
Bergman et al., "The use modified single pencil beam dose kernels to improve IMRT dose calculation accuracy", Medial Physics, vol. 31, No. 12, Dec. 2004, p. 3279-3287.
Budgell, "Temporal resolution requirements for intensity modulated radiation therapy delivered by multileaf collimators", Phys. Med. Biol., vol. 44, 1999, p. 1581-1596.
Xing et al., "Dosimetric verification of a commercial inverse treatment planning system", Phys. Med. Biol., vol. 44, 1999, p. 463-478.
Preciado-Walters et al., "A coupled col. generation, mixed integer approach to optimal planning of intensity modulated radiation therapy for cancer", Math. Program, Ser. B 101, 2004, p. 319-338.
Johan Löf, "Development of a general framework for optimization of radiation therapy", 2000, p. 1-140.
Xing et al., "Iterative methods for inverse treatment planning", Phys. Med. Biol., vol. 41, 1996, p. 2107-2123.

Podgorsak et al., "Dynamic Stereotactic Radiosurgery", 1988, p. 115-126.
Webb et al., "Inverse planning with constraints to generate smoothed intensity-modulated beams", Phys. Med. Biol., vol. 43, 1998, p. 2785-2794.
Crooks et al., "Linear algebraic methods applied to intensity modulated radiation therapy", Phys. Med. Biol., vol. 46, 2001, p. 2587-2606.
Varian Medical Systems, Radiation Therapy Acuity, 2005, 1 page.
Anderson, R., "Software system for automatic parameter logging on Philips SL20 linear accelerator", Med. & Biol. Eng. & Comput., vol. 33, 1995, p. 220-222.
Jaffray, et al., "Cone-beam computed tomography on a medical linear accelerator using a flat-panel imager", ICCR, 2000, p. 558-560, Heidelberg, Germany.
Karzmark, C. J., "A Primer on Theory and Operation of Linear Accelerators in Radiation Therapy", Dec. 1981, p. 1-61.
Wong, J. et al., "Behandlung des Lungenkarzinoms mittels stereotaktischer Strahlentherapie unter Verwendung des weltweit ersten PRIMATOM Systems—eine Fallstudie", Electromedica, vol. 69, 2001, p. 133-136.
Kolda et al., "Optimization by Direct Search: New Perspectives on Some Classical and Modern Methods", SIAM Review, vol. 45, No. 3, 2003, p. 385-482.
Studholme et al., "Automated three-dimensional registration of magnetic resonance and positron emission tomography brain images by multiresolution optimization of voxel similarity measures", Med. Phys., vol. 24, No. 1, Jan. 1997, p. 25-35.
Lu et al., "Fast free-form deformable registration via calculus of variations", Phys. Med. Biol., vol. 49, 2004, p. 3067-3087.
C.T. Kelly, "Iterative Methods for Optimization", North Carolina State University, Society for Industrial and Applied Mathematics, 1999, p. 1-188.
Dadone et al., "Progressive Optimization of Inverse Fluid Dynamic Design Problems", Computers & Fluids, 29 (2000), p. 1-32.
R. Fletcher, "Practical Methods of Optimization", Department of Mathematics and Computer Science, University of Dundee, Scotland, UK, Wiley-Interscience Publication, 1987, p. 1-436.
Singiresu S. Rao, "Engineering Optimization: Theory and Practice", 1996, p. 1-840.
Rangarajan K. Sundaram, "A First Course in Optimization Theory", New York University, Cambridge University Press, 1996, p. 1-376.
Christos H. Papadimitriou, "Combinatorial Optimization: Algorithms and Complexity", Dover Books on Mathematics, 1982, p. 1-496.
Jan Blachut et al., "Emerging Methods for Multidisciplinary Optimization", CISM Courses and Lectures No. 425, International Centre for Mechanical Science, 2001, p. 1-337.
Powell, M.J.D., "Direct search algorithms for optimization calculations", Acta Numerica (1998), p. 287-336, Cambridge University Press.
"Digital Imaging and Communications in Medicine (DICOM) Supplement 11 Radiotherapy Objects", 1997, p. 1-103.
Munro, P., "On Line Portal Imaging", I.J. Radiation Oncology Biology Physics, vol. 39, No. 2, 1997, p. 114.
Smith, R. et al., "Development of cone beam CT for radiotherapy treatment planning", 2001, p. 115.
Munro, P. et al., "Megavoltage Cone-Beam Computed Tomography Using a High Quantum Efficiency Image Receptor", Medical Physics, vol. 29, No. 6, Jun. 2002, p. 1340.
Kestin, L. et al., "Improving the Dosimetric Coverage of Interstitial High-Dose-Rate Breast Implants," Int. J. Radiation Oncology Biol. Phys., vol. 46, No. 1, 2000, pp. 35-43.
Kestin, L. et al., "Intensity Modulation to Improve Dose Uniformity With Tangential Breast Radiotherapy: Initial Clinical Experience," Int. J. Radiation Oncology Biol. Phys., vol. 48, No. 5, 2000, pp. 1559-1568.
Kini, V. et al., "Use of Three-Dimensional Radiation Therapy Planning Tools and Intraoperative Ultrasound to Evaluate High Dose Rate Prostate Brachytherapy Implants," Int. J. Radiation Oncology Biol. Phys., vol. 43, No. 3, 1999, pp. 571-578.

(56) References Cited

OTHER PUBLICATIONS

Laughlin, J. et al., "Evaluation of High Energy Photon External Beam Treatment Planning: Project Summary," Int. J. Radiation Oncology Biol. Phys., vol. 21, No. 1, May 15, 1991, pp. 3-8.
Martinez, A. et al., "Improvement in Dose Escalation Using the Process of Adaptive Radiotherapy Combined with Three-Dimensional Conformal or Intensity-Modulated Beams for Prostate Cancer," Int. J. Radiation Oncology Biol. Phys., vol. 50, No. 5, 2001, pp. 1226-1234.
Masterson, M. et al., "Interinstitutional Experience in Verification of External Photon Dose Calculations," Int. J. Radiation Oncology Biol. Phys., vol. 21, No. 1, May 15, 1991, pp. 37-58.
Michalski, J. et al., "An Evaluation of Two Methods of Anatomical Alignment of Radiotherapy Portal Images," Int. J. Radiation Oncology Biol. Phys., vol. 27, No. 5, 1993, pp. 1199-1206.
Michalski, J. et al., "Prospective Clinical Evaluation of an Electronic Portal Imaging Device," Int. J. Radiation Oncology Biol. Phys., vol. 34, No. 4, 1996, pp. 943-951.
Michalski, J. et al., "The Use of On-line Image Verification to Estimate the Variation in Radiation Therapy Dose Delivery," Int. J. Radiation Oncology Biol. Phys., vol. 27, No. 3, 1993, pp. 707-716.
Milliken, B. et al., "Verification of the omni wedge technique," Med. Phys., vol. 25, No. 8, Aug. 1998, pp. 1419-1423.
Mohan, R., "Three-Dimensional Dose Calculations for Radiation Treatment Planning," Int. J. Radiation Oncology Biol. Phys., vol. 21, No. 1, May 15, 1991, pp. 25-36.
Oldham, M. et al., "Practical aspects of in situ 16O (y,n) 15O activation using a conventional medical accelerator for the purpose of perfusion imaging," Med. Phys., vol. 28, No. 8, Aug. 2001, pp. 1669-1678.
Perera, H. et al., "Rapid Two-Dimensional Dose Measurement in Brachytherapy Using Plastic Scintillator Sheet: Linearity, Signal-to-Noise Ratio, and Energy Response Characteristics," Int. J. Radiation Oncology Biol. Phys., vol. 23, No. 5, 1992, pp. 1059-1069.
Purdy, J. et al., "State of the Art of High Energy Photon Treatment Planning," Font. Radiat. Ther. Onc., vol. 21, 1987, pp. 4-24.
Sharpe, M. et al., "Compensation of x-ray beam penumbra in conformal radiotherapy," Med. Phys., vol. 27, No. 8, Aug. 2000, pp. 1739-1745.
Sharpe, M. et al., "Monitor unit settings for intensity modulated beams delivered using a step-and-shoot approach," Med. Phys., vol. 27, No. 12, Dec. 2000, pp. 2719-2725.
Shiu, A. et al., "Verification data for electron beam dose algorithms," Med. Phys., vol. 19, No. 3, May/Jun. 1992, pp. 623-636.
Siewerdsen, J. et al., "Empirical and theoretical investigation of the noise performance of indirect detection, active matrix flat-panel imagers (AMFPIs) for diagnostic radiology," Med. Phys., vol. 24, No. 1, Jan. 1997, pp. 71-89.
Siewerdsen, J. et al., "Signal, noise power spectrum, and detective quantum efficiency of indirect-detection flat-panel imagers for diagnostic radiology," Med. Phys., vol. 24, No. 1, May 1998, pp. 614-628.
Sontag, M. et al., "State-of-the-Art of External Photon Beam Radiation Treatment Planning," Int. J. Radiation Oncology Biol. Phys., vol. 21, No. 1, May 15, 1991, pp. 9-23.
Stromberg, J. et al., "Active Breathing Control (ABC) for Hodgkin's Disease: Reduction in Normal Tissue Irradiation with Deep Inspiration and Implications for Treatment," Int. J. Radiation Oncology Biol. Phys., vol. 48, No. 3, 2000, pp. 797-806.
Teicher, B. et al., "Allosteric effectors of hemoglobin as modulators of chemotherapy and radiation therapy in vitro and in vivo," Cancer Chemother Pharmacol, vol. 42, 1998, pp. 24-30.
Tepper, J. et al., "Three-Dimensional Display in Planning Radiation Therapy: A Clinical Perspective," Int. J. Radiation Oncology Biol. Phys., vol. 21, No. 1, May 15, 1991, pp. 79-89.
Urie, M. et al., "The Role of Uncertainty Analysis in Treatment Planning," Int. J. Radiation Oncology Biol. Phys., vol. 21, No. 1, May 15, 1991, pp. 91-107.
Vicini, F. et al., "Dose-Volume Analysis for Quality Assurance of Interstitial Brachytherapy for Breast Cancer," Int. J. Radiation Oncology Biol. Phys., vol. 45, No. 3, 1999, pp. 803-810.
Vicini, F. et al., "Implementation of 3D-Virtual Brachytherapy in the Management of Breast Cancer: A Description of a New Method of Interstitial Brachytherapy," Int. J. Radiation Oncology Biol. Phys., vol. 40, No. 3, 1998, pp. 620-635.
Vicini, F. et al., "Low-Dose-Rate Brachytherapy as the Sole Radiation Modality in the Management of Patients with Early-Stage Breast Cancer Treated with Breast-Conserving Therapy: Preliminary Results of a Pilot Trial," Int. J. Radiation Oncology Biol. Phys., vol. 38, No. 2, 1997, pp. 301-310.
Williamson, J. et al., "One-dimensional scatter-subtraction method for brachytherapy dose calculation near bounded heterogeneities," Med. Phys., vol. 20., No. 1, Jan./Feb. 1993, pp. 233-244.
Wong, J. et al., "Conservative management of osteoradionecrosis," Oral Surgery Oral Medicine Oral Pathology, vol. 84, No. 1, Jul. 1997, pp. 16-21.
Wong, J. et al., "The Cumulative Verification Image Analysis Tool for Offline Evaluation of Portal Images," Int. J. Radiation Oncology Biol. Phys., vol. 33, No. 5, 1995, pp. 1301-1310.
Wong, J. et al., "Development of a Second-Generation Fiber-Optic On-Line Image Verification System," Int. J. Radiation Oncology Biol. Phys., vol. 26, No. 2, 1993, pp. 311-320.
Wong, J. et al., Effect of small Inhomogeneities on dose in a cobalt-60 beam, Med. Phys., vol. 8, No. 6, Nov./Dec. 1981, pp. 783-791.
Wong, J. et al., "On methods of inhomogeneity corrections for photon transport," Med. Phys., vol. 17, No. 5, Sep./Oct. 1990, pp. 807-814.
Wong, J. et al., "A new approach to CT pixel-based photon dose calculations in heterogeneous media," Med. Phys., vol. 10, No. 2, Mar./Apr. 1983, pp. 199-208.
Wong, J. et al., "On-line image verification in radiation therapy: an early USA experience," Medical Progress Through Technology, vol. 19, No. 1, 1993, pp. 43-54.
Wong, J. et al., "On-line Radiotherapy Imaging with an Array of Fiber-Optic Image Reducers," Int. J. Radiation Oncology Biol. Phys., vol. 18, No. 6, Jun. 1990, pp. 1477-1484.
Wong, J. et al., "Portal Dose Images I: Quantitative Treatment Plan Verification," Int. J. Radiation Oncology Biol. Phys., vol. 18, No. 6, Jun. 1990, pp. 1455-1463.
Wong, J. et al., "Reconsideration of the power-law (Batho) equation for inhomogeneity corrections," Med. Phys., vol. 9, No. 4, Jul./Aug. 1982, pp. 521-530.
Wong, J. et al., "Role of Inhomogeneity Corrections in Three-Dimensional Photon Treatment Planning," Int. J. Radiation Oncology Biol. Phys., vol. 21, No. 1, May 15, 1991, pp. 59-69.
Wong, J. et al., "Second scatter contribution to dose in a cobalt-60 beam," Med. Phys., vol. 8, No. 6, Nov./Dec. 1981, pp. 775-782.
Wong, J. et al., "Treatment Verifications and Patient Dose Estimations Using Portal Dose Imaging," 1988, pp. 213-225.
Wong, J. et al., "The Use of Active Breathing Control (ABC) to Reduce Margin for Breathing Motion," Int. J. Radiation Oncology Biol. Phys., vol. 44., No. 4, 1999, pp. 911-919.
Wu, Y. et al., "Implementing multiple static field delivery for intensity modulated beams," Med. Phys., vol. 28, No. 1, Nov. 2001, pp. 2188-2197.
Yan, D. et al., "The Use of Adaptive Radiation Therapy to Reduce Setup Error: A Prospective Clinical Study," Int. J. Radiation Oncology Biol. Phys., vol. 41, No. 3, 1998, pp. 715-720.
Yan, D. et al., "Adaptive Radiation Therapy," Phys. Med. Biol., vol. 42, 1997, pp. 123-132.
Yan, D. et al., "A Model to Accumulate Fractionated Dose in a Deforming Organ," Int. J. Radiation Oncology Biol. Phys., vol. 44, No. 3, 1999, pp. 665-675.
Yan, D. et al., "A New Model for "Accept or Reject" Strategies in Off-Line and On-Line Megavoltage Treatment Evaluation," Int. J. Radiation Oncology Biol. Phys., vol. 31, No. 4, 1995, pp. 943-952.
Ying, X. et al., "Portal Dose Images II: Patient Dose Estimation," Int. J. Radiation Oncology Biol. Phys., vol. 18, No. 6, Jun. 1990, pp. 1465-1475.

(56) References Cited

OTHER PUBLICATIONS

Yu, C. et al., A method for implementing dynamic photon beam intensity modulation using independent jaws and a multileaf collimator, Phys. Med. Biol., vol. 40, 1995, pp. 769-787.

Carey, G., "Computational Grids Generation, Adaptation, and Solution Strategies," The University of Texas, Austin, Texas, 1997.

Verellen, D. et al., "A (short) history of image-guided radiotherapy, Radiotherapy & Oncology," vol. 86, 2008, p. 4-13.

Van Herk, M. et al., "Automatic three-dimensional correlation of CT-CT, CT-MRI, and CT-SPECT using chamfer matching," Medical Physics, 1994, p. 1163-1178.

Woods, R.P. et al., "MRI-PET Registration with Automated Algorithm," Journal of Computer Assisted Tomography, vol. 17, No. 4, 1993, p. 536-546.

Jaffray, D.A. et al., "A Volumetric Cone-Beam CT System Based on a 41×41 cm2 Flat-Panel Imager," Proc. SPIE, vol. 4320, 2001, p. 800-807.

Otto, K., "Intensity Modulation of Therapeutic Photon Beams Using a Rotating Multileaf Collimator," Medical Physics, vol. 31, No. 3, 2003, p. 167.

Lim, J., "Optimization in Radiation Treatment Planning," Madison, Wisconsin, 2002, 179 pages.

Wang, X. et al., "Development of Methods for Beam Angle Optimization for IMRT Using an Accelerated Exhaustive Search Strategy," Int. J. Radiation Oncology Biol. Phys., vol. 60, No. 4, 2004, p. 1325-1337.

Nag, S., et al., "Intraoperative Planning and Evaluation of Permanent Prostate Brachytherapy: Report of the American Brachytherapy Society," Int. J. Radiation Oncology Biol. Phys., vol. 51, No. 5, 2001, p. 1422-1430.

Munro, P., "Portal Imaging Technology: Past, Present, and Future, Seminars in Radiation Oncology," vol. 5, No. 2, Apr. 1995, p. 115-133.

De Neve, W., et al., "Routine clinical on-line portal imaging followed by immediate field adjustment using a tele-controlled patient couch," Radiotherapy and Oncology, vol. 24, 1992, p. 45-54.

Antonuk, L.E. et al., "Thin-Film, Flat-Panel, Composite Imagers for Projection and Tomographic Imaging, IEEE Transactions on Medical Imaging," vol. 13, No. 3, Sep. 1994, p. 482-490.

Sephton, R., et al., "A diagnostic-quality electronic portal imaging system," Radiotherapy and Oncology, vol. 35, 1995, p. 240-247.

Kirby, M.C. et al., "Clinical Applications of Composite and Realtime Megavoltage Imaging," Clinical Oncology, vol. 7, 1995, p. 308-316.

Webb, S. et al., "Tomographic Reconstruction from Experimentally Obtained Cone-Beam Projections," IEEE Transactions on Medical Imaging, vol. MI-6, Mar. 1987, p. 67-73.

Midgley, S.M. et al., "A Feasibility Study for the Use of Megavoltage Photons and a Commercial Electronic Portal Imaging Area Detector for Beam Geometry CT Scanning to Obtain 3D Tomographic Data Sets of Radiotherapy Patients in the Treatment Position," 1996, 2 pages.

Antonuk, L.E. et al., "Demonstration of megavoltage and diagnostic x-ray imaging with hydrogenated amorphous silicon arrays," 1992, p. 1455-1466.

Chabbal, J. et al., "Amorphous Silicon X-ray Image Sensor," SPIE, vol. 2708, 1996, p. 499-510.

Ning, R. et al., "Selenium Flat Panel Detector-Based Volume Tomographic Angiography Imaging: Phantom Studies," SPIE, vol. 3336, 1998, p. 316-324.

Redpath, A.T. et al., "Chapter 6: Simulator Computed Tomography, The Modern Technology of Radiation Oncology," 1999, pp. 169-189.

Boyer, A. et al., "Laser "Cross-hair" sidelight," Medical Physics, vol. 5, No. 1, 1978, p. 58-60.

Jaffray, D. et al., "Image Guided Radiotherapy of the Prostate," 2001, p. 1075-1080.

Mackenzie, M. et al., "Intensity modulated arc deliveries approximated by a large number of fixed gantry position sliding window dynamic multileaf collimator fields," Medical Physics, vol. 29, No. 10, Oct. 2002, p. 2359-2365.

Bissonnette, J-P et al., "An Alternative X-Ray Detector for Portal Imaging: High Density Glass Scintillator," 1993, p. 36-37.

Bissonnette, J-P et al., "Physical characterization and optimal magnification of a portal imaging system," SPIE, vol. 1651 Medical Imaging IV: Instrumentation, 1992, p. 182-188.

Ning, R. et al., "Real Time Flat Panel Detector-Based Volume Tomographic Angiography Imaging: Detector Evaluation," Progress in Biomedical Optics and Imaging, vol. 1, No. 22, 2000, p. 396-407.

Munro, P. et al., "Therapy imaging: limitations of imaging with high energy x-ray beams," SPIE, vol. 767 Medical Imaging, 1987, p. 178-184.

Wright, M. et al., "Amorphous silicon dual mode medical imaging system," SPIE, vol. 3336, 1998, p. 505-514.

Cho, Y. et al., "Thermal Modelling of a Kilovoltage X-Ray Source for Portal Imaging," Proceedings of the 22nd Annual EMBS International Conference, Jul. 23-28, 2000, Chicago, IL, p. 1856-1860.

Zheng, Z. et al., "Fast 4D Cone-Beam Reconstruction Using the McKinnon-Bates Algorithm with Truncation Correction and Non Linear Filtering," Progress in Biomedical Optics and Imaging, vol. 12, No. 30, 2011, p. 1-8.

Ebert, M. et al., "3D image guidance in radiotherapy: a feasibility study," Proceedings of SPIE, vol. 4322, 2001, p. 1807-1816.

Ford, E.C. et al., "Cone-beam CT with megavoltage beams and an amorphous silicon electronic portal imaging device: Potential for verification of radiotherapy of lung cancer," Medical Physics 29, vol. 12, Dec. 2002, p. 2913-2924.

Hunt, P. et al., "Development of an IMRT quality assurance program using an amorphous silicon electronic portal imaging device," Australasian Physical and Engineering Sciences in Medicine, vol. 23, Dec. 2000, 1 page.

Mueller, K. et al., "Cone-Beam Computed Tomography (CT) for a Megavoltage Linear Accelerator (LINAC) Using an Electronic Portal Imaging Device (EPID) and the Algebraic Reconstruction Technique (ART)," Proceedings of the 22nd Annual EMBS International Conference, Jul. 23-28, 2000, Chicago, IL, p. 2875-2878.

Varian Medical Systems, 2002 Annual Report, Varian Medical Systems, Inc., 2002, Palo Alto, CA, p. 1-28.

Ferris, M. et al., "An Optimization Approach for Radiosurgery Treatment Planning", SIAM J. Optim., vol. 13, No. 3, 2003, p. 921-937.

Ferris, M. et al., "Radiosurgery Treatment Planning via Nonlinear Programming", Annals of Operations Research, vol. 119, 2003, p. 247-260.

Rowbottom, C. et al., "Simultaneous optimization of beam orientations and beam weights in conformal radiotherapy", Medical Physics, vol. 28, 2001, p. 1696-1702.

Scholz, C. et al., "Development and clinical application of a fast superposition algorithm in radiation therapy", Radiotherapy and Oncology, vol. 69, 2003, p. 79-90.

Colbeth, R. et al., "40 × 30 cm Flat Panel Imager for Angiography, R&F, and Cone-Beam CT Applications," Progress in Biomedical Optics and Imaging, vol., No. 25, 2001, p. 94-102.

Colbeth, R. et al., "Characterization of an Amorphous Silicon Fluoroscopic Imager," SPIE, vol. 3032, 1997, p. 42-51.

Colbeth, R. et al., "Characterization of a third generation, multi-mode sensor panel," SPIE, vol. 3659, 1999, p. 491-500.

Colbeth, R. et al., "A Multi-mode X-ray Imager for Medical and Industrial Applications," 1998, p. 629-632.

Colbeth, R. et al., "Flat panel imaging system for fluoroscopy applications," SPIE, vol. 3336, 1998, p. 376-387.

Gilblom, D. et al., "Real-time x-ray imaging with flat panels," SPIE, vol. 3399, 1998, p. 213-223.

Gilblom, D. et al., "A real-time, high-resolution camera with an amorphous silicon large-area sensor," SPIE, vol. 3302, 1998, p. 29-38.

Jaffray, D. et al., "Medical linear accelerator x-ray sources: Variation with make, model, and time," SPIE, vol. 1651, Medical Imaging VI: Instrumentation, 1992, p. 174-181.

Klausmeier-Brown, M.E. et al., "Real-Time Image Processing in a Flat-Panel, Solid-State, Medical Fluoroscopic Imaging System," SPIE, vol. 3303, 1998, p. 2-7.

(56) References Cited

OTHER PUBLICATIONS

Kubo, H. et al., "Potential and role of a prototype amorphous silicon array electronic portal imaging device in breathing synchronized radiotherapy," Medical Physics, vol. 26, No. 11, Nov. 1999, p. 2410-2414.
Munro, P. et al., "A Digital Fluoroscopic Imaging Device for Radiotherapy Localization," Int. J. Radiation Oncology Biol. Phys., vol. 18, 1990, p. 641-649.
United States Patent and Trademark Offce, "Office Action" dated Sep. 23, 2016 with respect to U.S. Appl. No. 14/710,485.
United States Patent and Trademark Offce, "Office Action" dated Nov. 30, 2016 with respect to U.S. Appl. No. 15/266,156.
United States Patent and Trademark Offce, "Office Action" dated Nov. 30, 2016 with respect to U.S. Appl. No. 15/266,225.
United States Patent and Trademark Offce, "Office Action" dated Nov. 30, 2016 with respect to U.S. Appl. No. 15/266,264.
United States Patent and Trademark Offce, "Office Action" dated Dec. 5, 2016 with respect to U.S. Appl. No. 15/266,313.
United States Patent and Trademark Offce, "Office Action" dated Dec. 5, 2016 with respect to U.S. Appl. No. 15/266,193.
United States Patent and Trademark Offce, "Office Action" dated Dec. 19, 2016 with respect to U.S. Appl. No. 15/266,371.
United States Patent and Trademark Offce, "Office Action" dated Dec. 19, 2016 with respect to U.S. Appl. No. 15/266,467.
Rapid portal imaging with a high-efficiency, large field-of-view detector, Mosleh-Shirazi et al., 1998, pp. 2333-2346.
Comparison of CT numbers determined by a simulator CT & a diagnostic scanner, M. Hartson, D. Champney, J. Currier, J. Krise, J. Marvel, M. Schrijvershof, J. Sensing, 1995, pp. 37-45.
Digital radiotherapy simulator, P. Cho, K. Lindsley, J. Douglas, K. Stelzer, T. Griffin, 1998, pp. 1-7.
A prototype 3D CT extension for radiotherapy simulators, S. Agostinelli, F. Foppiano, 2001, pp. 11-21.
A cone-beam megavoltage CT scanner for treatment verification in conformal radiotherapy, M. Shirazi, P. Evans, W. Swindell, S. Webb, M. Partridge, 1998, pp. 319-328.
Comparison of flat-panel detector and image-intensifier detector for cone-beam CT, R. Baba, Y. Konno, K. Ueda, S. Ikeda, 2002, pp. 153-158.
Sampling Issues for Optimization in Radiotherapy, Ferris et al., Apr. 8, 2004, pp. 1-47.
Optimization of Gamma Knife Radiosurgery, Ferris et al., Apr. 8, 2004, pp. 1-58.
Linear accelerator output variations and their consequences for megavoltage imaging, Partridge et al., 1998, pp. 1443-1452.
Fast and Accurate Three-Dimensional Reconstruction from Cone-Beam Projection Data Using Algebraic Methods, Mueller, 1998, pp. 1-114.
Novel Approximate Approach for High-Quality Image Reconstruction in Helical Cone Beam CT at Arbitrary Pitch, Schaller et al., 2001, pp. 113-127.
Abutment Region Dosimetry for Serial Tomography, Low et al., 1999, pp. 193-203.
Signal, noise, and readout considerations in the development of amorphous silicon photodiode arrays for radiotherapy and diagnostic x-ray imaging, Antonuk et al., 1991, pp. 108-119.
Non-coplanar beam direction optimization for intensity, Meedt et al., 2003, pp. 2999-3019.
Combining Multileaf Fields to Modulate Fluence Distributions, Galvin et al., 1993, pp. 697-705.
Joint Submission Regarding Constructions of Disputed and Undisputed Claim Terms dated Mar. 1, 2016 in Certain Radiotherapy Systems and Treatment Planning Software, and Components Thereof, Investigation No. 337-TA-968.
Selected pages of Appendix 2 to Complainants' Eighth Supplemental Responses and Objections to Respondents' First Set of Interrogatories, dated Mar. 28, 2016 in Certain Radiotherapy Systems and Treatment Planning Software, and Components Thereof, Investigation No. 337-TA-968.
Clinical Implementation of Non-Physical Wedges, 1999 AAPM Refresher Course, presented at 41st Annual Meeting, American Association of Physicists in Medicine, Chang.
Clinac 600C & 600 C/D Equipment Specification, Varian Medical Systems, 2000.
Clinac Accelerators, Varian Medical Systems, 2003.
Automatic Variation of Field Size and Dose Rate in Rotation Therapy, Mantel and Perry, 1977, pp. 697-704.
The Physics of Intensity-Modulated Radiation Therapy, Boyer, 2002, pp. 38-44.
The Relationship Between the Number of Shots and the Quality of Gamma Knife Radiosurgeries, Cheek et al., 2004, pp. 1-13.
Guidance document on delivery, treatment planning, and clinical implementation of IMRT: Report of the IMRT subcommittee of the AAPM radiation therapy committee, Ezzell et al., Aug. 2003, pp. 2089-2115.
Analysis of various beamlet sizes for IMRT with 6 MV Photons, Sohn et al., 2004, pp. 2432-2439.
Effects of the intensity levels and beam map resolutions on static IMRT plans, Sun et al., 2004, pp. 2402-2411.
Stereotactic Radiosurgery, Schell et al., Jun. 1995, pp. 1-88.
Cone-beam computed tomography with a flat-panel imager: Effects of image lag, J. Siewerdsen, D. Jaffray, 1999, pp. 2635-2647.
Supplementary European Search Report dated Jan. 12, 2011; EP Appln No. 03786979.9; 3 pages.
Varian Medical Systems, Inc., Communication pursuant to Article 94(3) EPC, EP Application No. 03 786 979.9-1657, dated Jan. 30, 2014, 8 pages.
Inter Parties Review Petition—U.S. Pat. No. 7,906,770, Sep. 28, 2016.
Inter Parties Review Petition—U.S. Pat. No. 8,696,538, Sep. 28, 2016.
Inter Parties Review Petition—U.S. Pat. No. 7,880,154, Sep. 28, 2016.
Electronic portal imaging devices: a review and historical perspective of contemporary technologies and research, Antonuk, 2002, pp. R31-R65.
Clinical application of IMRT, Hatano, 2002, pp. 199-204.
Use of a simulator and treatment planning computer as a CT scanner for radiotherapy planning, Redpath, AT, et al., 1984, pp. 281-287.
Notification of Reasons for Rejection in Japanese Patent Application No. 2001-559337, dated Mar. 10, 2011, pp. 1-8.
6th International Workshop on Electronic Portal Imaging, EP12K: Program and Abstract Book, 2000, pp. 1-221.
Flat-panel Cone-beam CT for Image-guided External Beam Radiotherapy, Jaffray D. et al., Oct. 1999, pp. 1-36.
Three dimensional radiation treatment planning, Kutcher, GJ, et al., 1987.
Practical realization of a method of digital x-ray diagnostics in a scanning-type device, Berkeshev, O.S. et al, 2001. pp. 36-37.

* cited by examiner

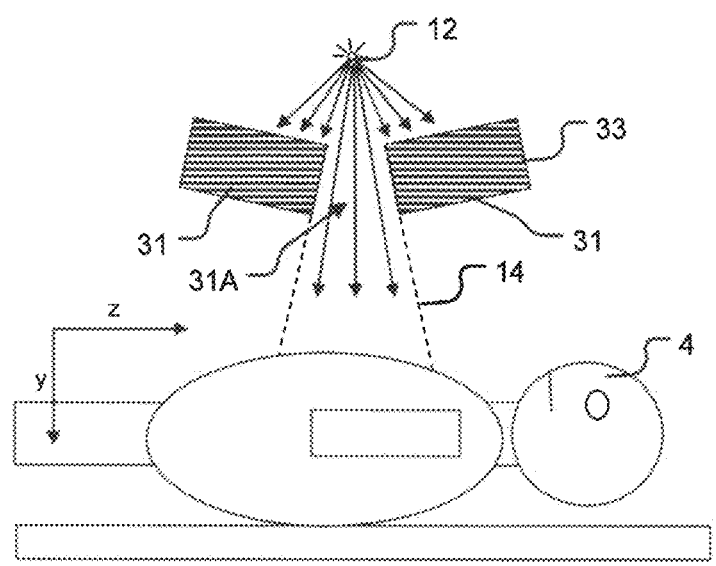
FIGURE 3A
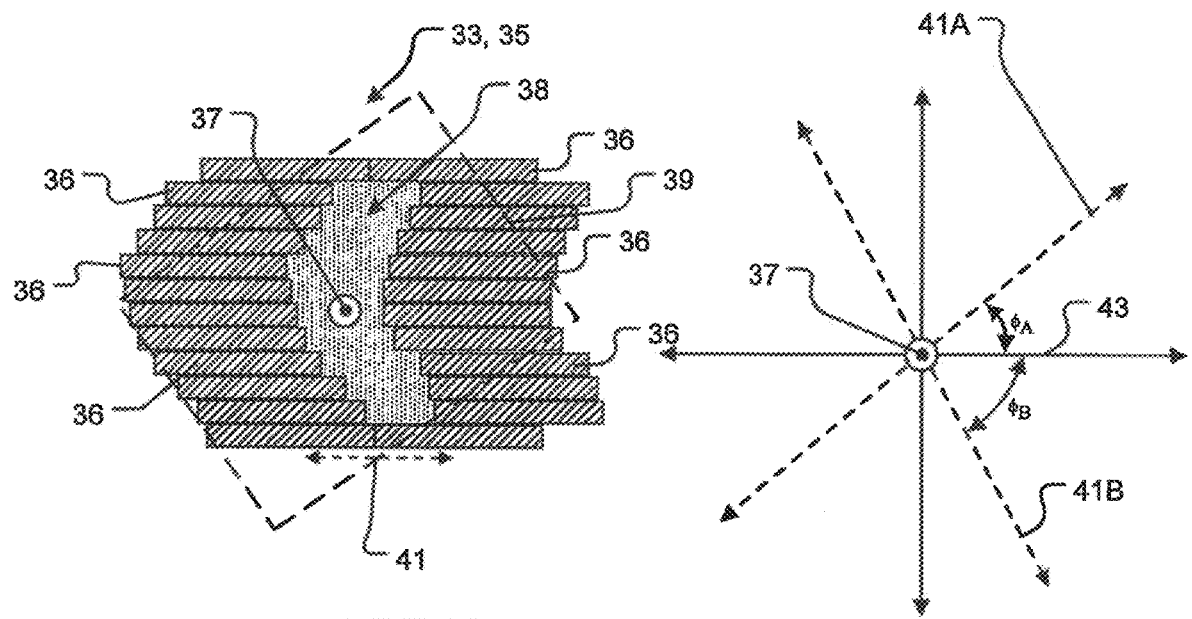
FIGURE 3B
FIGURE 3C

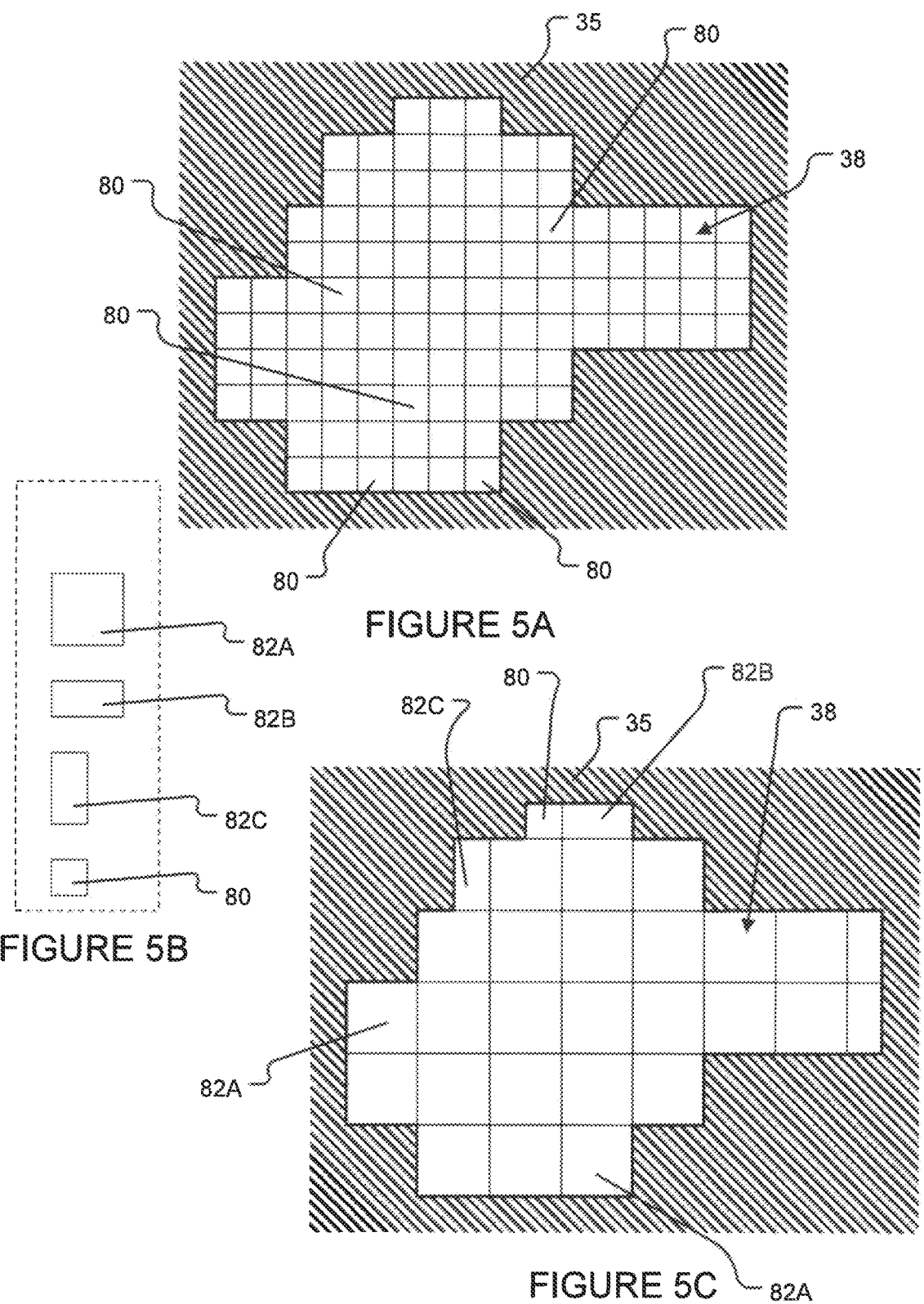

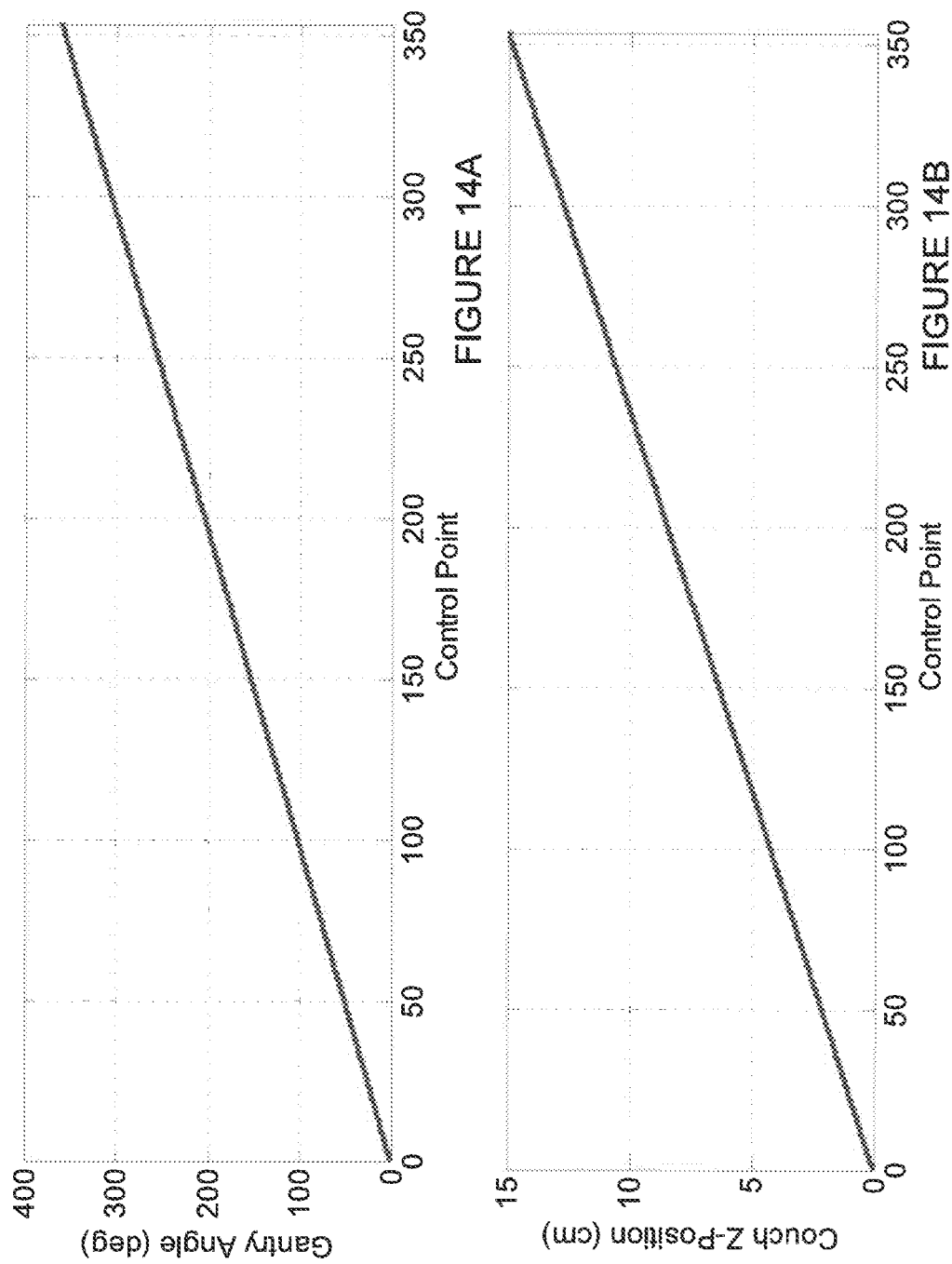

Gantry = 0 degrees

Gantry = 180 degrees

Gantry = 0 degrees

Gantry = 180 degrees

METHODS AND APPARATUS FOR THE PLANNING AND DELIVERY OF RADIATION TREATMENTS

CROSS-REFERENCE TO RELATED APPLICATIONS

This application is a continuation of U.S. patent application Ser. No. 15/707,931, filed Sep. 18, 2017, which is a continuation of U.S. patent application Ser. No. 15/382,469, filed Dec. 16, 2016, now U.S. Pat. No. 9,788,783, issued Oct. 17, 2017, which is a continuation of U.S. patent application Ser. No. 14/710,485, filed May 12, 2015, now U.S. Pat. No. 9,630,025, issued Apr. 25, 2017, which is a continuation of U.S. patent application Ser. No. 14/202,305, filed Mar. 10, 2014, now U.S. Pat. No. 9,050,459, issued Jun. 9, 2015, which is a continuation of U.S. patent application Ser. No. 12/986,420, filed Jan. 7, 2011, now U.S. Pat. No. 8,696,538, issued Apr. 15, 2014, which is a continuation of U.S. patent application Ser. No. 12/132,597, now U.S. Pat. No. 7,880,154, issued Feb. 1, 2011, which is a continuation-in-part of U.S. patent application Ser. No. 11/996,932, filed Jan. 25, 2008, now U.S. Pat. No. 7,906,770, issued Mar. 15, 2011, which is a 35 U.S.C. § 371 application which claims benefit of International Application No. PCT/CA2006/001225, filed Jul. 25, 2006, which claims benefit of U.S. Provisional Patent Application No. 60/701,974, filed Jul. 25, 2005, all of which are incorporated by reference herein.

TECHNICAL FIELD

This invention relates to radiation treatment. The invention relates particularly to methods and apparatus for planning and delivering radiation to a subject to provide a desired three-dimensional distribution of radiation dose.

BACKGROUND

The delivery of carefully-planned doses of radiation may be used to treat various medical conditions. For example, radiation treatments are used, often in conjunction with other treatments, in the treatment and control of certain cancers. While it can be beneficial to deliver appropriate amounts of radiation to certain structures or tissues, in general, radiation can harm living tissue. It is desirable to target radiation on a target volume containing the structures or tissues to be irradiated while minimizing the dose of radiation delivered to surrounding tissues. Intensity modulated radiation therapy (IMRT) is one method that has been used to deliver radiation to target volumes in living subjects.

IMRT typically involves delivering shaped radiation beams from a few different directions. The radiation beams are typically delivered in sequence. The radiation beams each contribute to the desired dose in the target volume.

A typical radiation delivery apparatus has a source of radiation, such as a linear accelerator, and a rotatable gantry. The gantry can be rotated to cause a radiation beam to be incident on a subject from various different angles. The shape of the incident radiation beam can be modified by a multi-leaf collimator (MLC). A MLC has a number of leaves which are mostly opaque to radiation. The MLC leaves define an aperture through which radiation can propagate. The positions of the leaves can be adjusted to change the shape of the aperture and to thereby shape the radiation beam that propagates through the MLC. The MLC may also be rotatable to different angles.

Objectives associated with radiation treatment for a subject typically specify a three-dimensional distribution of radiation dose that it is desired to deliver to a target region within the subject. The desired dose distribution typically specifies dose values for voxels located within the target. Ideally, no radiation would be delivered to tissues outside of the target region. In practice, however, objectives associated with radiation treatment may involve specifying a maximum acceptable dose that may be delivered to tissues outside of the target.

Treatment planning involves identifying an optimal (or at least acceptable) set of parameters for delivering radiation to a particular treatment volume. Treatment planning is not a trivial problem. The problem that treatment planning seeks to solve involves a wide range of variables including:
- the three-dimensional configuration of the treatment volume;
- the desired dose distribution within the treatment volume;
- the locations and radiation tolerance of tissues surrounding the treatment volume; and
- constraints imposed by the design of the radiation delivery apparatus.

The possible solutions also involve a large number of variables including:
- the number of beam directions to use;
- the direction of each beam;
- the shape of each beam; and
- the amount of radiation delivered in each beam.

Various conventional methods of treatment planning are described in:
- S. V. Spirou and C.-S. Chui. *A gradient inverse planning algorithm with dose-volume constraints*, Med. Phys. 25, 321-333 (1998);
- Q. Wu and R. Mohand. *Algorithm and functionality of an intensity modulated radiotherapy optimization system*, Med. Phys. 27, 701-711 (2000);
- S. V. Spirou and C.-S. Chui. *Generation of arbitrary intensity profiles by dynamic jaws or multileaf collimators*, Med. Phys. 21, 1031-1041 (1994);
- P. Xia and L. J. Verhey. *Multileaf collimator leaf sequencing algorithm for intensity modulated beams with multiple static segments*, Med. Phys. 25, 1424-1434 (1998); and
- K. Otto and B. G. Clark. *Enhancement of IMRT delivery through MLC rotation,*" Phys. Med. Biol. 47, 3997-4017 (2002).

Acquiring sophisticated modern radiation treatment apparatus, such as a linear accelerator, can involve significant capital cost. Therefore it is desirable to make efficient use of such apparatus. All other factors being equal, a radiation treatment plan that permits a desired distribution of radiation dose to be delivered in a shorter time is preferable to a radiation treatment plan that requires a longer time to deliver. A treatment plan that can be delivered in a shorter time permits more efficient use of the radiation treatment apparatus. A shorter treatment plan also reduces the risk that a subject will move during delivery of the radiation in a manner that may significantly impact the accuracy of the delivered dose.

Despite the advances that have been made in the field of radiation therapy, there remains a need for radiation treatment methods and apparatus and radiation treatment planning methods and apparatus that provide improved control over the delivery of radiation, especially to complicated target volumes. There also remains a need for such methods and apparatus that can deliver desired dose distributions relatively quickly.

SUMMARY

One aspect of the invention provides a method for planning delivery of radiation dose to a target area within a subject. The method comprises: defining a set of one or more optimization goals, the set of one or more optimization goals comprising a desired dose distribution in the subject; specifying an initial plurality of control points along an initial trajectory, the initial trajectory involving relative movement between a radiation source and the subject in a source trajectory direction; and iteratively optimizing a simulated dose distribution relative to the set of one or more optimization goals to determine one or more radiation delivery parameters associated with each of the initial plurality of control points. For each of the initial plurality of control points, the one or more radiation delivery parameters may comprise positions of a plurality of leaves of a multi-leaf collimator (MLC). The MLC leaves may be moveable in a leaf-translation direction. During relative movement between the radiation source and the subject along the initial trajectory, the leaf-translation direction is oriented at a MLC orientation angle φ with respect to the source trajectory direction and wherein an absolute value of the MLC orientation angle φ satisfies $0°<|\varphi|<90°$.

Another aspect of the invention provides a method for delivering radiation dose to a target area within a subject. The method comprises: defining a trajectory for relative movement between a treatment radiation source and the subject in a source trajectory direction; determining a radiation delivery plan; and while effecting relative movement between the treatment radiation source and the subject along the trajectory, delivering a treatment radiation beam from the treatment radiation source to the subject according to the radiation delivery plan to impart a dose distribution on the subject. Delivering the treatment radiation beam from the treatment radiation source to the subject comprises varying at least one of: an intensity of the treatment radiation beam; and a shape of the treatment radiation beam over at least a portion of the trajectory.

Varying at least one of the intensity of the treatment radiation beam and the shape of the treatment radiation beam over at least the portion of the trajectory, may comprise varying positions of a plurality of leaves of a multi-leaf collimator (MLC) in a leaf-translation direction. During relative movement between the treatment radiation source and the subject along the trajectory, the leaf-translation direction may be oriented at a MLC orientation angle φ with respect to the source trajectory direction wherein an absolute value of the MLC orientation angle φ satisfies $0°<|\varphi|<90°$.

Varying at least one of the intensity of the treatment radiation beam and the shape of the treatment radiation beam over at least the portion of the trajectory may comprise varying a rate of radiation output of the radiation source while effecting continuous relative movement between the treatment radiation source and the subject along the trajectory.

Other aspects of the invention provide program products comprising computer readable instructions which, when executed by a processor, cause the processor to execute, at least in part, any of the methods described herein. Other aspects of the invention provide systems comprising, inter alia, controllers configured to execute, at least in part, any of the methods described herein.

Further aspects of the invention and features of embodiments of the invention are set out below and illustrated in the accompanying drawings.

BRIEF DESCRIPTION OF THE DRAWINGS

The appended drawings illustrate non-limiting example embodiments of the invention.

FIG. 3A is a schematic cross-sectional view of a beam-shaping mechanism.

FIG. 3B is a schematic beam's eye plan view of a multi-leaf collimator-type beam-shaping mechanism.

FIG. 3C schematically depicts a system for defining the angle of leaf-translation directions about the beam axis.

FIGS. 5A, 5B and 5C illustrate dividing an aperture into beamlets according to a particular embodiment of the invention.

FIGS. 14A-14D show the results (the motion axes parameters, the intensity and the beam shaping parameters) of the optimization process of the FIG. 10 example.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

This invention relates to the planning and delivery of radiation treatments by modalities which involve moving a radiation source along a trajectory relative to a subject while delivering radiation to the subject. In some embodiments the radiation source is moved continuously along the trajectory while in some embodiments the radiation source is moved intermittently. Some embodiments involve the optimization of the radiation delivery plan to meet various optimization goals while meeting a number of constraints. For each of a number of control points along a trajectory, a radiation delivery plan may comprise: a set of motion axes parameters, a set of beam shape parameters and a beam intensity.

Figure 1:
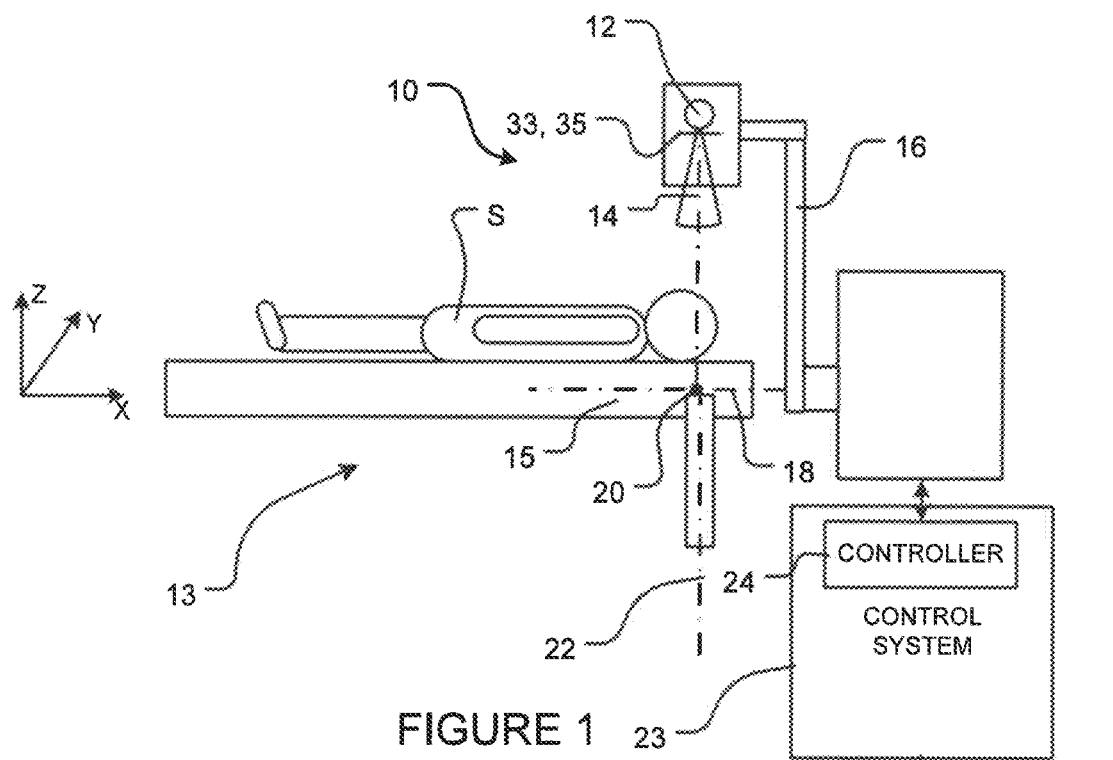
FIG. 1 is a schematic view of an exemplary radiation delivery apparatus in conjunction with which the invention may be practised.

FIG. 1 shows an example radiation delivery apparatus 10 comprising a radiation source 12 capable of generating or otherwise emitting a beam 14 of radiation. Radiation source 12 may comprise a linear accelerator, for example. A subject S is positioned on a table or "couch" 15 which can be placed in the path of beam 14. Apparatus 10 has a number of movable parts that permit the location of radiation source 12 and orientation of radiation beam 14 to be moved relative to subject S. These parts may be referred to collectively as a beam positioning mechanism 13.

In the illustrated radiation delivery apparatus 10, beam positioning mechanism 13 comprises a gantry 16 which supports radiation source 12 and which can be rotated about an axis 18. Axis 18 and beam 14 intersect at an isocenter 20. Beam positioning mechanism 13 also comprises a moveable couch 15. In exemplary radiation delivery apparatus 10, couch 15 can be translated in any of three orthogonal directions (shown in FIG. 1 as X, Y, and Z directions) and can be rotated about an axis 22. In some embodiments, couch 15 can be rotated about one or more of its other axes. The location of source 12 and the orientation of beam 14 can be changed (relative to subject S) by moving one or more of the movable parts of beam positioning mechanism 13.

Each separately-controllable means for moving source 12 and/or orienting beam 14 relative to subject S may be termed a "motion axis". In some cases, moving source 12 or beam 14 along a particular trajectory may require motions of two or more motion axes. In exemplary radiation delivery apparatus 10, motion axes include:
- rotation of gantry 16 about axis 18;
- translation of couch 15 in any one or more of the X, Y, Z directions; and
- rotation of couch 15 about axis 22.

Radiation delivery apparatus 10 typically comprises a control system 23 capable of controlling, among other things, the movement of its motion axes and the intensity of radiation source 12. Control system 23 may generally comprise hardware components and/or software components. In the illustrated embodiment, control system 23 comprises a controller 24 capable of executing software instructions. Control system 23 is preferably capable of receiving (as input) a set of desired positions for its motion axes and, responsive to such input, controllably moving one or more of its motion axes to achieve the set of desired motion axes positions. At the same time, control system 23 may also control the intensity of radiation source 12 in response to input of a set of desired radiation intensities.

While radiation delivery apparatus 10 represents a particular type of radiation delivery apparatus in conjunction with which the invention may be implemented, it should be understood that the invention may be implemented on different radiation delivery apparatus which may comprise different motion axes. In general, the invention may be implemented in conjunction with any set of motion axes that can create relative movement between a radiation source 12 and a subject S, from a starting point along a trajectory to an ending point.

Figure 1A:
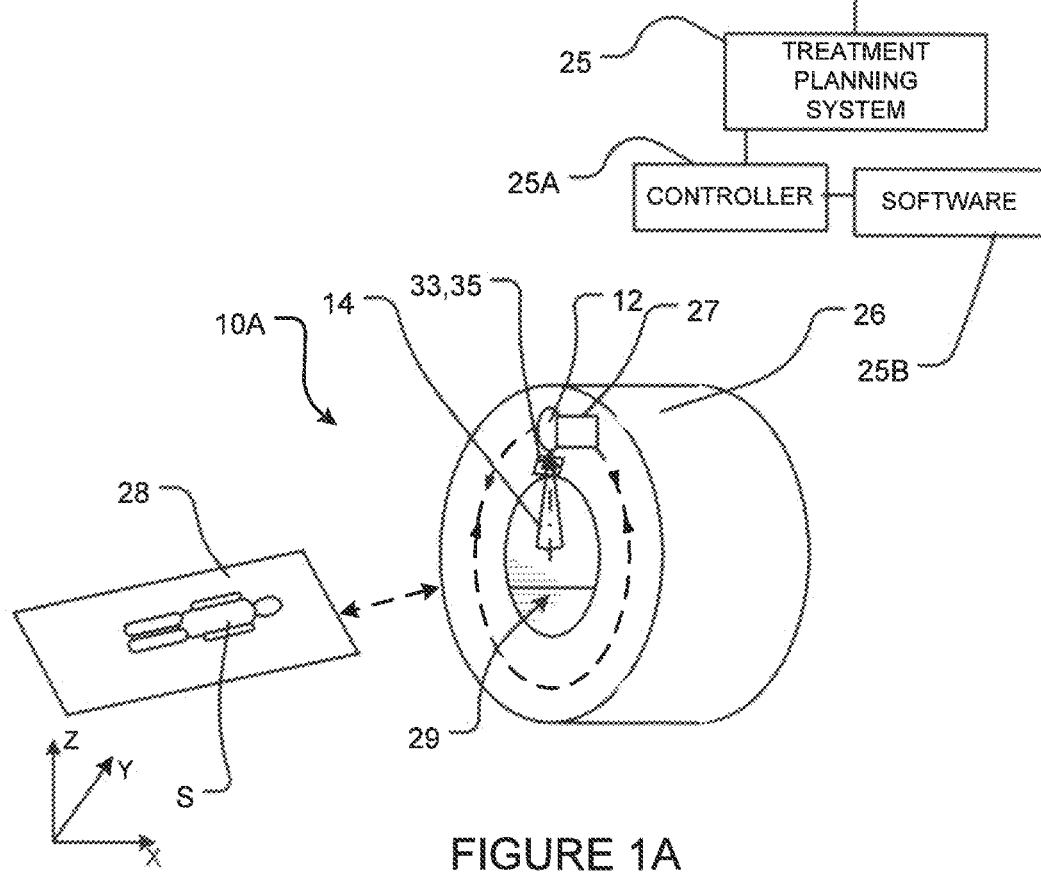
FIG. 1A is a schematic view of another exemplary radiation delivery apparatus in conjunction with which the invention may be practised.

Another example of a radiation delivery apparatus 10A that provides an alternative set of motion axes is shown in FIG. 1A. In exemplary apparatus 10A, source 12 is disposed in a toroidal housing 26. A mechanism 27 permits source 12 to be moved around housing 26 to irradiate a subject S from different sides. Subject S is on a table 28 which can be advanced through a central aperture 29 in housing 26. Apparatus having configurations like that shown schematically in FIG. 1A are used to deliver radiation in a manner commonly called "Tomotherapy".

In accordance with particular embodiments of the invention, beam positioning mechanism 13 causes source 12 and/or beam 14 to move along a trajectory while radiation dose is controllably delivered to target regions within subject S. A "trajectory" is a set of one or more movements of one or more of the movable parts of beam position mechanism 13 that results in the beam position and orientation changing from a first position and orientation to a second position and orientation. The first and second positions and the first and second orientations are not necessarily different. For example, a trajectory may be specified to be a rotation of gantry 16 from a starting point through an angle of 360° about axis 18 to an ending point in which case the beam position and orientation at the starting and ending points are the same.

The first and second beam positions and beam orientations may be specified by a first set of motion axis positions (corresponding to the first beam position and the first beam orientation) and a second set of motion axis positions (corresponding to the second beam position and the second beam orientation). As discussed above, control system 23 of radiation delivery apparatus 10 can controllably move its motion axes between the first set of motion axis positions and the second set of motion axis positions. In general, a trajectory may be described by more than two beam positions and beam orientations. For example, a trajectory may be specified by a plurality of sets of motion axis positions, each set of motion axis positions corresponding to a particular beam position and a particular beam orientation. Control system 23 can then controllably move its motion axes between each set of motion axis positions.

In general, a trajectory may be arbitrary and is only limited by the particular radiation delivery apparatus and its particular beam positioning mechanism. Within constraints imposed by the design of a particular radiation delivery apparatus 10 and its beam positioning mechanism 13, source 12 and/or beam 14 may be caused to follow an arbitrary trajectory relative to subject S by causing appropriate combinations of movements of the available motion axes. A trajectory may be specified to achieve a variety of treatment objectives. For example, a trajectory may be selected to have a high ratio of target tissue within the beam's eye view compared to healthy tissue within the beam's eye view or to avoid important healthy organs or the like.

For the purpose of implementing the present invention, it is useful to discretize a desired trajectory into a number of "control points" at various locations along the trajectory. A set of motion axis positions can be associated with each such control point. A desired trajectory may define a set of available control points. One way to specify a trajectory of radiation source 12 and/or beam 14 is to specify at a set of discrete control points at which the position of each motion axis is defined.

Figure 2:
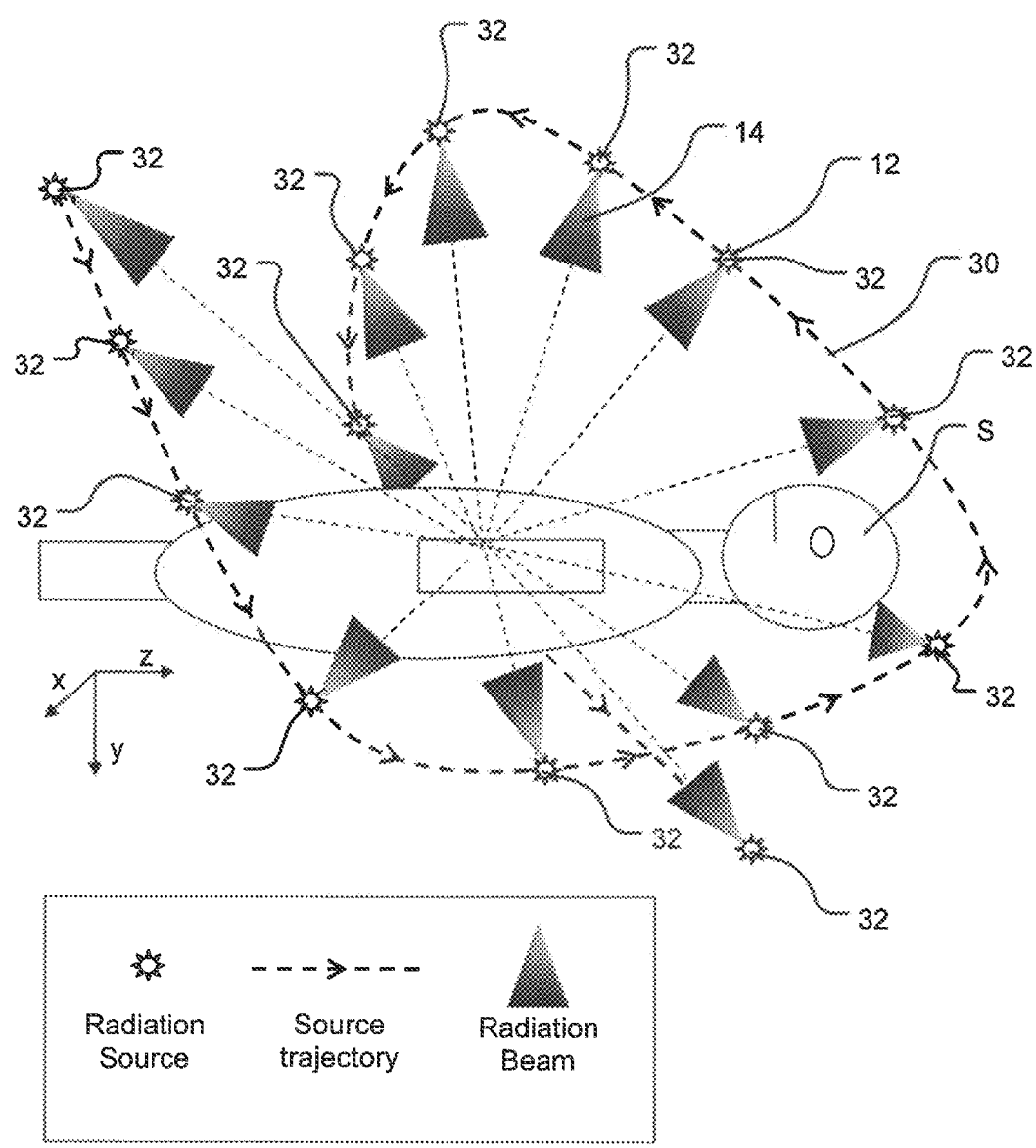
FIG. 2 is a schematic illustration of a trajectory.

FIG. 2 schematically depicts a radiation source 12 travelling relative to a subject S along an arbitrary trajectory 30 in three-dimensions while delivering radiation dose to a subject S by way of a radiation beam 14. The position and orientation of radiation beam 14 changes as source 12 moves along trajectory 30. In some embodiments, the changes in position and/or direction of beam 14 may occur substantially continuously as source 12 moves along trajectory 30. While source 12 is moving along trajectory 30, radiation dose may be provided to subject S continuously (i.e. at all times during the movement of source 12 along trajectory 30) or intermittently (i.e. radiation may be blocked or turned off at some times during the movement of source 12 along trajectory 30). Source 12 may move continuously along trajectory 30 or may move intermittently between various positions on trajectory 30. FIG. 2 schematically depicts a number of control points 32 along trajectory 30. In some embodiments, the specification of trajectory 30 defines the set of available control points 32. In other embodiments, the set of control points 32 are used to define trajectory 30. In such embodiments, the portions of trajectory 30 between control points 32 may be determined (e.g. by control system 23) from control points 32 by a suitable algorithm.

In general, control points 32 may be specified anywhere along trajectory 30, although it is preferable that there is a control point at the start of trajectory 30, a control point at the end of trajectory 30 and that the control points 32 are otherwise spaced-apart along trajectory 30. In some embodiments of the invention, control points 32 are selected such that the magnitudes of the changes in the position of a motion axis over a trajectory 30 are equal as between control points 32. For example, where a trajectory 30 is defined as a 360° arc of gantry 16 about axis 18 and where the number of control points 32 along trajectory 30 is 21, then control points 32 may be selected to correspond to 0° (a starting control point), 360° (an ending control point) and 19 other control points at 18° intervals along the arc of gantry 16.

Although trajectory 30 may be defined arbitrarily, it is preferable that source 12 and/or beam 14 not have to move back and forth along the same path. Accordingly, in some embodiments, trajectory 30 is specified such that it does not overlap itself (except possibly at the beginning and end of trajectory 30). In such embodiments, the positions of the motion axes of the radiation delivery apparatus are not the same except possibly at the beginning and end of trajectory 30. In such embodiments, treatment time can be minimized (or at least reduced) by irradiating subject S only once from each set of motion axis positions.

In some embodiments, trajectory 30 is selected such that the motion axes of the radiation delivery device move in one direction without having to reverse directions (i.e. without source 12 and/or beam 14 having to be moved back and forth along the same path). Selection of a trajectory 30 involving movement of the motion axes in a single direction can minimize wear on the components of a radiation delivery apparatus. For example, in apparatus 10, it is preferable to move gantry 16 in one direction, because gantry 16 may be relatively massive (e.g. greater than 1 ton) and reversing the motion of gantry 16 at various locations over a trajectory may cause strain on the components of radiation delivery apparatus 16 (e.g. on the drive train associated with the motion of gantry 16).

In some embodiments, trajectory 30 is selected such that the motion axes of the radiation delivery apparatus move substantially continuously (i.e. without stopping). Substantially continuous movement of the motion axes over a trajectory 30 is typically preferable to discontinuous movement, because stopping and starting motion axes can cause wear on the components of a radiation delivery apparatus. In other embodiments, the motion axes of a radiation delivery apparatus are permitted to stop at one or more locations along trajectory 30. Multiple control points 32 may be provided at such locations to allow the beam shape and/or beam intensity to be varied while the position and orientation of the beam is maintained constant.

In some embodiments, trajectory 30 comprises a single, one-way, continuous 360° rotation of gantry 16 about axis 18 such that trajectory 30 only possibly overlaps itself at its beginning and end points. In some embodiments, this single, one-way, continuous 360° rotation of gantry 16 about axis 18 is coupled with corresponding one-way, continuous translational or rotational movement of couch 15, such that trajectory 30 is completely non-overlapping.

Some embodiments involve trajectories 30 which are effected by any combination of motion axes of radiation delivery apparatus 10 such that relative movement between source 12 and/or beam 13 and subject S comprises a discrete plurality of arcs, wherein each arc is confined to a corresponding plane (e.g. a rotation of up to 360° of gantry 16 about axis 18). In some embodiments, each arc may be non-self overlapping. In some embodiments, each arc may overlap only at its beginning and end points. In the course of following such a trajectory 30, the motion axes of radiation delivery apparatus 10 may be moved between individual arcs such that the corresponding planes to which the arcs are confined intersect with one another (e.g. by suitable rotation of couch 15 about axis 22). Alternatively, the motion axes of radiation delivery apparatus 10 may be moved between individual arcs such that the corresponding planes to which the arcs are defined are parallel with one another (e.g. by suitable translational movement of couch 15). In some cases, radiation may not be delivered to subject S when the motion axes of radiation delivery apparatus 10 are moved between individual arcs.

Radiation delivery apparatus, such as exemplary apparatus 10 (FIG. 1) and 10A (FIG. 1A), typically include adjustable beam-shaping mechanisms 33 located between source 12 and subject S for shaping radiation beam 14. FIG. 3A schematically depicts a beam-shaping mechanism 33 located between source 12 and subject S. Beam-shaping mechanism 33 may comprise stationary and/or movable metal components 31. Components 31 may define an aperture 31A through which portions of radiation beam 14 can pass. Aperture 31A of beam-shaping mechanism 33 may define a two-dimensional border of radiation beam 14. In particular embodiments, beam shaping mechanism 33 is located and/or shaped such that aperture 31A is in a plane orthogonal to the direction of radiation from source 12 to the target volume in subject S. Control system 23 is preferably capable of controlling the configuration of beam-shaping mechanism 33.

One non-limiting example of an adjustable beam-shaping mechanism 33 comprises a multi-leaf collimator (MLC) 35 located between source 12 and subject S. FIG. 3B schematically depicts a suitable MLC 35. As shown in FIG. 3B, MLC 35 comprises a number of leaves 36 that can be independently translated into or out of the radiation field to define one or more apertures 38 through which radiation can pass. Leaves 36, which may comprise metal components, function to block radiation. In the illustrated embodiment, leaves 36 are translatable in the leaf-translation directions indicated by double-headed arrow 41. Leaf-translation directions 41 may be located in a plane that is orthogonal to beam axis 37 (i.e. a direction of the radiation beam 14 from source 12 to the target volume in subject S). In the FIG. 3B view, beam axis 37 extends into and out of the page. The size(s) and shape(s) of aperture(s) 38 may be adjusted by selectively positioning each leaf 36.

As shown in the illustrate embodiment of FIG. 3B, leaves 36 are typically provided in opposing pairs. MLC 35 may be mounted so that it can be rotated to different orientations about beam axis 37—i.e. such that leaf-translation directions 41 and the direction of movement of leaves 36 may be pivoted about beam axis 37. Dotted outline 39 of FIG. 3B shows an example of an alternate orientation of MLC 35 wherein MLC 35 has been rotated about beam axis 37 such that leaf-translation directions 41 are oriented at an angle that is approximately 45° from the orientation shown in the main FIG. 3B illustration.

It will be appreciated that the angle $\varphi$ of leaf-translation directions 41 about beam axis 37 may be defined relative to an arbitrary reference axis. FIG. 3C schematically depicts a system for defining the angle $\varphi$ of leaf-translation directions 41 about beam axis 37. In the FIG. 3C, the angle $\varphi$ of leaf-translation directions 41 about beam axis 37 is defined to be an angle in a range of $-90°<\varphi<=90°$ relative to a reference axis 43. FIG. 3C illustrates a first leaf-translation direction 41A wherein the angle $\varphi A$ is greater than zero and a second leaf-translation direction 41B wherein the angle $\varphi B$ is less than zero. The angle $\varphi$ of leaf-translation directions 41 about beam axis 37 (as defined relative to reference axis 43 in the above-described manner) may be referred to as the MLC orientation angle $\varphi$. In particular embodiments, the reference axis 43 may be selected to coincide with the direction of motion of beam axis 37 as beam positioning mechanism 13 moves source 12 and/or beam 14 relative to subject S along trajectory 30. Reference axis 43 may therefore be referred to herein as source trajectory direction 43.

A configuration of MLC 35 can be specified by a set of leaf positions that define a position of each leaf 36 and an MLC orientation angle $\varphi$ of MLC 35 about beam axis 37. The control system of a radiation delivery device (e.g. control system 23 of radiation delivery device 10) is typically capable of controlling the positions of leaves 36 and the MLC orientation angle $\varphi$. MLCs can differ in design details, such as the number of leaves 36, the widths of leaves 36, the shapes of the ends and edges of leaves 36, the range of positions that any leaf 36 can have, constraints on the position of one leaf 36 imposed by the positions of other leaves 36, the mechanical design of the MLC, and the like. The invention described herein should be understood to accommodate any type of configurable beam-shaping apparatus 33 including MLCs having these and other design variations.

The configuration of MLC 35 may be changed (for example, by moving leaves 36 and/or rotating the MLC orientation angle $\varphi$ of MLC 35 about beam axis 37) while radiation source 12 is operating and while radiation source 12 is moving about trajectory 30, thereby allowing the shape of aperture(s) 38 to be varied dynamically while radiation is being delivered to a target volume in subject S. Since MLC 35 can have a large number of leaves 36, each of leaves 36 can be placed in a large number of positions and MLC 35 can be rotated about beam axis 37, MLC 35 may have a very large number of possible configurations.

Figure 4A:
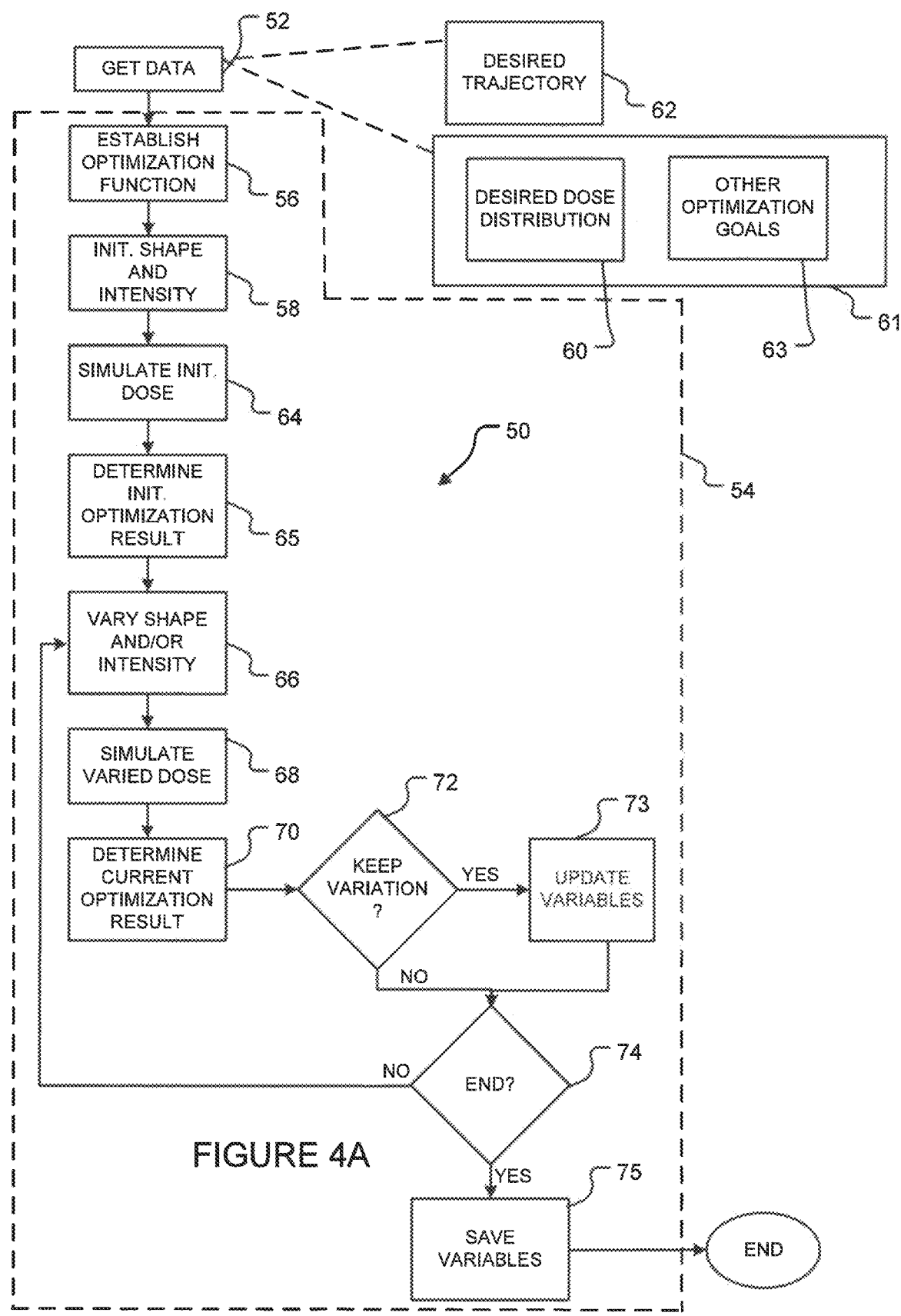
FIG. 4A is a flow chart illustrating a method of optimizing dose delivery according to a particular embodiment of the invention.

FIG. 4A schematically depicts a method 50 according to an example embodiment of this invention. An objective of method 50 is to establish a radiation treatment plan that will deliver a desired radiation dose distribution to a target volume in a subject S (to within an acceptable tolerance), while minimizing the dose of radiation delivered to tissues surrounding the target volume or at least keeping the dose delivered to surrounding tissues below an acceptable threshold. This objective may be achieved by varying: (i) a cross-sectional shape of a radiation beam (e.g. beam 14); and (ii) an intensity of the radiation beam, while moving radiation source 12 and/or beam 14 along a trajectory 30 relative to subject S. In some embodiments, as discussed above, these objectives are achieved while radiation source 12 and/or beam 14 are caused to move continuously along trajectory 30.

Method 50 may be performed, at least in part, by a treatment planning system 25 (e.g. treatment planning system 25 of FIG. 1). In the illustrated embodiment, treatment planning system 25 comprises its own controller 25A which is configured to execute suitable software 25B. In other embodiments, control system 23 and treatment planning system 25 may share a controller. Controller 25 may comprise one or more data processors, together with suitable hardware, including, by way of non-limiting example: accessible memory, logic circuitry, drivers, amplifiers, A/D and D/A converters and like. Such a controller may comprise, without limitation, a microprocessor, a computer-on-a-chip, the CPU of a computer or any other suitable microcontroller. Controller 25 may comprise a plurality of data processors.

A desired amount of radiation dose to be delivered to the target volume (referred to as the "desired dose distribution") and a suitable trajectory 30 may be defined in advance. Method 50 derives the shape that beam 14 ought to have during movement of source 12 and/or beam 14 along trajectory 30 and the intensity with which radiation ought to be delivered during movement of source 12 and/or beam 14 along trajectory 30. The shape of beam 14 may be determined by a suitable configuration of a beam-shaping mechanism 33, such as MLC 35.

In block 52, method 50 obtains a set of optimization goals 61 and trajectory data 62 defining a desired trajectory 30. Optimization goals 61 comprise dose distribution data 60, which defines a desired dose distribution, and may comprise other optimization goals 63. Optimization goals 61 and/or trajectory data 62 may have been developed by health professionals, such as a radiation oncologist in consultation with a radiation physicist, for example. Optimization goals 61 and/or trajectory data 62 may be specified by an operator as a part of block 52.

The person or persons who develop trajectory 30 may have reference to factors such as:
the condition to be treated;
the shape, size and location of the target volume;
the locations of critical structures that should be spared; and
other appropriate factors.

Trajectory 30 may be selected to minimize treatment time.

Radiation delivery apparatus according to some embodiments of the invention may provide one or more pre-defined trajectories. For example, in some embodiments, a pre-defined trajectory 30 may comprise a single, one-way, continuous 360° rotation of gantry 16 about axis 18 such that trajectory 30 overlaps itself only at its beginning and end points. In such cases, block 52 may comprise selecting a pre-defined trajectory 30 or a template that partially defines a trajectory 30 and can be completed to fully define the trajectory 30.

As discussed above, optimization goals 61 comprise dose distribution data 60 and may comprise other optimization goals 63. Other optimization goals 63 may be specified by an operator as a part of block 52. By way of non-limiting example, other optimization goals 63 may comprise a desired uniformity of dose distribution in the target volume (or a desired precision with which the dose distribution in the target volume should match desired dose distribution data 60). Other optimization goals 63 may also define volumes occupied by important structures outside of the target volume and set limits on the radiation doses to be delivered to those structures. Other optimization goals 63 may define a maximum time required to deliver the radiation based on an individual patient's ability to stay still during treatment. For example, a child may be more likely to move during treatment than an adult and such movement may cause incorrect dose delivery. Consequently, it may be desirable to lower the maximum dose delivery time for the child to minimize the risk that the child may move during treatment. Other optimization goals 63 may also set priorities (weights) for different optimization goals.

Other optimization goals 63 may have any of a variety of different forms. For example, a biological model may be used in the computation of a metric which estimates a probability that a specified dose distribution will control a disease from which the subject is suffering and/or the probability that a specified dose delivered to non-diseased tissue may cause complications. Such biological models are known as radiobiological models. Other optimization goals 63 may be based in part on one or more radiobiological models. The physical limitations of a particular radiation delivery apparatus may also be taken into account as another example of an optimization goal 63. As mentioned above, gantry 12 can be relatively massive and controlled movement of gantry 12 may be difficult and may cause strain to various components of the radiation delivery apparatus. As a particular example, one optimization goal 63 may be to have gantry 16 move continuously (i.e. without stopping) over the specified trajectory 30.

Method 50 then proceeds to an optimization process 54, which seeks desirable beam shapes and intensities as a function of the position of source 12 and/or beam 14 along trajectory 30. In the illustrated embodiment of method 50, optimization process 54 involves iteratively selecting and modifying one or more optimization variables affecting the beam shape or the beam intensity. For example, the optimization variable(s) may comprise a position of a leaf 36 in a MLC 35 at a control point 32 (which determines a shape of beam 14), a MLC orientation angle $\varphi$ of MLC 35 about axis 37 at a control point 32 (which determines a shape of beam 14) and/or an intensity of beam 14 at a control point 32. The quality of the dose distribution resulting from the modified optimization variable(s) is evaluated in relation to a set of one or more optimization goals. The modification is then accepted or rejected. Optimization process 54 continues until it achieves an acceptable set of beam shapes and intensities or fails.

In the illustrated method 50, optimization process 54 begins in block 56 by establishing an optimization function. The block 56 optimization function is based, at least in part, on optimization goals 61. The set of optimization goals 61 includes the desired dose distribution data 60 and may include one or more other optimization goals 63. The block 56 optimization function may comprise a cost function. Higher costs (corresponding to circumstances which are farther from optimization goals 61) may be associated with factors such as:
- deviations from the desired dose distribution data 60;
- increases in the radiation dose delivered outside of the target volume;
- increases in the radiation dose delivered to critical structures outside of the treatment volume;
- increases in the time required to deliver the radiation treatment; and/or
- increases in the total radiation output required for the delivery of the treatment.

Lower costs (corresponding to circumstances which are closer to optimization goals 61) may be associated with factors such as:
- radiation doses that come closer to matching specified thresholds (which may be related to desired dose distribution data 60);
- no radiation doses exceeding specified thresholds;
- reductions in radiation dose outside of the target volume;
- reductions in radiation dose delivered to critical structures outside of the target volume;
- decreases in the time required to deliver the radiation treatment; and/or
- decreases in the total radiation output required for the delivery of the treatment.

These factors may be weighted differently from one another. Other factors may also be taken into account when establishing the block 56 optimization function.

The result of block 56 is an optimization function which takes as input a dose distribution and produces an output having a value or values that indicate how closely the input dose distribution satisfies a set of optimization goals 61.

Block 58 involves initializing beam shapes and intensities for a number of control points 32 along trajectory 30. The initial beam shapes and intensities may be selected using any of a wide variety of techniques. Initial beam shapes may be selected by specifying a particular configuration of MLC 35. By way of non-limiting example, initial beam shapes specified in block 58 may be selected by any of:
- setting the beam shape at each control point 32 along trajectory 30 to approximate a beam's eye view outline of the target volume (taken from control point 32);
- setting the beam shape so that radiation is blocked from healthy tissue structures only;
- initializing leaves 36 of MLC to be in a specified configuration such as fully open, fully closed, half-open, or defining a shape for aperture 38 (e.g. round, elliptical, rectangular or the like); and
- randomizing the positions of leaves 36 of MLC. The particular way that the beam shapes are initialized is not critical and is limited only by the beam-shaping mechanism 33 of particular radiation delivery apparatus.

By way of non-limiting example, the initial beam intensities specified in block 58 may be selected by any of:
- setting all intensities to zero;
- setting all intensities to the same value; and
- setting intensities to random values.

In some embodiments, the beam shapes are initialized in block 58 to shapes that match a projection of the target (e.g. to approximate a beam's eye view outline of the target volume from each control point 32 along trajectory 30) and the intensities are initialized in block 58 to all have the same value which may be set so that the mean dose in the target volume will equal a prescribed dose.

In block 64, method 50 involves simulating the dose distribution resulting from the initial beam shapes and initial beam intensities. Typically, the block 64 simulation comprises a simulated dose distribution computation which is discussed in more detail below. Method 50 then determines an initial optimization result in block 65. The block 65 determination of the initial optimization result may comprise evaluating the block 56 optimization function on the basis of the block 64 simulated dose distribution.

In block 66, method 50 alters the beam shapes and/or intensities at one or more control points 32. The block 66 alteration of beam shapes and/or intensities may be quasi-random. The block 66 alteration of beam shapes and/or intensities may be subject to constraints. For example, such constraints may prohibit impossible beam shapes and/or intensities and may set other restrictions on beam shapes, beam intensities and/or the rate of change of beam shapes and/or beam intensities. In each execution of block 66, the alteration of beam shapes and/or intensities may involve a single parameter variation or multiple parameter variations to beam shape parameter(s) and/or to beam intensity parameter(s). The block 66 alteration of beam shapes and/or intensities and may involve variation(s) of these parameter(s) at a single control point 32 or at multiple control points 32. Block 68 involves simulating a dose distribution that would be achieved if the block 66 altered beam shapes and/or intensities were used to provide a radiation treatment. Typically, the block 68 simulation comprises a simulated dose distribution computation which is discussed in more detail below.

In some embodiments, the block 66 alteration of beam shapes and/or intensities is not chosen randomly, but rather is selected to give priority to certain parameter(s) that have large impacts on dose distribution quality. "Dose distribution quality" may comprise a reflection of how closely a simulated dose distribution calculation meets optimization goals 61. For example, where the beam is shaped by a MLC 35, certain leaves 36 or positions of leaves 36 may be given priority for modification. This may be done by determining a priori which leaves of MLC 35 have the most impact on dose distribution quality. Such an a priori determination of particularly important MLC leaves may be based, for example, on a calculation of the relative contributions to the block 56 optimization function from each voxel in the target region and the surrounding tissue and by a projection of beam ray lines intersecting a particular voxel to the plane of MLC 35.

In block 70, method 50 determines a current optimization result. The block 70 determination may comprise evaluating the block 56 optimization function on the basis of the block 68 simulated dose distribution. In block 72, the current optimization result (determined in block 70) is compared to a previous optimization result and a decision is made whether to keep or discard the block 66 alteration. The first time that method 50 arrives at block 72, the previous optimization result may be the block 65 initial optimization result. The block 72 decision may involve:

(i) deciding to preserve the block 66 alteration (block 72 YES output) if the current optimization result is closer to optimization goals 61 than the previous optimization result; or (ii) deciding to reject the block 66 alteration (block 72 NO output) if the current optimization result is further from optimization goals 61 than the previous optimization result.

Other optimization algorithms may make the block 72 decision as to whether to keep or discard the block 66 alteration based on rules associated with the particular optimization algorithm. For example, such optimization algorithms may, in some instances, allow preservation of the block 66 alteration (block 72 YES output) if the current optimization result is further from the optimization goals 61 than the previous optimization result. Simulated annealing is an example of such an optimization algorithm.

If block 72 determines that the block 66 alteration should be preserved (block 72 YES output), then method 50 proceeds to block 73, where the block 66 altered beam shapes and intensities are updated to be the current beam shapes and intensities. After updating the beam shapes and intensities in block 73, method 50 proceeds to block 74. If block 72 determines that the block 66 alteration should be rejected (block 72 NO output), then method 50 proceeds directly to block 74 (i.e. without adopting the block 66 alterations).

Block 74 involves a determination of whether applicable termination criteria have been met. If the termination criteria have been met (block 74 YES output), method 50 proceeds to block 75, where the current beam shapes and intensities are saved as an optimization result. After block 75, optimization process 54 terminates. On the other hand, if the termination criteria have not been met (block 74 NO output), method 50 loops back to perform another iteration of blocks 66 through 74.

By way of non-limiting example, block 74 termination criteria may include any one or more of:
successful achievement of optimization goals 61;
successive iterations not yielding optimization results that approach optimization goals 61;
number of successful iterations of blocks 66 through 74 (where a successful iteration is an iteration where the block 66 variation is kept in block 73 (i.e. block 72 YES output));
operator termination of the optimization process.

The illustrated method 50 represents a very simple optimization process 54. Optimization process 54 may additionally or alternatively include other known optimization techniques such as:
simulated annealing;
gradient-based techniques;
genetic algorithms;
applying neural networks; or
the like.

Figure 4B:
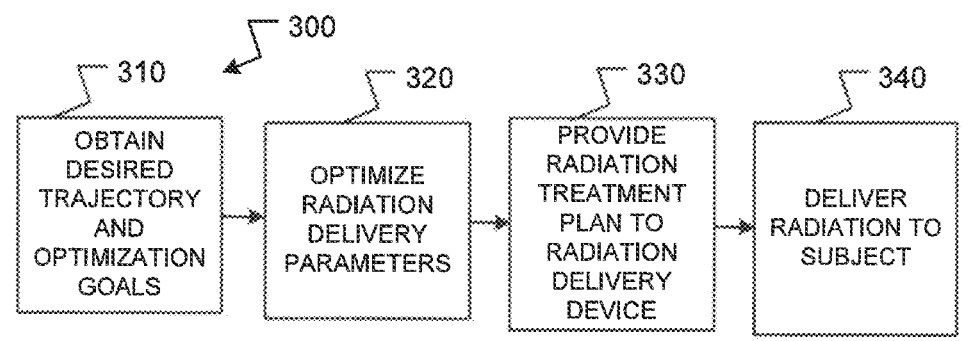
FIG. 4B is a schematic flow chart depicting a method for planning and delivering radiation to a subject according to a particular embodiment of the invention.

Method 50 may be used as a part of an overall method for planning and delivering radiation dose to a subject S. FIG. 4B schematically depicts a method 300 for planning and delivering radiation dose to a subject S according to a particular embodiment of the invention. Method 300 begins in block 310, which, in the illustrated embodiment, involves obtaining a desired trajectory 30 and desired optimization goals 61. Method 300 then proceeds to block 320 which involves optimizing a set of radiation delivery parameters. In one particular embodiment, the block 320 optimization process may comprise an optimization of the beam shape and beam intensity parameters in accordance with optimization process 54 of method 50. The result of the block 320 optimization process is a radiation delivery plan. In block 330, the radiation delivery plan is provided to the control system of a radiation delivery apparatus (e.g. control system 23 of radiation delivery device 10 (FIG. 1)). In block 340, the radiation delivery apparatus delivers the radiation to a subject in accordance with the radiation treatment plan developed in block 320.

Method 50 involves the simulation of dose distribution that results from a particular set of beam shapes, beam intensities and motion axis positions (e.g. in blocks 64 and 68). Simulation of the dose distribution may be performed in any suitable manner. Some examples of dose calculation methods that may be employed to simulate dose distribution results comprise:

pencil beam superposition;
collapsed cone convolution; and
Monte Carlo simulation.

In some embodiments, the dose that would be delivered by a treatment plan is simulated (as in blocks 64 and 68 of method 50) by adding a contribution to the dose from each control point 32. At each of control points 32, the following information is known:

a position of source 12 and an orientation of beam 14 relative to subject S including the target volume (as determined by the positions of the available motion axes);
a beam shape (as determined, for example, by a MLC orientation angle φ and/or a configuration of the leaves 36 of a MLC 35); and
a beam intensity.

In some embodiments, the contribution to the dose at each control point 32 is determined by pencil beam superposition. Pencil beam superposition involves conceptually dividing the projected area of beam 14 into many small beams known as "beamlets" or "pencil beams". This may be done by dividing a cross-sectional beam shape (e.g. aperture 38 of MLC 35) into a grid of square beamlets. The contribution to an overall dose distribution from a particular control point 32 may be determined by summing the contributions of the beamlets. The contribution to a dose distribution by individual beamlets may be computed in advance. Such contributions typically take into account radiation scattering and other effects that can result in the radiation from one beamlet contributing to dose in regions that are outside of the beamlet. In a typical MLC 35, there is some transmission of radiation through leaves 36. Consequently, when performing a dose simulation calculation, it is often desirable add some smaller contribution to the dose from outside of the beam shaping aperture 38 to account for transmission through leaves 36 of MLC 35.

FIG. 5A shows an aperture 38 of an MLC 35 divided into a plurality of beamlets 80. In general, it is desirable for beamlets 80 to be fairly small to permit precise modelling of the wide range of configurations that aperture 38 may have. Beamlets 80 may be smaller than the widths of the leaves 36 (not shown in FIG. 5A) of MLC 35. In FIG. 5A, 105 beamlets 80 are required to cover aperture 38 and, consequently, for a particular control point 32 having the aperture configuration shown in FIG. 5A, a dose simulation calculation (e.g. a portion of the block 68 dose simulation) involves a superposition of the dose contributed by 105 beamlets 80.

Some embodiments achieve efficiencies in this dose simulation computation by providing composite beamlets 82 that are larger than beamlets 80. A range of composite beamlets 82 having different sizes, shapes and/or orientations may be provided. FIG. 5B shows a number of composite beamlets 82A, 82B, 82C (collectively, beamlets 82) having different sizes and shapes. It can be seen from FIG. 5B, that composite beamlets 82 can be used in the place of a plurality of conventionally sized beamlets 80. An example application of composite beamlets 82 is shown in FIG. 5C. For a given shape of aperture 38, composite beamlets 82 are used in place of some or all of smaller beamlets 80. In the particular configuration of aperture 38 of FIG. 5C (which is the same as the configuration of aperture 38 of FIG. 5A), the area of aperture 38 is covered by 28 composite beamlets 82 (24 82A, one 84B, three 84C) and one smaller beamlet 80. Consequently, for a particular control point 32 having the aperture configuration of FIG. 5B, a dose simulation calculation (e.g. a portion of the block 68 dose simulation) is reduced to a superposition of the dose contributed by 29 beamlets 82, 80. Dose contributed by composite beamlets 82 may be determined in advance in a manner similar to the advance dose contribution from conventional beamlets 80.

The size and shape of composite beamlets 82 may be selected to reduce, and preferably minimize, the number of beamlets required to cover the area of aperture 38. This can significantly reduce calculation time without significantly reducing the accuracy of dose simulation. The use of composite beamlets is not limited to pencil beam superposition and may be used in other dose simulation calculation algorithms, such as Monte Carlo dose simulation and collapsed cone convolution dose simulation, for example.

The use of composite beamlets 82 to perform a dose simulation calculation assumes that there are only small changes in the characteristics of the tissue over the cross-sectional dimension of the composite beamlet 82. As composite beamlets are made larger, this assumption may not necessarily hold. Accordingly, the upper size limit of composite beamlets 82 is limited by the necessary calculation accuracy. In some embodiments, at least one dimension of composite beamlets 82 is greater than the largest dimension of conventional beamlet 80. In some embodiments, the maximum dimension of composite beamlets 82 is less than 25 times the size of the largest dimension of conventional beamlet 80.

The dose simulation computation (e.g. the block 68 dose simulation) is performed at a number of control points 32. Based on calculations for those control points 32, an estimated dose distribution is generated for a radiation source 12 that may be continuously moving over a trajectory 30 and continuously emitting a radiation beam 14, where the radiation beam 14 may have a continuously varying shape and intensity. Where a dose distribution is computed by summing contributions from discrete control points 32, the accuracy with which the computed dose will match the actual dose delivered by continuous variation of the position of source 12, the orientation of beam 14, the beam shape and the beam intensity will depend in part upon the number of control points 32 used to perform the dose simulation computation. If there are only a few control points 32, then it may not be possible to obtain accurate estimates of the delivered dose. The dose delivered by source 12 over a continuous trajectory 30 can be perfectly modelled by summing contributions from discrete control points 32 only at the limit where the number of control points 32 approaches infinity. Discretization of the dose simulation calculation using a finite number of control points 32 will therefore degrade the accuracy of the modelled dose distribution.

Figure 6:
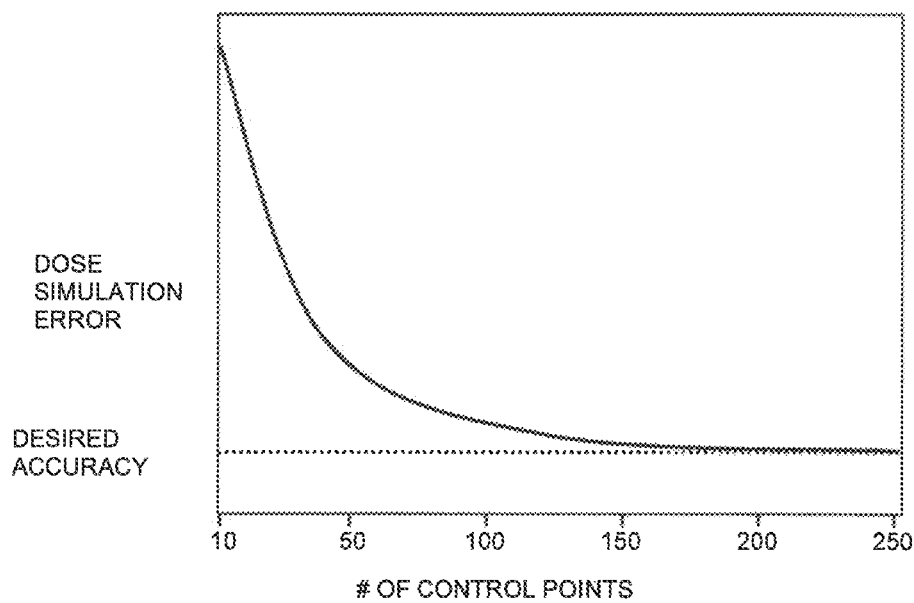
FIG. 6 graphically depicts the error associated with a dose simulation calculation versus the number of control points used to perform the dose simulation calculation.

This concept is graphically illustrated in FIG. 6, which plots the dose simulation error against the number of control points 32. FIG. 6 clearly shows that where the dose simulation computation makes use of a large number of control points 32, the resultant error (i.e. the difference between simulation dose distribution and actual dose distribution) is minimized.

In some embodiments of the invention, constraints are imposed on the optimization process (e.g. block 54 of method 50). Such constraints may be used to help maintain the accuracy of the discretized dose simulation calculation to within a given tolerance. In some embodiments, these optimization constraints are related to the amount of change in one or more parameters that may be permitted between successive control points 32. Examples of suitable constraints include:

- Radiation source 12 cannot travel further than a maximum distance between consecutive control points 32. This may be achieved entirely, or in part, by imposing a maximum change in any motion axis between consecutive control points 32. Separate constraints may be provided for each motion axis. For example, a maximum angular change may be specified for gantry angle, maximum changes in displacement may be provided for couch translation etc.
- Parameters affecting beam shape cannot change by more than specified amounts between consecutive control points 32. For example, maximum values may be specified for changes in the positions of leaves 36 of a MLC 35 or changes in MLC orientation angle $\varphi$ of MLC 35.
- Parameters affecting beam shape cannot change by more than a specified amount per unit of motion axis change. For example, maximum values may be specified for changes in the positions of leaves 36 of a MLC 35 for each degree of rotation of gantry 16 about axis 18.
- The source intensity cannot change by more than a specified amount between control points 32.
- The source intensity cannot change by more that a specified amount per unit of motion axis change.
- The source intensity cannot exceed a certain level.

It will be appreciated that where a dose simulation calculation is based on a number of discretized control points, constraints which force small changes of motion axes parameters, beam shape parameters and/or beam intensity parameters between control points can produce more accurate dose simulation calculations.

In addition to improving the accuracy of the dose simulation calculation, the imposition of constraints may also help to reduce total treatment time by accounting for the physical limitations of particular radiation delivery apparatus. For example, if a particular radiation delivery apparatus has a maximum radiation output rate and the optimization solution generated by method 50 involves a desired radiation intensity that results in a radiation output rate higher than this maximum radiation output rate, then the rate of movement of the motion axes of the radiation delivery apparatus will have to slow down in order to deliver the intensity prescribed by the block 54 optimization process. Accordingly, a constraint imposed on the maximum source intensity during the block 54 optimization can force a solution where the prescribed intensity is within the capability of the radiation delivery apparatus (e.g. less than the maximum radiation output rate of the radiation delivery apparatus) such that the motion axes of the radiation delivery apparatus do not have to slow down. Since the motion axes do not have to slow down, such a solution can be delivered to subject S relatively quickly, causing a corresponding reduction in total treatment time. Those skilled in the art will appreciate that other constraints may be used to account for other limitations of particular radiation delivery apparatus and can be used to reduce total treatment time.

An example of how such constraints may be defined is "For an estimated dose to be within 2% of the actual dose distribution, the following parameters should not change by more than the stated amounts between any two consecutive control points 32:

intensity—10%;
MLC leaf position—5 mm;
MLC orientation $\varphi$—5%;
gantry angle—1 degree; and
couch position—3 mm."

Figure 7:
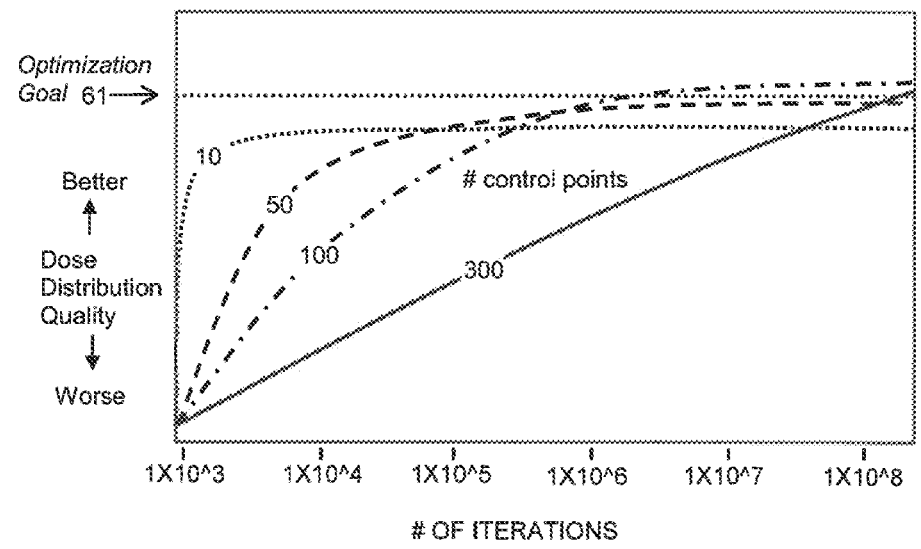
FIG. 7 graphically depicts dose quality versus the number of optimization iterations for several different numbers of control points.

The number of control points 32 used in optimization process 54 also impacts the number of iterations (and the corresponding time) required to implement optimization process 54 as well as the quality of the dose distribution. FIG. 7 graphically depicts the dose distribution quality as a function of the number of iterations involved in a block 54 optimization process for various numbers of control points 32.

FIG. 7 shows plots for 10 control points, 50 control points, 100 control points and 300 control points on a logarithmic scale. It will be appreciated by those skilled in the art that the number of iterations (the abscissa in FIG. 7) is positively correlated with the time associated to perform the optimization. FIG. 7 shows that when the number of control points 32 is relatively low, the quality of the dose distribution improves rapidly (i.e. over a relatively small number of iterations). However, when the number of control points 32 is relatively low, the quality of the resultant dose distribution is relatively poor and, in the cases of 10 control points and 50 control points, the quality of the dose distribution does not achieve the optimization goals 61. Conversely, if a relatively large number of control points 32 is used, the block 54 optimization requires a relatively large number of iterations, but the quality of the dose distribution eventually achieved is relatively high and exceeds the optimization goals 61. In some cases, where the number of control points 32 is relatively high, the number of iterations required to achieve a solution that meets the optimization goals 61 can be prohibitive (i.e. such a solution can take too long or can be too computationally expensive).

The impact of the number of control points 32 on the block 54 optimization process may be summarized as follows. If a relatively small number of control points 32 are used:

- there may be relatively large changes in the motion axes parameters (i.e. beam position and beam orientation), the beam shape parameters (e.g. positions of leaves 36 of MLC 35 and/or MLC orientation angle $\varphi$) and beam intensity between control points 32 (i.e. the constraints on the motion axes parameters, the beam shape parameters and the beam intensity will be relatively relaxed as between control points 32);
- because of the relatively relaxed constraints and the large range of permissible changes to the beam shape and intensity parameters, it is possible to explore a relatively large range of possible configurations of the beam intensity and beam shape during optimization process 54;
- because of the ability to explore a relatively large range of possible beam shape and intensity configurations, the block 54 optimization process will tend to approach the optimization goals 61 after a relatively small number of iterations;
- because there are fewer control points available at which the beam shape parameters and/or beam intensity parameters may be varied, it may be difficult or impossible for the block 54 optimization process to derive a dose distribution that meets or exceeds optimization goals 61; and the accuracy of dose simulation computations based on the relatively small number of control points 32 will be relatively poor and may be outside of an acceptable range.

If a relatively large number of control points 32 are used:
the possible magnitudes of the changes in the motion axes parameters (i.e. beam position and beam orientation), the beam shape parameters (e.g. positions of leaves 36 of MLC 35 and/or MLC orientation angle φ) and beam intensity between control points 32 are relatively low (i.e. the constraints on the motion axes parameters, the beam shape parameters and the beam intensity will be relatively restrictive as between control points 32);

because of the relatively restrictive constraints and the small range of permissible changes to the beam shape and intensity parameters, only a relatively small range of possible beam shape and beam intensity configurations may be explored during optimization process 54;

because of the limited range of possible beam shape and intensity configurations, it may take a relatively large number of iterations for the block 54 optimization process to approach the optimization goals 61;

because there are more control points available at which the beam shape and/or the beam intensity may be varied, it may be easier to derive a dose distribution that meets or exceeds optimization goals 61; and the accuracy of dose simulation computations based on the relatively large number of control points 32 will be relatively good.

In some embodiments, the benefits of having a small number of control points 32 and the benefits of having a large number of control points 32 are achieved by starting the optimization process with a relatively small number of control points 32 and then, after a number of initial iterations, inserting additional control points 32 into the optimization process. This process is schematically depicted in FIG. 8.

Figure 8:
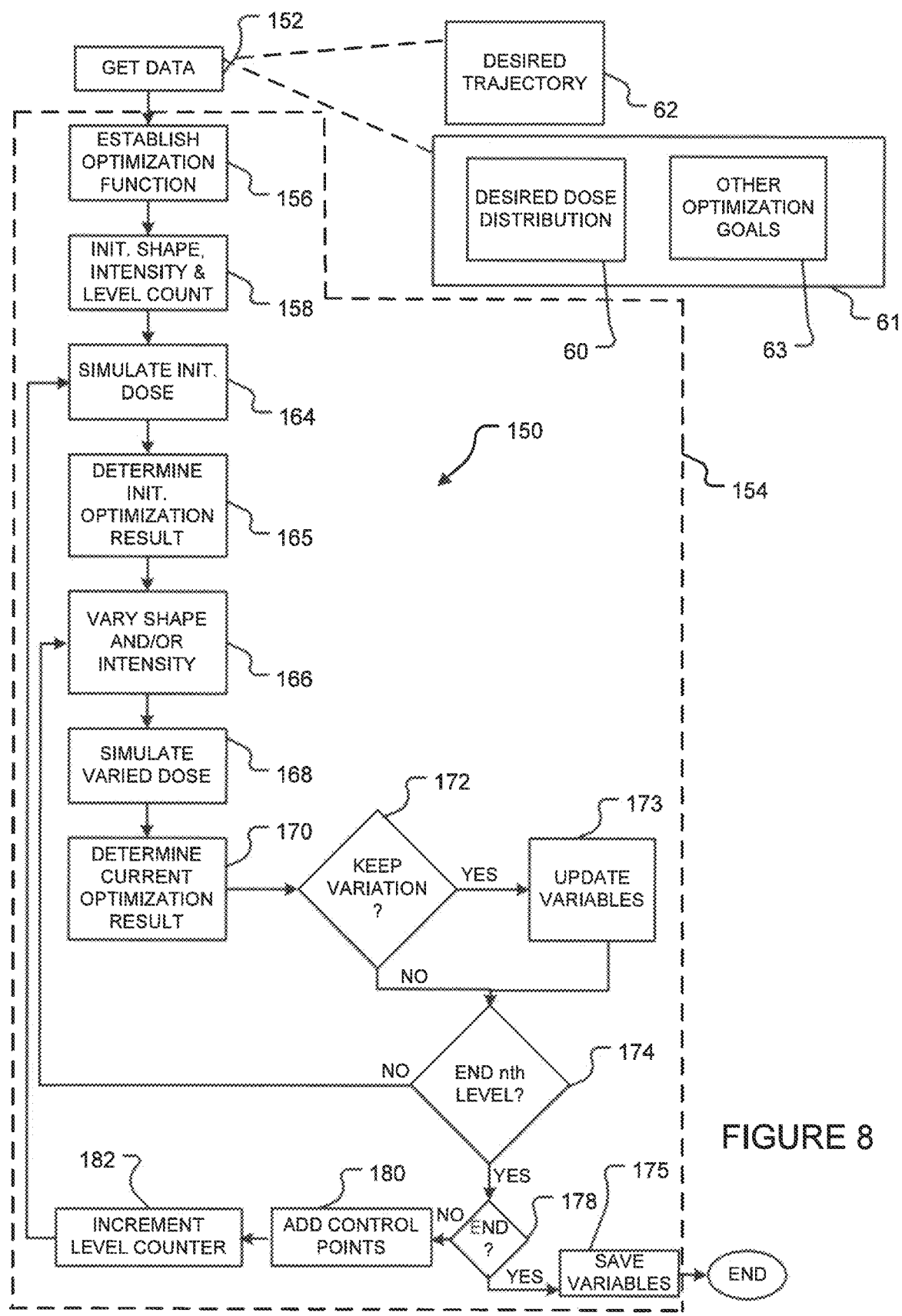
FIG. 8 represents a flow chart which schematically illustrates a method of optimizing dose delivery according to another embodiment of the invention where the number of control points is varied over the optimization process.

FIG. 8 shows a method 150 of optimizing dose delivery according to another embodiment of the invention. Method 150 of FIG. 8 may be used as a part of block 320 in method 300 of FIG. 4B. In many respects, method 150 of FIG. 8 is similar to method 50 of FIG. 4A. Method 150 comprises a number of functional blocks which are similar to those of method 50 and which are provided with reference numerals similar to the corresponding blocks of method 50, except that the reference numerals of method 150 are proceeded by the numeral "1". Like method 50, the objective of method 150 is to establish a radiation treatment plan that will deliver a desired radiation dose distribution to a target volume in a subject S (to within an acceptable tolerance), while minimizing the dose of radiation delivered to tissues surrounding the target volume or at least keeping the dose delivered to surrounding tissues below an acceptable threshold. This objective may be achieved by varying: (i) a cross-sectional shape of radiation beam 14; and (ii) an intensity of beam 14, while moving radiation source 12 and/or beam 14 along a trajectory 30 relative to subject S.

The principal difference between method 50 of FIG. 4A and method 150 of FIG. 8 is that the optimization process 154 of method 150 involves a repetition of the optimization process over a number of levels. Each level is associated with a corresponding number of control points 32 and the number of control points 32 increases with each successive level. In the illustrated embodiment, the total number of levels used to perform the block 154 optimization (or, equivalently, the final number of control points 32 at the conclusion of the block 154 optimization process) may be determined prior to commencing method 150. For example, the final number of control points 32 may be specified by an operator depending, for example, on available time requirements, accuracy requirements and/or dose quality requirements. In other embodiments, depending on termination conditions explained in more detail below, the final number of control points 32 may vary for each implementation of method 150.

Method 150 starts in block 152 and proceeds in the same manner as method 50 until block 158. In the illustrated embodiment, block 158 differs from block 58 in that block 158 involves the additional initialization of a level counter. In other respects, block 158 is similar to block 58 of method 50. Initialization of the level counter may set the level counter to 1 for example. When the level counter is set to 1, method 150 selects a corresponding level 1 number of control points 32 to begin the block 154 optimization process. The level 1 number of control points 32 is preferably a relatively low number of control points. In some embodiments, the level 1 number of control points 32 is in a range of 2-50. As discussed in more detail below, the level counter is incremented during the implementation of method 150 and each time the level counter is incremented, the corresponding number of control points 32 is increased.

Using a number of control points 32 dictated by the level counter, method 150 proceeds with blocks 164 through 174 in a manner similar to blocks 64 through 74 of method 50 discussed above. Block 174 differs from block 74 in that block 174 involves an inquiry into the termination conditions for a particular level of method 150. The termination conditions for a particular level of method 150 may be similar to the termination conditions in block 74 of method 50. By way of non-limiting example, the termination conditions for block 174 may comprise any one or more of:

successful achievement of optimization goals 61 to within a tolerance level which may be particular to the current level;

successive iterations not yielding optimization results that approach optimization goals 61; and operator termination of the optimization process.

Additionally or alternatively, the block 174 termination conditions may include reaching a maximum number of iterations of blocks 166 through 174 within a particular level of method 150 regardless of the resultant optimization quality. For example, the maximum number of iterations for level 1 may be $10^4$. The maximum number iterations may vary for each level. For example, the maximum number of iterations may increase for each level in conjunction with a corresponding increase in the number of control points 32 or may decrease for each level in conjunction with a corresponding increase in the number of control points 32.

Additionally or alternatively, the block 174 termination conditions may include reaching a maximum number of successful iterations of blocks 166 through 174 within a particular level of method 150 (i.e. iterations where method 150 proceeds through the block 172 YES output and the block 166 variation is kept in block 173). Again, the maximum number of successful iterations may vary (increase or decrease) for each level. In some embodiments, the maximum number of successful iterations within a particular level decreases as the level (i.e. the number of control points 32) increases. In one particular embodiment, the maximum number of successful iterations decreases exponentially as the level increases.

If the termination criteria have not been met (block 174 NO output), method 150 loops back to perform another iteration of blocks 166 through 174 at the current level. If the termination criteria have been met (block 174 YES output), method 150 proceeds to block 178, where method 150 inquires into the general termination conditions for optimization process 154. The general termination conditions of block 178 may be similar to the termination conditions in block 174, except the block 178 termination conditions pertain to optimization process 154 as a whole rather than to a particular level of optimization process 154. By way of non-limiting example, the termination conditions for block 178 may comprise any one or more of:
  successful achievement of optimization goals 61 to within a tolerance level particular to optimization process 154 as a whole;
  successive iterations not yielding optimization results that approach optimization goals 61; and
  operator termination of the optimization process.
Additionally or alternatively, the block 178 termination conditions may include reaching a suitable minimum number of control points 32. This minimum number of control points may depend on the number of control points 32 required to ensure that dose simulation calculations have sufficient accuracy (see FIG. 6).

The block 178 termination conditions may additionally or alternatively comprise having minimum threshold level(s) of control points 32 for corresponding changes in the motion axes parameters, the beam shape parameters and/or the beam intensity parameter. In one particular example, the block 178 termination conditions may comprise minimum threshold level(s) of at least one control point 32 for:
  each intensity change greater than 10%;
  each MLC leaf position change greater than 5 mm;
  each MLC orientation change greater than 5°;
  each gantry angle change greater than 1°; and/or
  each couch position change greater than −3 mm.

If the block 178 termination criteria have been met (block 178 YES output), method 150 proceeds to block 175, where the current beam shapes and intensities are saved as an optimization result. After block 175, method 150 terminates. On the other hand, if the block 178 termination criteria have not been met (block 178 NO output), method 150 proceeds to block 180, where the number of control points 32 is increased.

The addition of new control points 32 in block 180 may occur using a wide variety of techniques. In one particular embodiment, new control points 32 are added between pairs of existing control points 32. In addition to adding new control points 32, block 180 comprises initializing the parameter values associated with the newly added control points 32. For each newly added control point 32, such initialized parameter values may include: motion axes parameters which specify the position of source 12 and the orientation of beam 14 (i.e. the set of motion axis positions corresponding to the newly added control point 32); an initial beam shape parameter (e.g. the configuration of the leaves 36 and/or orientation φ of a MLC 35); and an initial beam intensity parameter.

The motion axes parameters corresponding to each newly added control point 32 may be determined by the previously specified trajectory 30 (e.g. by desired trajectory data 62). The initial beam shape parameters and the initial beam intensity parameters corresponding to each newly added control point 32 may be determined by interpolating between the current beam shape parameters and current beam intensity parameters for previously existing control points 32 on either side of the newly added control point 32. Such interpolation may comprise linear or non-linear interpolation for example.

The initial parameter values for the newly added control points 32 and the subsequent permissible variations of the parameter values for the newly added control points 32 may be subject to the same types of constraints discussed above for the original control points 32. For example, the constraints on the parameter values for newly added control points 32 may include:
  constraints on the amount that radiation source 12 (or any one or more motion axes) can move between control points 32;
  constraints on the amount that the beam shape can change between successive control points 32 (e.g. constraints on the maximum rotation MLC orientation φ or movement of the leaves 36 of MLC 35); or
  constraints on the amount that the intensity of source 12 may change between successive control points 32.
Those skilled in the art will appreciate that the magnitude of these optimization constraints will vary with the number of control points 32 and/or the separation of adjacent control points 32. For example, if the constraint on a maximum movement of a leaf 36 of MLC 35 is 2 cm between successive control points 32 when there are 100 control points 32 and the number of control points 32 is doubled to 200, the constraint may be halved, so that the constraint on the maximum movement of a leaf 36 of MLC 35 is 1 cm between control points 32 (assuming that the newly added control points 32 are located halfway between the existing control points 32).

After adding and initializing the new control points 32 in block 180, method 180 proceeds to block 182 where the level counter 182 is incremented. Method 150 then returns to block 164, where the iteration process of blocks 164 through 174 is repeated for the next level.

Figure 9:
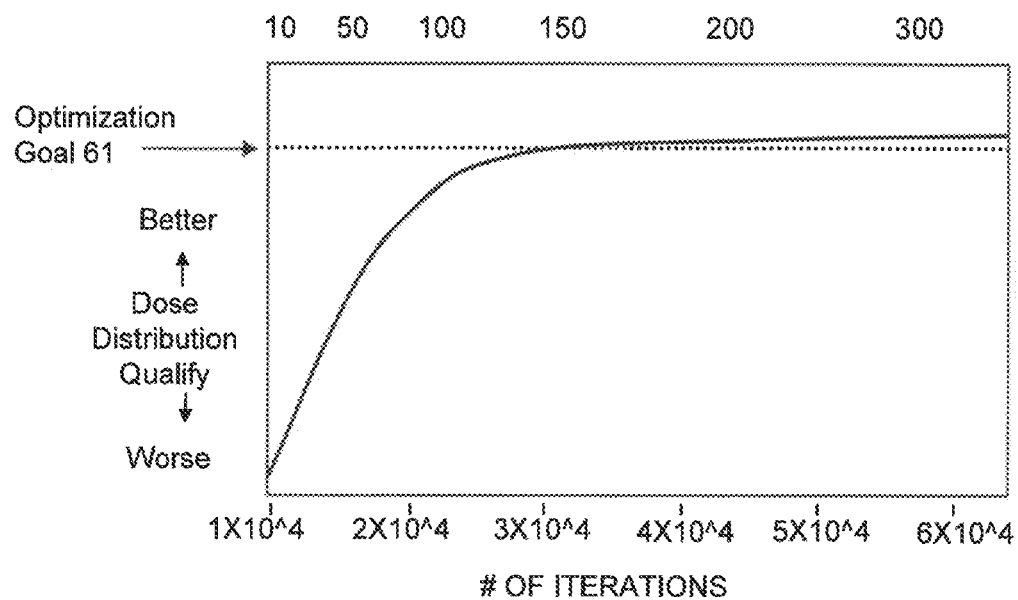
FIG. 9 graphically depicts the dose distribution quality versus the number of iterations for the FIG. 8 optimization method where the number of control points is varied over the optimization process.

An example of the method 150 results are shown in FIG. 9, which graphically depicts the dose distribution quality versus the number of iterations on a linear scale. FIG. 9 also shows that the number of control points 32 increases as the dose distribution gets closer to the optimization goals 61. It can be seen that by starting the optimization process with a relatively low number of control points 32 and then adding additional control points 32 as the optimization process approaches the optimization goals 61, the number of iterations required to achieve an acceptable solution has been dramatically reduced. FIG. 9 also shows that:
  the use of a small number of control points 32 at the beginning of the optimization process allows the optimization to get close to optimization goals 61 after a relatively small number of iterations;
  the introduction of additional control points 32 during the course of the optimization allows the flexibility to derive a dose distribution that meets optimization goals 61; and
  before the overall optimization process is terminated, a large number of control points 32 have been added and the parameters associated with these additional control points obey the associated optimization constraints, thereby preserving the dose calculation accuracy.

As with method 50 discussed above, method 150 describes a simple optimization process 154. In other embodiments, the block 154 optimization process may additionally or alternatively include other known optimization techniques such as: simulated annealing, gradient-based techniques, genetic algorithms, applying neural networks or the like.

In method 150, additional control points 32 are added when the level is incremented. In a different embodiment, the addition of one or more new control points may be treated as an alteration in block 66 of method 50. In such an embodiment, the procedures of block 180 associated with the addition of control points 32 may be performed as a part of block 66. In such an embodiment, the termination conditions of block 74 may also comprise an inquiry into whether the optimization has achieved a minimum number of control points 32. In other respects, such an embodiment is similar to method 50.

The result of optimization method 50 or optimization method 150 is a set of control points 32 and, for each control point 32, a corresponding set of parameters which includes: motion axes parameters (e.g. a set of motion axis positions for a particular radiation delivery apparatus that specify a corresponding beam position and beam orientation); beam shape parameters (e.g. a configuration of an MLC 35 including a set of positions for leaves 36 and, optionally, an orientation angle φ of MLC 35 about axis 37); and a beam intensity parameter. The set of control points 32 and their associated parameters form the basis of a radiation treatment plan which may then be transferred to a radiation delivery apparatus to effect the dose delivery.

The radiation intensity at a control point 32 is typically not delivered instantaneously to the subject but is delivered continuously throughout the portion of the trajectory 30 defined by that control point 32. The radiation output rate of the source 12 may be adjusted by the radiation delivery apparatus 10 and control system 23 so that the total radiation output for that control point 32 is the same as the intensity determined from the radiation plan. The radiation output rate will normally be determined by the amount of time required for the position of the radiation source 12 and the shape of the radiation beam to change between the previous, current and following control points 32.

A control system of the radiation delivery apparatus (e.g. control system 23 of radiation delivery apparatus 10) uses the set of control points 32 and their associated parameters to move radiation source 12 over a trajectory 30 while delivering radiation dose to a subject S. While the radiation delivery apparatus is moving over trajectory 30, the control system controls the speed and/or position of the motion axes, the shape of the beam and the beam intensity to reflect the motion axis parameters, beam shape parameters and the beam intensity parameters generated by the optimization methods 50, 150. It will be appreciated by those skilled in the art that the output of the optimization methods 50, 150 described above may be used on a wide variety of radiation delivery apparatus.

Pseudocode for Exemplary Embodiment of Optimization Process

Pre-Optimization
  Define 3-dimensional target and healthy tissue structures.
  Set optimization goals for all structures based on one or more of:
    Histograms of cumulative dose;
    Prescribed dose required to the target;
    Uniformity of dose to the target;
    Minimal dose to healthy tissue structures.
  Combine all optimization goals into a single quality factor (i.e. an optimization function).
  Define the trajectory for the radiation source:
    Select a finite number of control points; and
    Set the axis position for each axis at each control point.
Initialization
  Configure MLC characteristics (e.g. leaf width, transmission).
  Initialize level counter and initial number of control points.
  Initialize MLC leaf positions to shape the beam to the outline of the target.
  Perform dose simulation calculation to simulate dose distribution for all targets and healthy tissue structures:
    Generate a random distribution of points in each target/structure;
    Calculate the dose contribution from each initial control point; and
    Add the contribution from each initial control point.
  Rescale the beam intensity and corresponding dose so that the mean dose to the target is the prescription dose.
  Set constraints for:
    maximum change in beam shape parameters (i.e. movement of MLC leaves and/or rotations of MLC); and
    maximum change in beam intensity;
  for corresponding variations the relevant motor axes, including, where relevant:
    Gantry angle;
    Couch angle;
    Couch position; and
    MLC orientation.
  Set maximum intensity constraint.
  Set maximum treatment time constraint.
  Set optimization parameters:
    Probability of adding control points;
    At each iteration:
      Probability of changing beam shape parameter (e.g. MLC leaf position or MLC orientation) taking into account constraints on range of changes in MLC leaf position; and
      Probability of changing a radiation intensity taking into account constraints on range of intensity changes.
Optimization
While the optimization goals have not been attained:
1. Select a control point.
2. Select a beam shape alteration, intensity alteration, or add control points.
  If a beam shape alteration (e.g. a change in position of an MLC leaf) is selected:
    Randomly select an MLC leaf to change;
    Randomly select a new MLC leaf position;
    Ensure that the new MLC leaf position does not violate any positional constraints:
      Leaf does not overlap with opposing leaf;
      Leaf does not move outside of the initialized aperture; and
      Leaf does not violate the maximum movement constraints.
    Perform dose distribution simulation to calculate the new dose distribution for all structures.
    Calculate quality factor (i.e. optimization function) for new dose distribution.
    If the quality factor (i.e. optimization function) indicates an improvement, then accept the new leaf position.
  If an intensity alteration is selected:
    Randomly select a new intensity;
    Ensure that the new intensity does not violate any constraints:
      Intensity cannot be negative;
      Intensity cannot violate the maximum intensity constraint; and
      Intensity cannot violate the maximum intensity variation constraints.
    Perform dose distribution simulation to calculate the new dose distribution for all structures.

Calculate quality factor (i.e. optimization function) for new dose distribution.
If the quality factor (i.e. optimization function) indicates an improvement, then accept the new intensity.
If adding control points is selected:
Insert one or more control points within the existing trajectory.
Adjust optimization constraints (e.g. beam shape constraints and intensity constraints) based on addition of new control points.
Initialize beam shape parameters, intensity parameters and motion axes parameters of new control point(s).
Perform dose distribution simulation (incorporating the new control points) to calculate the new dose distribution for all structures.
Rescale all intensities so that the new intensities provide a mean dose to the target equal to the prescription dose.
Continue optimization with the added control points.
If the termination criteria have been attained:
Terminate the optimization; and
Record all optimized parameters (e.g. beam shape parameters, motion axes parameters and beam intensity parameters) and transfer optimized parameters to the radiation device.
If the termination criteria has not be attained:
Go to step (1) and select another beam shape alteration, intensity alteration, or add control points.

Example Implementation of a Particular Embodiment

Figure 10:
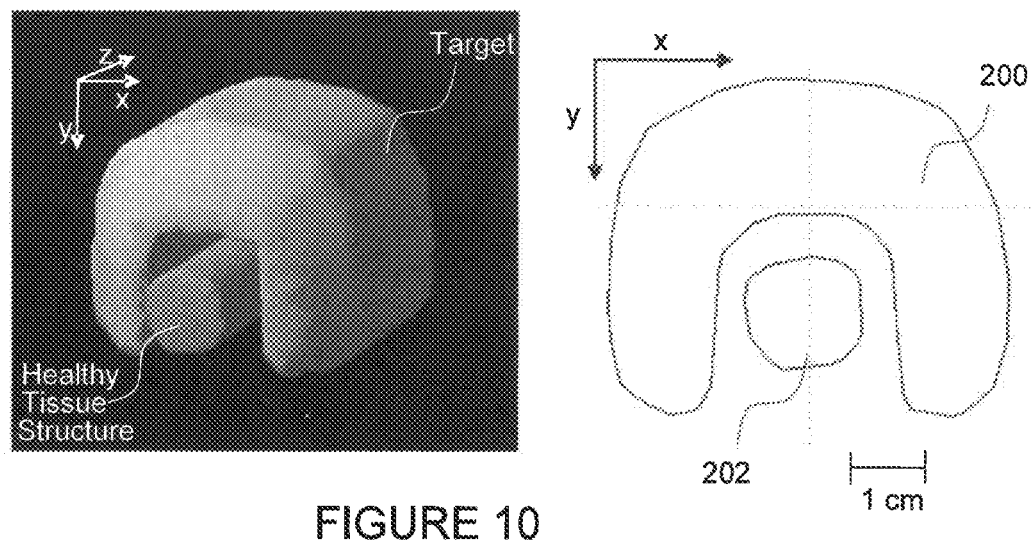
FIG. 10 is a depiction of sample target tissue and healthy tissue used in an illustrative example of an implementation of a particular embodiment of the invention.

The following represents an illustrative example implementation of a particular embodiment of the invention. FIG. 10 shows a three-dimensional example of target tissue 200 and healthy tissue 202 located within the body of a subject S. This example simulates a radiation delivery apparatus similar to radiation delivery apparatus 10 (FIG. 1).

Figure 11A:
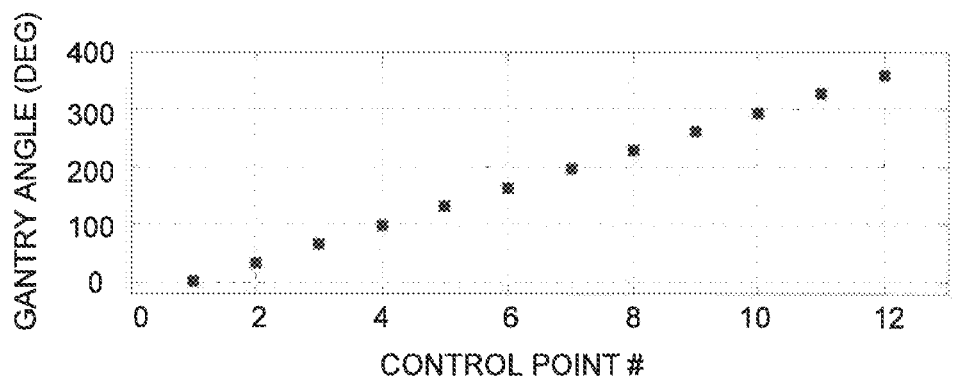
FIGS. 11A and 11B respectively depict the initial control point positions of the motion axes corresponding to a trajectory used in the FIG. 10 example.
Figure 11B:
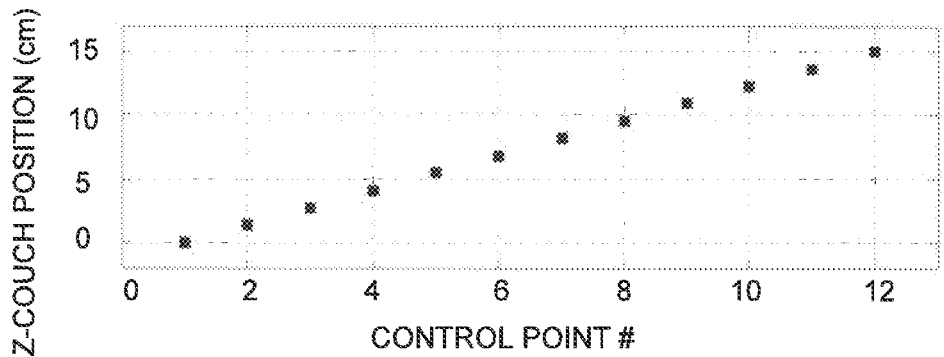

In this example, a trajectory 30 is defined as a 360° rotation of gantry 16 about axis 18 and a movement of couch 15 in the −Z direction (as shown in the coordinate system of FIG. 10). While this particular example uses a trajectory 30 involving two motion axes, it will be appreciated that trajectory 30 may involve movement of fewer motion axes or a greater number of motion axes. FIGS. 11A and 11B respectively depict the initial control point 32 positions of the relevant motion axes corresponding to the selected trajectory 30 (i.e. the angular positions of gantry 16 about axis 18 and the position of couch 15 in the Z dimension).

For this example, the optimization goals 61 included a desired dose distribution 60 having a uniform level of 70 Gy for target 200 and a maximum dose of 35 Gy for healthy tissue 202. At each initial control point 32, the beam shape parameters were initialized such that the leaves 36 of a MLC 35 shaped the beam into a beam's eye view outline of target 200. In this example, the orientation φ of MLC 35 was maintained constant at 45° and the orientation φ of MLC 35 was not specifically optimized. At each initial control point 32, the beam intensity was initialized so that the mean dose delivered to the target 200 was 70 Gy.

FIGS. 12A-F graphically depict the simulated dose distribution calculation at various stages of the optimization process by way of a dose volume histogram (DVH). In FIGS. 12A-F, dashed line 204 represents the percentage of the volume of healthy tissue 202 that receives a certain quantity of dose and the solid line 206 represents the percentage of the volume of target 200 that receives a certain quantity of dose. A DVH is a convenient graphical tool for evaluating dose distribution quality. It will be appreciated that movement of dashed line 204 downwardly and leftwardly represents a minimization of dose delivered to healthy tissue 202 and that movement of solid line 206 upwardly (as far as 100%) and rightwardly (as far as the dose distribution target (70 Gy in this example)) represents effective delivery of dose to target 200.

Figure 12B:
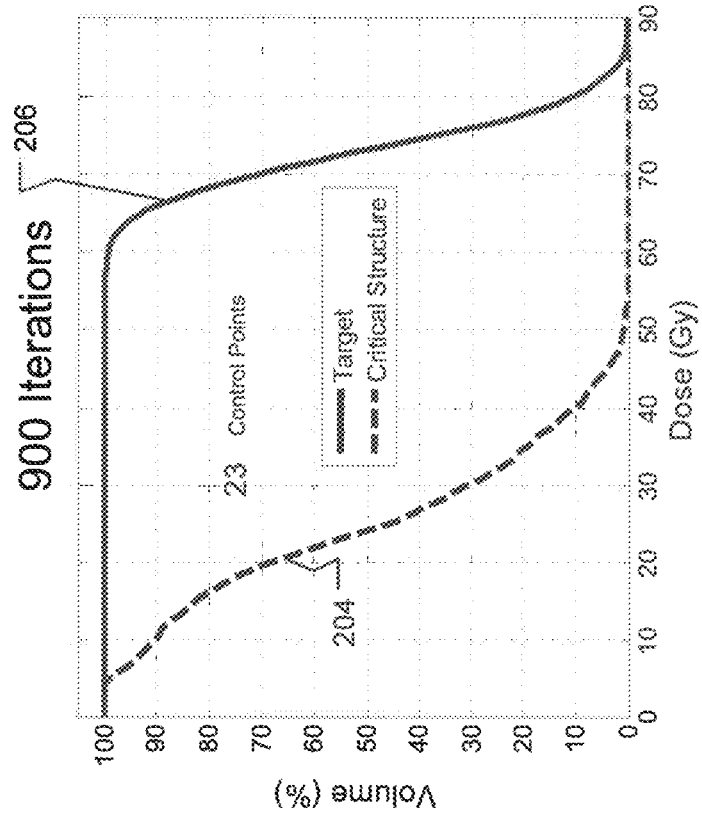
FIGS. 12A-12F depict a dose volume histogram (DVH) which is representative of the dose distribution quality at various stages of the optimization process of the FIG. 10 example.
Figure 12A:
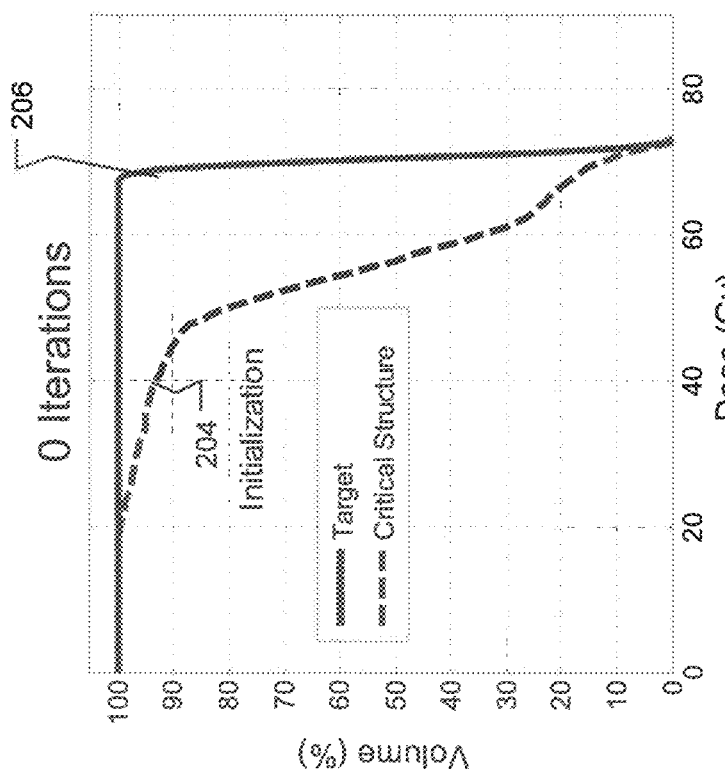
Figure 12D:
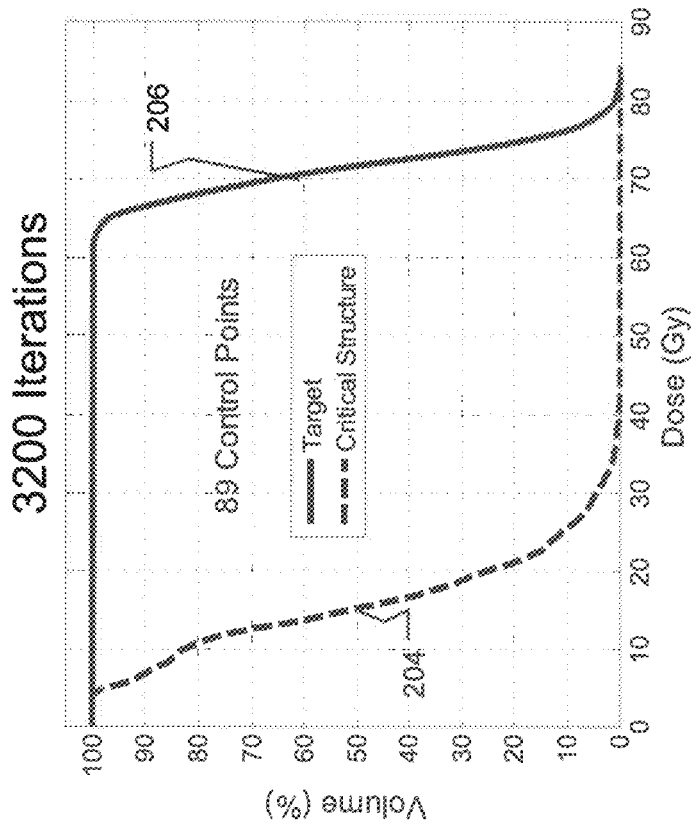
Figure 12C:
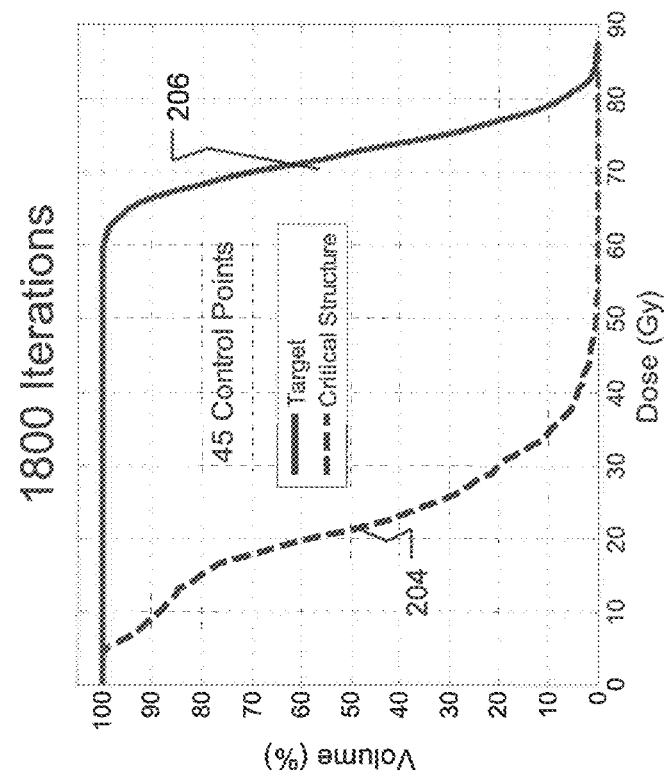
Figure 12F:
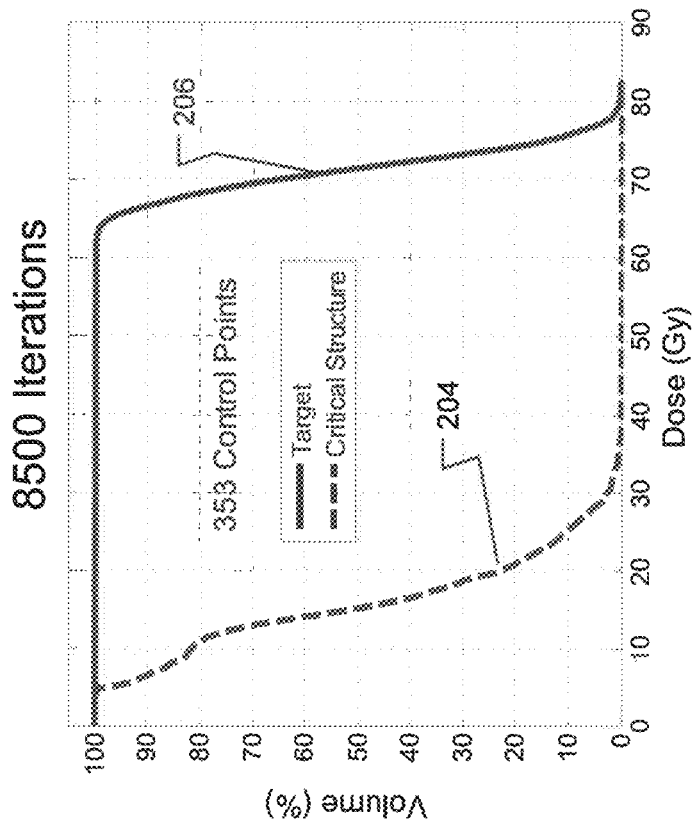
Figure 12E:
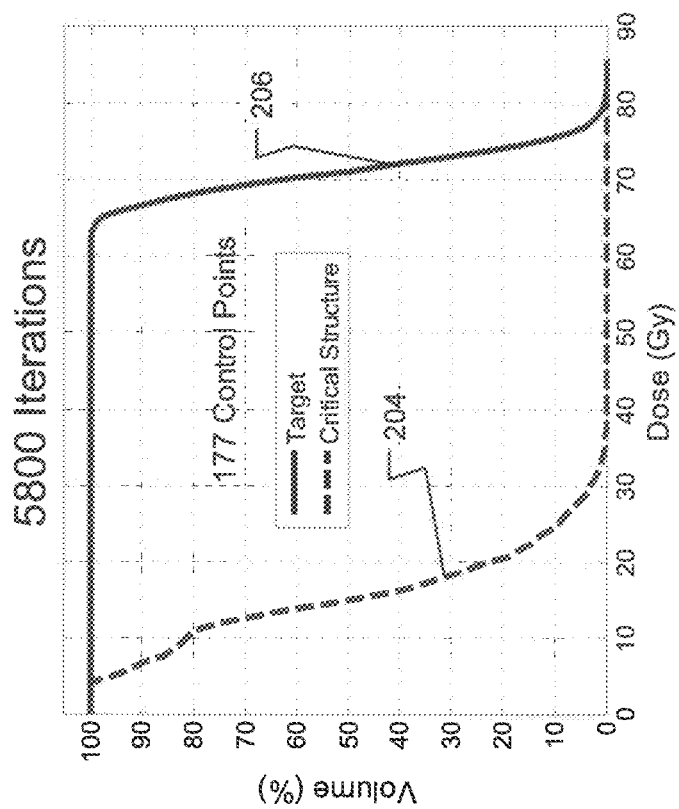

In this example, the optimization process starts at zero iterations with the 12 control points depicted in FIGS. 11A and 11B. The result at zero iterations is shown in FIG. 12A. In this example, the number of iterations and the number of control points are increased during the optimization process as shown in FIG. 12B-12F. After 900 iterations and an increase to 23 control points (FIG. 12B), a dramatic improvement in dose quality can be observed by the leftwardly and downwardly movement of dashed line 204. Further improvement is seen at 1800 iterations and 45 control points (FIG. 12C) and at 3200 iterations and 89 control points (FIG. 12D). The magnitude of the improvement in dose distribution quality per iteration decreases as the optimization progresses. FIGS. 12D-12F show that there is little improvement in the dose distribution quality between 3200 iterations and 89 control points (FIG. 12D), 5800 iterations and 177 control points (FIG. 12E) and 8500 iterations and 353 control points. As discussed above, notwithstanding the minimal improvement in dose distribution quality between FIGS. 12D and 12F, it can be useful to continue to increase the number of control points in the optimization to improve the accuracy of the dose simulation calculations.

Figure 13:
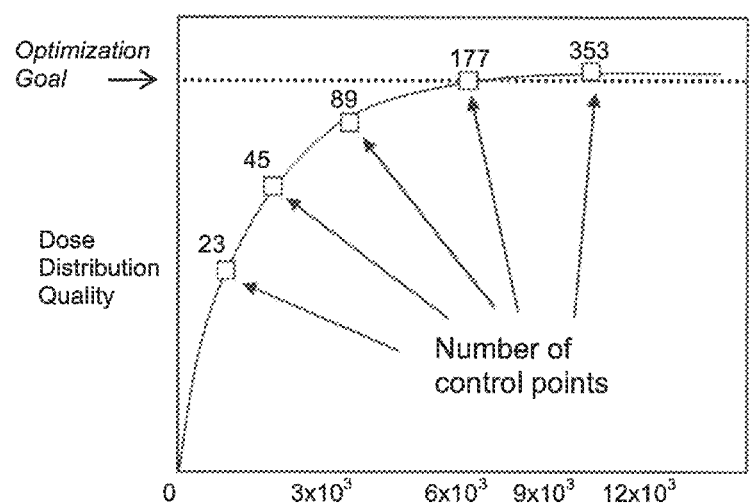
FIG. 13 another graphical depiction of the optimization process of the FIG. 10 example.

FIG. 13 is another graphical representation of this example which shows how the optimization goals 61 are achieved (to within an acceptable tolerance level) after 5800 iterations (177 control points).

Figure 14C:
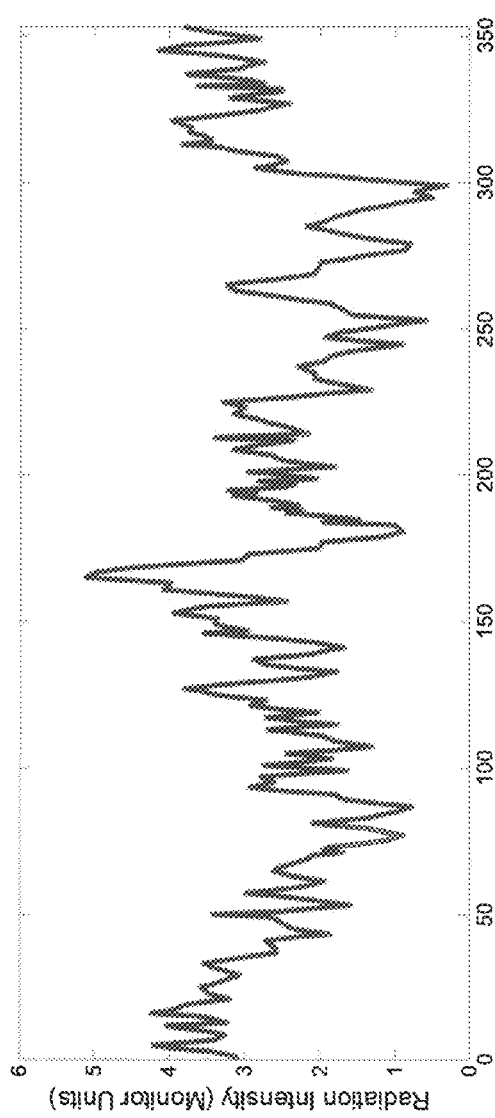
Figure 14D:
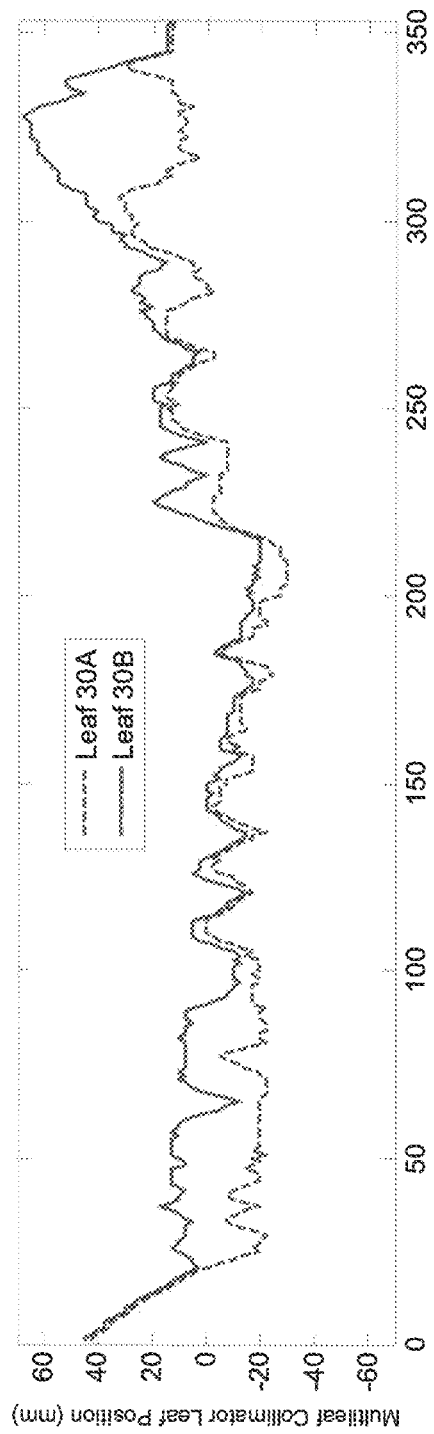

The optimization of this example was terminated after 11,000 iterations because the optimization goals had been attained (to within acceptable tolerances) and there was no further improvement in the dose distribution quality or accuracy with further iterations. The results of this example are shown in FIGS. 14A-14D, which respectively depict the motion axes parameters at each of the final control points (in this case, the orientation of gantry 16 about axis 18 (FIG. 14A) and the Z position of couch 15 (FIG. 14B)), the radiation intensity at each of the final control points (FIG. 14C) and the beam shaping parameters at each of the final control points (in this case, positions of two leaves 36 of an MLC 35 (FIG. 14D)). FIG. 14D shows that there are no dramatic changes in position of the illustrated leaves 36 of MLC 3, as constraints were applied to the allowable rate of change of the leaves 36 of MLC 35.

Figure 15:
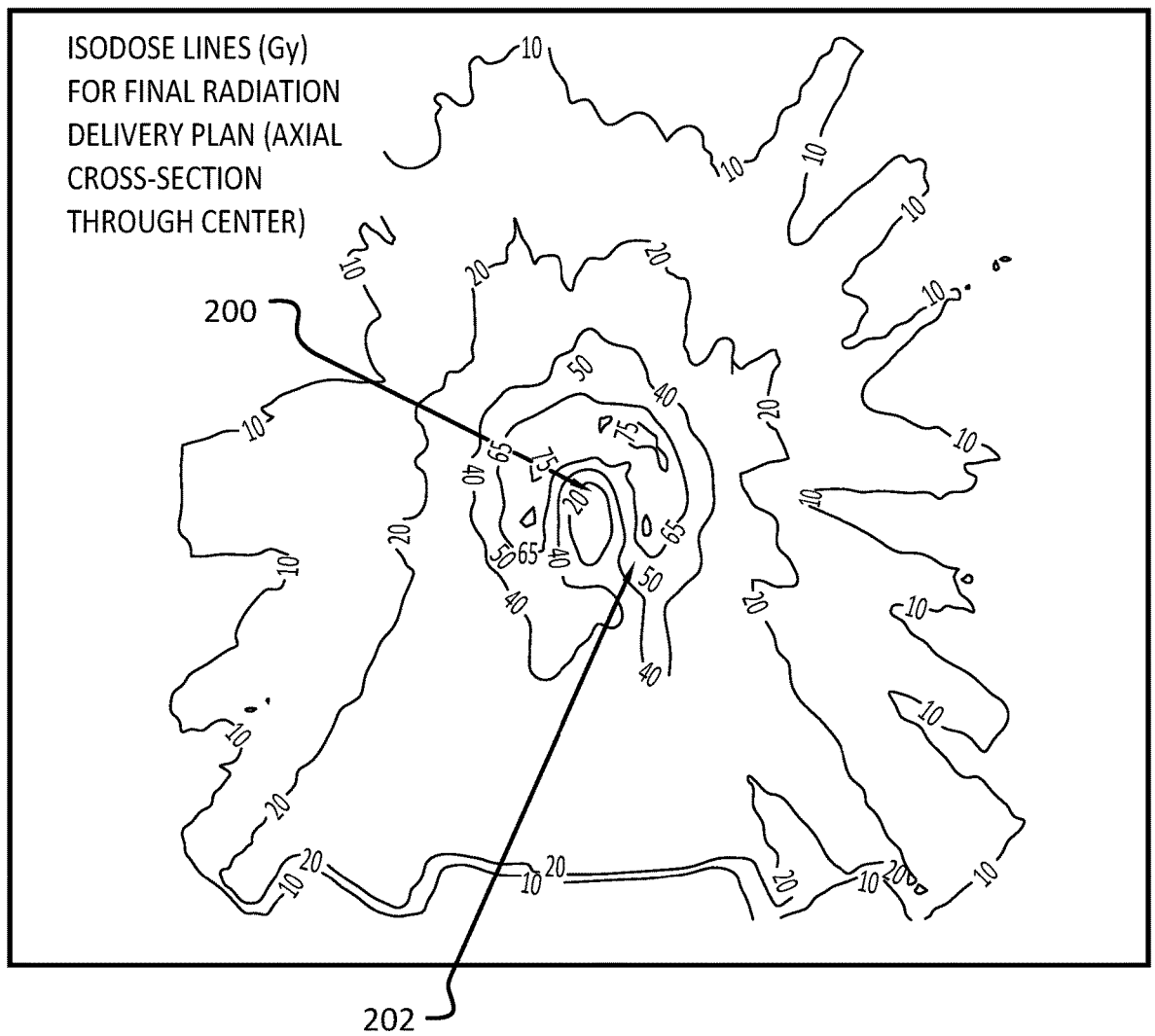
FIG. 15 plots contour lines of constant dose (isodose lines) in a two-dimensional cross-sectional slice of the target region in the FIG. 10 example.

FIG. 15 shows a two-dimensional cross-section of the optimized dose distribution. FIG. 15 shows plots contour lines of constant dose (isodose lines) indicating the regions of high and low dose. The amount of dose associated with each isodose line is enumerated on the line itself. Recalling the shape and relative position of the target 200 and healthy tissue 202 from FIG. 10, FIG. 15 shows that the high dose region is confined to the c-shape target area 200 while inside the concavity (i.e. the region of healthy tissue 202), the dose is significantly reduced.

In this example, the optimization time was 15.3 minutes. The treatment time required to deliver this dose distribution is approximately 1.7 minutes (assuming a dose rate of 600 MU/min).

In some embodiments, the methods described herein for delivering radiation dose to a subject S are used in conjunction with one or more imaging techniques and corresponding imaging apparatus. A suitable imaging technique is cone-beam computed tomography (cone-beam CT), which obtains a three-dimensional image of a subject. Cone-beam CT involves a radiation source and a corresponding sensor which can be suitably mounted on a radiation delivery apparatus. For example, a cone-beam CT radiation source may be mounted on gantry 16 of radiation delivery apparatus 10 and a corresponding sensor may be mounted on the opposing side of subject S to detect radiation transmitted through subject S. In some embodiments, the cone-beam CT source is the same as the treatment radiation source 12. In other embodiments, the cone-beam CT source is different than the treatment radiation source 12. The radiation delivery apparatus may move the cone-beam CT source and the CT sensor relative to subject S using the same motion axes (or substantially similar motion axes) used to move the treatment radiation source 12. At any point in which the cone-beam CT source is activated, a 2-dimensional projection image is formed from the transmission of radiation emanating from the cone-beam CT source, passing through subject S and impinging onto the corresponding sensor (which typically comprises a 2-dimensional array of radiation sensors). In some embodiments, the cone-beam CT radiation source and the treatment radiation source are time division multiplexed, such that the cone-beam CT sensor can distinguish between imaging radiation and treatment radiation.

In the acquisition of a 3-dimensional cone-beam CT image, the cone-beam CT source and sensor array move through a trajectory to acquire a plurality of 2-dimensional projection images of subject S. The plurality of 2-dimensional projection images are combined using methods known to those skilled in the art in order to reconstruct the 3-dimensional image of subject S. The 3-dimensional image may contain spatial information of the target and healthy tissue.

In some embodiments, a cone-beam CT image of subject S is acquired while delivering radiation to the subject. The 2-dimensional images may be taken from around the same trajectory 30 and in the same time interval that the radiation is delivered to subject S. In such embodiments, the resultant cone-beam CT image will be representative of the subject position, including the 3-dimensional spatial distribution of target and healthy tissue, at the time the subject was treated. The spatial distribution of target and healthy tissue can be referenced to the particular radiation delivery apparatus, allowing an observer to accurately assess what radiation dose distribution was actually delivered to the target and healthy tissue structures.

Subject S, and more particularly, the locations of target and healthy tissue, can move during radiation delivery. While some movement can be reduced or eliminated, one difficult movement to stop is respiration. For example, when subject S breathes, a target located inside the lung may shift as a function of the breathing cycle. In most dose simulation calculations, subject S is assumed to be stationary throughout the delivery. Accordingly, ordinary breathing by subject S can result in incorrect delivery of dose to the target and healthy tissue. In some embodiments, radiation source 12 is activated only when a position or configuration of subject S is within a specified range.

In some embodiments, one or more sensors are used to monitor the position of subject S. By way of non-limiting example, such sensors may include respirometer, infrared position sensors, electromyogram (EMG) sensors or the like. When the sensor(s) indicate that subject S is in an acceptable position range, radiation source 12 is activated, the configuration of beam-shaping mechanism 33 changes and the motion axes move as described in the radiation treatment plan. When the sensor(s) indicate that subject S is not in the acceptable position range, the radiation is deactivated, the configuration of beam-shaping mechanism 33 is fixed and the motion axes are stationary. An acceptable position range may be defined as a particular portion of the respiratory cycle of subject S. In such embodiments, the radiation treatment plan is delivered intermittently, with intervals where the radiation apparatus and radiation output are paused (i.e. when the subject is out of the acceptable position range) and intervals where the radiation apparatus and radiation output are resumed (i.e. when the subject is in the acceptable position range). Treatment delivery proceeds in this way until the treatment plan has been completely delivered. The process of position dependent delivery of radiation may be referred to as "position gating" of radiation delivery.

In one particular embodiment of the invention, cone-beam CT images are acquired while position gated treatment is being delivered to subject S. The acquisition of 2-dimensional projection images may also gated to the patient position, so that the cone-beam CT images will represent the position of subject S at the time of treatment delivery. Such embodiments have the additional benefit that the 2-dimensional cone-beam CT images are obtained with subject S in a consistent spatial position, thereby providing a 3-dimensional cone-beam CT with fewer motion artifacts.

As discussed above, in some embodiments where beam-shaping mechanism 33 comprises a MLC 35, it is possible to optimize beam-shape parameters including, without limitation: the positions of MLC leaves 36 and the corresponding shape of the MLC apertures 38; and the MLC orientation angle $\varphi$ about beam axis 37. In other embodiments where beam-shaping mechanism 33 comprises a MLC 35, it may be desired to maintain a constant MLC orientation angle $\varphi$ about beam axis 37—e.g. where a particular radiation delivery apparatus 10 does not permit adjustment of MLC orientation angle $\varphi$ during delivery and/or where processing power used in the optimization process is at a premium.

Where MLC orientation angle $\varphi$ is maintained constant, MLC 35 may have certain limitations in its ability to approximate arbitrary beam shapes. In such instances, the selection of the particular constant MLC orientation angle $\varphi$ may impact treatment plan quality and ultimately the radiation dose that is delivered to subject S. An example of this scenario is illustrated schematically in FIGS. 16A and 16B, where it is desired to provide a beam shape 301. In the FIG. 16A example, leaf-translation directions 41 are oriented substantially parallel with the motion of beam 14 along source trajectory direction 43 (i.e. MLC orientation angle $\varphi=0°$). In the FIG. 16B example, leaf-translation directions 41 are oriented substantially orthogonally to the motion of beam 14 along source trajectory direction 43 (i.e. MLC orientation angle $\varphi=90°$). It can be seen by comparing FIGS. 16A and 16B that when $\varphi=0°$ (FIG. 16A), the beam shape of MLC 35 does a relatively good job of approximating desired beam shape 301, whereas when $\varphi=90°$ (FIG. 16B), there are regions 303 where MLC does a relatively poor job of approximating desired beam shape 301.

Figure 16A:
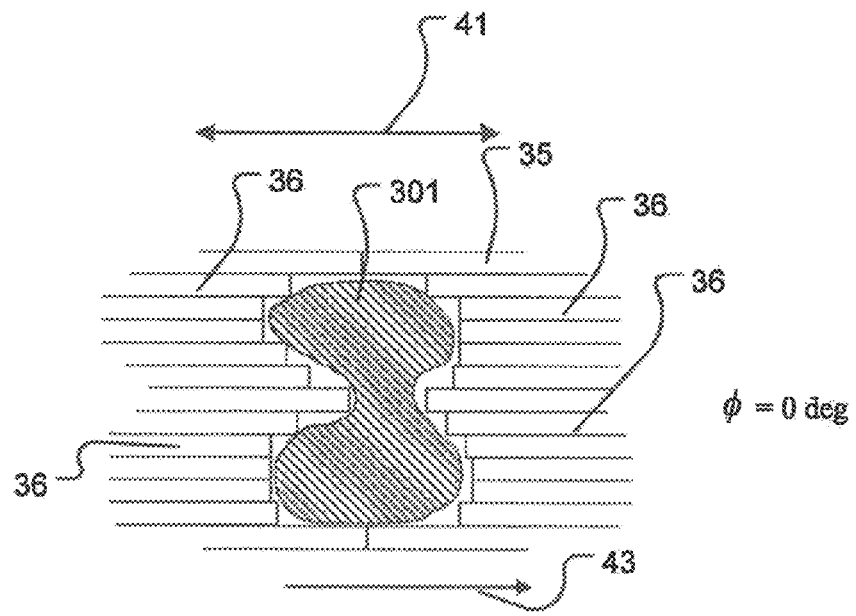
FIGS. 16A and 16B show examples of how the selection of a particular constant MLC orientation angle may impact treatment plan quality and ultimately the radiation dose that is delivered to a subject.
Figure 16B:
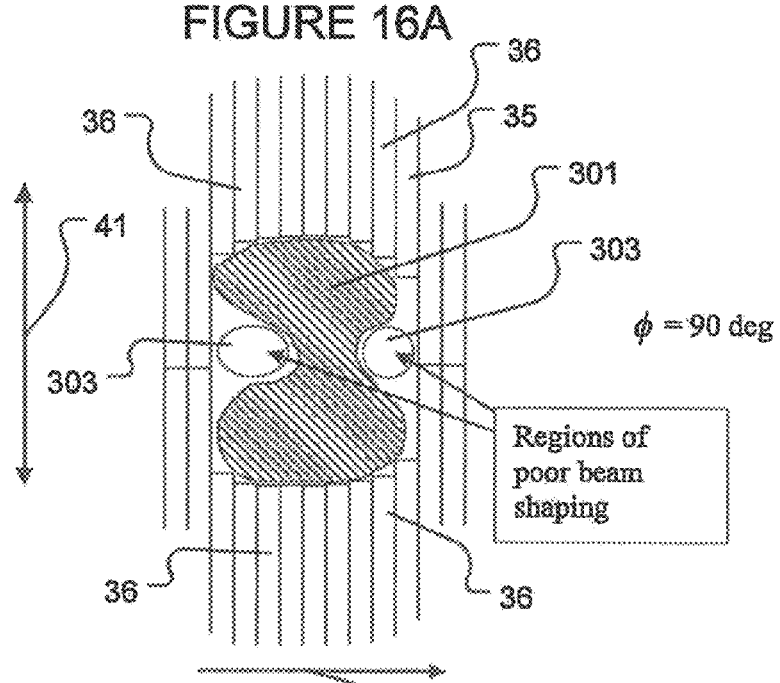

While not explicitly shown in FIGS. 16A and 16B, it will be understood that if desired beam shape 301 was rotated 90° from the orientation shown in FIGS. 16A and 16B, then the MLC orientation angle $\varphi=90°$ would produce a relatively accurate beam shape relative to the MLC orientation of $\varphi=0°$. Accordingly, selection of a constant MLC orientation $\varphi$ may impact treatment plan quality and ultimately the radiation dose that is delivered to subject S. It is therefore important to consider which MLC orientation angle $\varphi$ to select when using a constant MLC orientation angle φ to plan and deliver radiation to a subject S.

Figure 17:
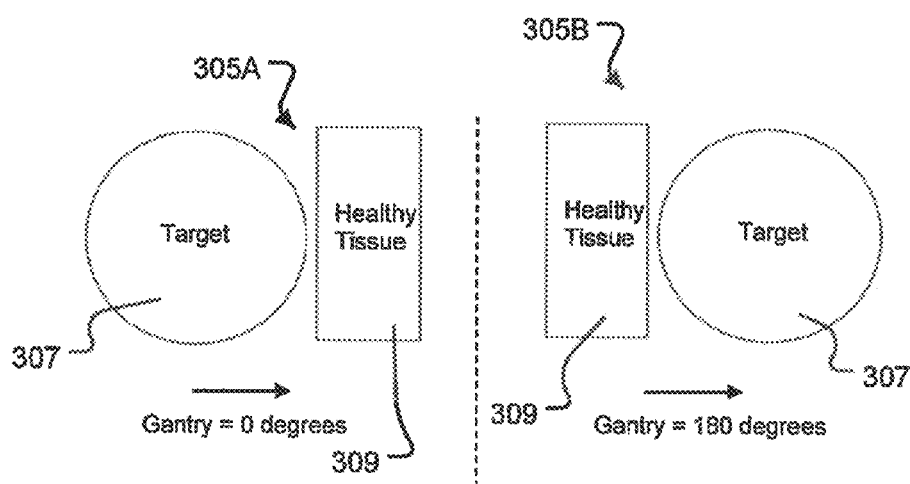
FIG. 17 schematically depicts how target and healthy tissue will look for opposing beam directions.

One aspect of the invention provides for radiation planning and delivery systems which provide a constant MLC orientation angle φ having a generally preferred value. Consider a trajectory 30 where radiation is delivered to a subject where there are substantially opposing radiation beams throughout the trajectory—i.e. beams that are parallel but have opposing directions. By way of non-limiting example, such a trajectory 30 may comprise rotation of gantry 16 through one full rotation of 180° or more. FIG. 17 shows the projections 305A, 305B of target 307 and healthy tissue 309 for opposing beam directions (e.g. a gantry angle of 0° (305A) and a gantry angle of 180° (305B). The projection of target 307 and healthy tissue 309 is approximately mirrored for the parallel and opposing beam directions.

It follows that a desirable beam shape from parallel and opposing beam directions will also be approximately mirrored. This observed symmetry may be exploited by selecting MLC orientation angles φ that result in a superior radiation plan. Consider the examples shown in FIGS. 16A and 16B with respect to the shaping capabilities of MLC 35. For the two orientations shown in FIG. 16A (φ=0°) and in FIG. 16B (φ=90°), mirroring the desired beam shape will not change the ability of MLC 35 to create desired beam shape 301 because of the mirror symmetry already inherent in MLC 35. In particular embodiments, MLC orientation angle φ is selected to exploit the mirroring of opposing beam projections by choosing an MLC orientation φ that is not 0° or 90° such that the MLC orientations φ with respect to the subject S will be different for opposing beam directions.

Figure 18A:
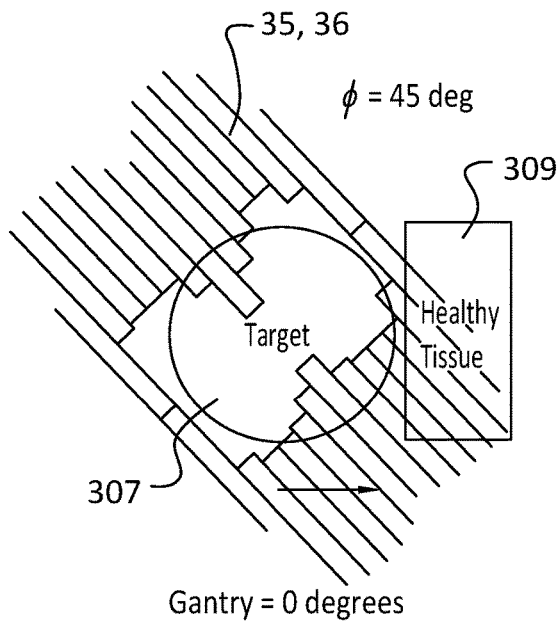
FIGS. 18A and 18B show an MLC and the respective projections of a target and healthy tissue for opposing beam directions corresponding to opposing gantry angles.
Figure 18B:
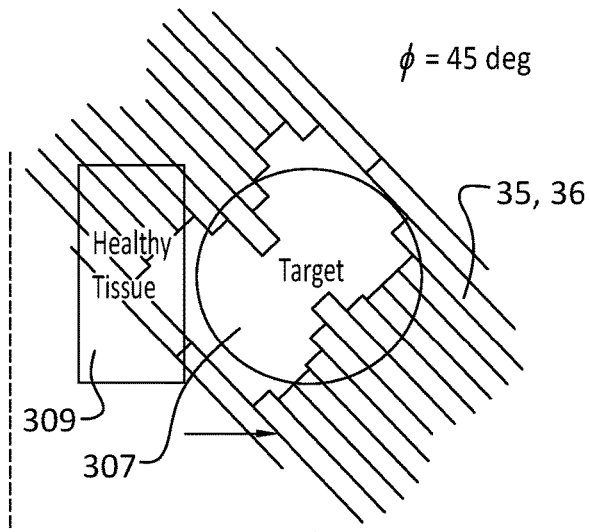
Figure 18C:
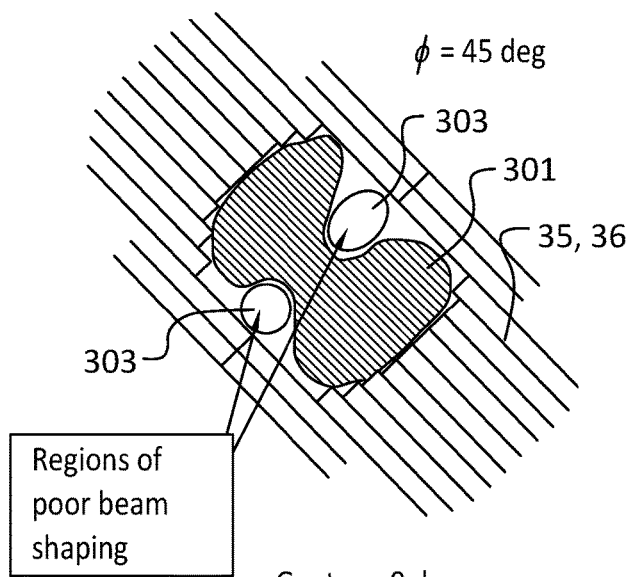
FIGS. 18C and 18D show an MLC and the respective projections of a desired beam shape for opposing beam directions corresponding to opposing gantry angles.
Figure 18D:
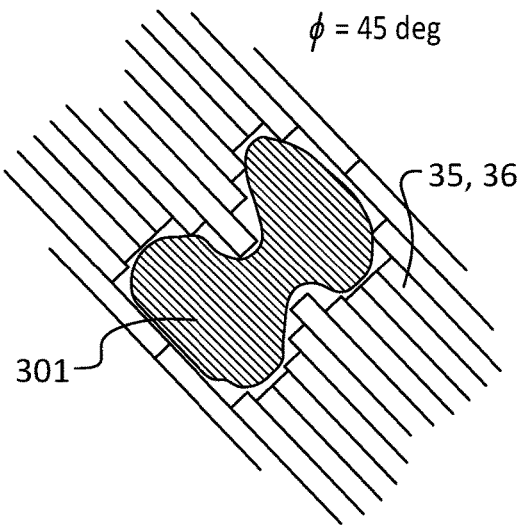

For example, choosing MLC orientation angle φ such that |φ|=45° (where |●| represents an absolute value operator) will result in MLC orientations that are orthogonal to one another (i.e. with respect to the projection of subject S) when the beam is oriented in opposing beam directions. This is shown in FIGS. 18A and 18B which show MLC 35 and the projections of target 307 and healthy tissue 309 for opposing beam directions corresponding to opposing gantry angles of 0° (FIG. 18A) and 180° (FIG. 18B) and in FIGS. 18C and 18D which show MLC 35 and the projections of desired beam shape 301 for opposing beam directions corresponding to opposing gantry angles of 0° (FIG. 18C) and 180° (FIG. 18D). With this MLC orientation angle |φ|=45°, the beam shaping limitations associated with constant MLC orientation angle φ are thereby reduced because effectively two different MLC orientation angles φ are available for opposing beam directions and may be used to provide a desired beam shape.

Other MLC orientation angles φ that are not φ=0° or φ=90° may also provide this advantage. Currently preferred embodiments incorporate MLC orientation angles φ such that |φ| is in a range 15°-75° and particularly preferred embodiments incorporate MLC angles φ where |φ| is in a range of 30°-60°. The benefit of selecting MLC orientation angles φ within these ranges may be realized for all substantially opposed beam orientations throughout the delivery of radiation and may be provided by any trajectories which comprise one or more substantially opposed beam directions. Non-limiting examples of such trajectories 30 include: trajectories 30 which comprise rotations of gantry 16 about axis 18 by any amount greater than 180° (e.g. 360° rotations of gantry 16 about axis 18) and trajectories 30 which comprise multiple planar arcs wherein at least one of the arcs comprises opposing beam directions. Selection of MLC orientation angles φ within these ranges is not limited to trajectories 30 comprising opposing beams and may be used for any trajectories. These advantages of increased MLC shaping flexibility may be manifested as increased plan quality, reduced delivery time, reduced radiation beam output requirements or any combination of the above.

A further desirable aspect of providing MLC orientation angles φ that are not φ=0° or φ=90° relates to physical properties of typical MLCs 35. Although individual MLC leaves 36 block most of radiation from radiation source 12, there is often some undesirable radiation leakage that permeates MLC 35 and there is a relatively large amount of radiation leakage at the edges of MLC leaves 36 where they translate independently relative to each other. Choosing a MLC orientation angle φ=0° with respect to the motion of beam 14 along source trajectory direction 43 may result in interleaf radiation leakage that is compounded in planes defined by the edges of MLC leaves 36 and the beam axis 37 for particular trajectories 30. MLC orientation angles φ other than φ=0° may cause the orientation of the interleaf leakage planes to change along the trajectory 30, thereby reducing any systematic accumulation of unwanted radiation leakage and corresponding unwanted dose within subject S.

The edges of MLC leaves 36 may be constructed with a tongue-and-groove shape on each side for reduction of interleaf leakage. For some beam shapes, such tongue-and-groove MLC leaf edges may cause an unwanted reduction in radiation dose delivered to subject S. Similar to the effect on inter-leaf leakage, the tongue-and-groove underdosage effect will be compounded along the leaf edges. Selecting MLC orientation angles φ other than φ=0° may reduce systematic underdosing of the subject S caused by these tongue-and-groove leaf edges.

Additional considerations that affect the selection of MLC orientation angle φ include the maximum speed of MLC leaves 36 as well as the ability of MLC 35 to create shapes that continuously block areas of important healthy tissue 309 while maintaining a relatively high dose to target 307.

When it is desirable to block a central portion of radiation beam 14, it can be more efficient to choose a MLC orientation angle φ other than φ=0°. In particular circumstances, blocking a central portion of radiation beam 14 may be achieved more efficiently when the MLC orientation angle φ is approximately φ=90°. In contrast, when there are dramatic changes in desired beam shape as source 12 moves along its trajectory 30, it may be difficult for MLC leaves 36 to move into position with sufficient speed. Generally, the desired projection shape 301 will change more rapidly in the direction 43 of source motion along trajectory 30. It may therefore be desirable to have leaf-translation axis 41 oriented to approximately the same direction 43 as the source motion along trajectory 30. Such a selection would result in a MLC orientation angle φ of approximately φ=0°.

The competing benefits/disadvantages of a MLC orientation angle φ of 0° versus 90° may be mitigated by using a MLC orientation angle φ that is substantially in between these two angles (i.e. approximately |φ|=45°. It will be appreciated that a MLC orientation angle φ of exactly |φ|=45° is not essential and other factors specific to the given subject S to be irradiated may need to be considered when selecting a MLC orientation angle φ.

Certain implementations of the invention comprise computer processors which execute software instructions which cause the processors to perform a method of the invention. For example, one or more data processors may implement the methods of FIG. 4A and/or FIG. 8 by executing software instructions in a program memory accessible to the data processors. The invention may also be provided in the form of a program product. The program product may comprise any medium which carries a set of computer-readable signals comprising instructions which, when executed by a data processor, cause the data processor to execute a method of the invention. Program products according to the invention may be in any of a wide variety of forms. The program product may comprise, for example: physical media such as magnetic data storage media including floppy diskettes, hard disk drives, optical data storage media including CD ROMs, DVDs, electronic data storage media including ROMs, flash RAM, or the like. The computer-readable signals on the program product may optionally be compressed or encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

While a number of exemplary aspects and embodiments have been discussed above, those of skill in the art will recognize certain modifications, permutations, additions and subcombinations thereof. For example:

In the embodiments described above, control points 32 used to define a trajectory 30 are the same as the control points used to perform the block 54 optimization process. This is not necessary. For example, a simple trajectory 30, such as an arc of gantry 16 about axis 18 (FIG. 1), may be defined by two control points at its ends. While such control points may define the trajectory, more control points will generally be required to achieve an acceptable treatment plan. Accordingly, the block 54, 154 optimization processes may involve using different (e.g. more) control points than those used to define the trajectory.

In the embodiments described above, constraints (e.g. constraints on the changes in beam position/orientation parameters between control points 32, constraints on the changes in beam shape parameters between control points 32 and constraints on the changes in the beam intensity between control points 32) are used throughout the optimization processes 54, 154. In other embodiments, the optimization constraints may be imposed later in the optimization process. In this manner, more flexibility is available in meeting the optimization goals 61 in an initial number of iterations. After the initial number of iterations is performed, the constraints may be introduced. The introduction of constraints may require that some beam position/orientation parameters, beam shape parameters and/or intensity parameters be changed, which may result in a need for further optimization to meet the optimization goals 61.

In the embodiments described above, the beam position and beam orientation at each control point 32 are determined prior to commencing the optimization process 54, 154 (e.g. in blocks 52, 152) and are maintained constant throughout the optimization process 54, 154 (i.e. optimization processes 54, 154 involve varying and optimizing beam shape parameters and beam intensity parameters, while trajectory 30 remains constant).

In other embodiments, the beam position and beam orientation parameters (i.e. the set of motion axis positions at each control point 32) are additionally or alternatively varied and optimized as a part of optimization processes 54, 154, such that optimization processes 54, 154 optimize the trajectory 30 of the radiation delivery apparatus. In such embodiments, optimization processes 54, 154 may involve placing constraints on the available motion axis positions and/or the rate of change of motion axis positions between control points 32 and such constraints may be related to the physical limitations of the particular radiation delivery apparatus being used to deliver the dose to the subject S.

In some embodiments, the radiation intensity may be held constant and the optimization processes 54, 154 optimize the beam shape parameters and/or the motion axis parameters. Such embodiments are suitable for use in conjunction with radiation delivery apparatus which do not have the ability to controllably vary the radiation intensity. In some embodiments, the beam shape parameters may be held constant and the optimization processes 54, 154 optimize the intensity and/or the motion axis parameters.

There are an infinite number of possible trajectories that can be used to describe the position and orientation of a radiation beam. Selection of such trajectories are limited only by the constraints of particular radiation delivery apparatus. It is possible to implement the invention using any trajectory capable of being provided by any suitable radiation delivery apparatus.

It is therefore intended that the following appended claims and claims hereafter introduced are interpreted to include all such modifications, permutations, additions and subcombinations as are within their true spirit and scope.

What is claimed is:

1. A method for delivering radiation dose to a target area within a subject, the method comprising:

defining a set of one or more optimization goals, the set of one or more optimization goals comprising a desired dose distribution in the subject and optimization of a metric based on a radiobiological model;

defining an initial trajectory for relative movement between a treatment radiation source and the subject and an initial plurality of control points along the initial trajectory;

iteratively optimizing a simulated dose distribution relative to the set of one or more optimization goals to determine one or more radiation delivery parameters associated with each of the control points;

wherein the one or more radiation delivery parameters comprise a position of the radiation source relative to the subject and wherein iteratively optimizing the simulated dose distribution comprises defining an optimized trajectory for relative movement between the radiation source and the subject based on the one or more radiation delivery parameters; and effecting relative movement between the treatment radiation source and the subject along the optimized trajectory and, while effecting the relative movement between the treatment radiation source and the subject along the optimized trajectory, delivering a treatment radiation beam from the treatment radiation source to the subject according to a determined radiation delivery plan to impart a dose distribution on the subject.

2. The method of claim 1 wherein optimization of a metric based on the radiobiological model comprises optimization of a metric measuring risk of a dose to non-diseased tissue.

3. The method of claim 2 wherein optimization of the metric based on the radiobiological model comprises limiting the delivery of the treatment radiation beam to critical structures outside of a target volume.

4. The method of claim 3 wherein the initial trajectory comprises one or more arcs, each arc involving relative movement between the radiation source and the subject within a corresponding plane.

5. The method of claim 4 wherein, the initial trajectory comprises a plurality of arcs, and, between successive ones of a first one and a successive one of the plurality of arcs, the initial trajectory comprises inter-arc relative movement between the radiation source and the subject, the inter-arc relative movement comprising movement such that the corresponding planes associated with each arc intersect one another.

6. The method of claim 4 wherein, the initial trajectory comprises a plurality of arcs, and, between successive ones of a first one and a successive one of the plurality of arcs, the initial trajectory comprises inter-arc relative movement between the radiation source and the subject, the inter-arc relative movement comprising movement such that the corresponding planes associated with each arc are parallel with one another.

7. The method of claim 1 comprising:
reaching one or more initial termination conditions;
adding one or more additional control points to obtain an increased plurality of control points;
iteratively optimizing the simulated dose distribution relative to the set of one or more optimization goals to determine one or more radiation delivery parameters associated with each of the increased plurality of control points.

8. The method of claim 7 wherein iteratively optimizing a simulated dose distribution relative to the set of one or more optimization goals to determine the one or more radiation delivery parameters associated with each of the control points comprises, for each iteration:
varying one or more of the radiation delivery parameters associated with one or more of the initial plurality of control points;
determining the simulated dose distribution based on the one or more varied radiation delivery parameters;
determining, based on an optimization algorithm and the simulated dose distribution based on the one or more varied radiation delivery parameters, whether to accept or reject the one or more varied radiation delivery parameters; and
when a determination is made to accept the one or more varied radiation delivery parameters, updating current radiation delivery parameters to include the one or more varied radiation delivery parameters.

9. The method of claim 8 wherein varying one or more of the radiation delivery parameters associated with one or more of the plurality of control points is subject to one or more initial optimization constraints.

10. The method of claim 9 wherein iteratively optimizing the simulated dose distribution to determine one or more radiation delivery parameters associated with each of the increased plurality of control points comprises, for each iteration:
varying one or more of the radiation delivery parameters associated with one or more of the increased plurality of control points;
determining the simulated dose distribution based on the one or more varied radiation delivery parameters;
determining, on the basis of the optimization algorithm and the simulated dose distribution based on the one or more varied radiation delivery parameters, whether to accept or reject the one or more varied radiation delivery parameters; and
when a determination is made to accept the one or more varied radiation delivery parameters, updating the current radiation delivery parameters to include the one or more varied radiation delivery parameters.

11. The method of claim 10 wherein varying one or more of the radiation delivery parameters associated with one or more of the increased plurality of control points is subject to one or more subsequent optimization constraints.

12. The method of claim 11 wherein the one or more radiation delivery parameters comprise one or more beam-shaping parameters.

13. The method of claim 12 wherein the one or more beam-shaping parameters comprise one or more configurations of a multi-leaf collimator.

14. The method of claim 13 wherein the one or more initial and one or more subsequent optimization constraints comprise position limitations on one or more leaves of the multi-leaf collimator.

15. The method of claim 11 wherein the one or more radiation delivery parameters comprise a beam intensity.

16. The method of claim 11 wherein at least one of the one or more subsequent optimization constraints is different than a corresponding at least one of the one or more initial optimization constraints.

17. The method of claim 16 wherein the at least one of the one or more subsequent optimization constraints is more restrictive than the corresponding at least one of the one or more initial optimization constraints.

18. The method of claim 1 wherein:
delivering the treatment radiation beam from the treatment radiation source to the subject comprises varying an intensity of the treatment radiation beam over at least a portion of the optimized trajectory; and
varying the intensity of the treatment radiation beam over at least a portion of the optimized trajectory comprises varying a radiation output rate of the treatment radiation source in accordance with the radiation delivery plan while effecting relative movement between the treatment radiation source and the subject along the optimized trajectory.

19. The method of claim 18 wherein delivering the treatment radiation beam from the treatment radiation source comprises varying a shape of the treatment radiation beam in accordance with the radiation delivery plan over at least a portion of the optimized trajectory while effecting relative movement between the treatment radiation source and the subject along the optimized trajectory.

20. A method according to claim 1 wherein effecting relative movement between the treatment radiation source and the subject along the optimized trajectory comprises effecting continuous relative movement between the treatment radiation source and the subject along the optimized trajectory.

* * * * *